,

US008765098B2

(12) United States Patent
Appel et al.

(10) Patent No.: US 8,765,098 B2
(45) Date of Patent: Jul. 1, 2014

(54) STAR POLYMERS, METHODS OF PREPARATION THEREOF, AND USES THEREOF

(75) Inventors: Eric Andrew Appel, Los Alamitos, CA (US); James Lupton Hedrick, Pleasanton, CA (US); Victor Yee-Way Lee, San Jose, CA (US); Robert Dennis Miller, San Jose, CA (US); Joseph Sly, San Jose, CA (US)

(73) Assignees: International Business Machines Corporation, Armonk, NY (US); The Board of Trustees of The Leland Stanford Junior University, Palo Alto, CA (US)

( * ) Notice: Subject to any disclaimer, the term of this patent is extended or adjusted under 35 U.S.C. 154(b) by 930 days.

(21) Appl. No.: 12/750,147

(22) Filed: Mar. 30, 2010

(65) Prior Publication Data
US 2011/0243848 A1    Oct. 6, 2011

(51) Int. Cl.
*A61K 49/00*    (2006.01)
*A61K 9/00*    (2006.01)

(52) U.S. Cl.
USPC .......................................... 424/9.1; 424/400

(58) Field of Classification Search
USPC ................................................ 424/9.1, 400
See application file for complete search history.

(56) References Cited

U.S. PATENT DOCUMENTS

| | | | |
|---|---|---|---|
| 4,847,328 | A | 7/1989 | Hutchins et al. |
| 5,543,158 | A | 8/1996 | Gref et al. |
| 6,210,717 | B1 | 4/2001 | Choi et al. |
| 6,252,014 | B1 | 6/2001 | Knauss |
| 6,383,500 | B1 | 5/2002 | Wooley et al. |
| 6,491,903 | B1 | 12/2002 | Forster et al. |
| 6,699,724 | B1 | 3/2004 | West et al. |
| 6,730,334 | B2 | 5/2004 | Zhao |
| 7,160,934 | B2 | 1/2007 | Soga et al. |
| 7,265,186 | B2 | 9/2007 | Zhao |
| 7,544,740 | B2 | 6/2009 | Wang et al. |
| 7,579,429 | B2 | 8/2009 | Baker et al. |
| 7,585,363 | B1 * | 9/2009 | Royster et al. ............... 106/412 |
| 2002/0049261 | A1 | 4/2002 | Soga et al. |
| 2003/0105245 | A1 | 6/2003 | Amsden |
| 2008/0095699 | A1 | 4/2008 | Zheng et al. |
| 2010/0015433 | A1 | 1/2010 | Arfsten et al. |

FOREIGN PATENT DOCUMENTS

| | | |
|---|---|---|
| WO | 2007048423 A1 | 5/2007 |
| WO | 2007051252 A1 | 5/2007 |
| WO | 2009049089 A1 | 4/2009 |

OTHER PUBLICATIONS

Wiltshire et al., Macromolecules, 2006, 39, 9018-9027.*
Blencow et al., Polymer, 50 (2009) 5-32.*
Kim et al., J. Applied Polym. Sci., vol. 111, 1706-1712 (2009).*
Biela, et al., "One-Pot Synthesis of Star-Shaped Aliphatic Polyesters with Hyperbranched Cores and Their Characterization with Size Exclusion Chromatography," J.Polymer Science Part A: Polymer Chemistry, vol. 44, 4214-4221 (2006).
Bourissou, et al., "Recent advances in the controlled preparation of poly(a-hydroxy acids): Metal-free catalysts and new monomers," Comptes Rendus Chimie, 10 (2007), 775-794.
Coulembier, et al., "From controlled ring-opening polymerization to biodegradable aliphatic polyester: Especially poly(b-malic acid) derivatives," Prog. Polym. Sci., 31 (2006), 723-747.
Dove, "Controlled ring-opening polymerisation of cyclic esters: polymer blocks in self-assembled nanostructures," Chem. Commun., 2008, 6446-6470.
Jerome, et al., "Recent advances in the synthesis of aliphatic polyesters by ring-opening polymerization," Advanced. Drug Delivery Reviews, 60 (2008), 1056-1076.
Kamber, et al., "Organocatalytic Ring-Opening Polymerization", Chem. Rev., 2007, 107 (12), 5813-5840.
Kamber, et al., "N-Heterocyclic Carbenes for the Organocatalytic Ring-Opening Polymerization of #-Caprolactone," Macromolecules, 2009, 42 (5), 1634-1639).
Pounder, et al., "Metal free thiol-maleimide 'Click' reaction as a mild functionalisation strategy for degradable polymers", Chem. Commun., 2008, 5158-5160.
Radowski, et al., "Supramolecular Aggregates of Dendritic Multishell Architectures as Universal Nanocarriers," Angew. Chem. Int. Ed. 2007, 46, 1265-1269.
Wiltshire, et al., "Degradable Core Cross-Linked Star Polymers via Ring-Opening Polymerization," Macromolecules, 2006, 39 (13), 4282-4285.
Xiong, et al., "Synthesis of PEG-Armed and Polyphosphoester Core-Cross-Linked Nanogel by One-Step Ring-Opening Polymerization," Macromolecules, 2009, 42 (4), 893-896.
An et al., "Synthesis of amphiphilic star block copolymers of polystyrene with PEG core via ATRP-control of chain architecture and the formation of core-shell type globular structure", Polymer vol. 47, (2006), 4154-4162, US.
Csihony, et al., "Single-Component Catalyst/Initiators for the Organocatalytic Ring-Opening Polymerization of Lactide", J. Am. Chem. Soc., vol. 127, No. 25, (2005), 9079-9084. Published on Web Jun. 4, 2005, US.

(Continued)

*Primary Examiner* — Michael G Hartley
*Assistant Examiner* — Robert Cabral
(74) *Attorney, Agent, or Firm* — Michael R. Roberts

(57) ABSTRACT

A composition of matter comprising an amphiphilic star polymer, the star polymer comprising a crosslinked microgel core and 6 or more independent polymer arms covalently linked to the core, the 6 or more arms each comprising a hydrophilic polymer chain segment and a hydrophobic polymer chain segment; wherein each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million.

33 Claims, 12 Drawing Sheets

(56) References Cited

OTHER PUBLICATIONS

Stjerndahl, et al.,"Industrial Utilization of Tin-Initiated Resorbable Polymers: Synthesis on a Large Scale with a Low Amount of Initiator Residue", Biomacromolecules, vol. 8., No. 3, (2007), 937-940. Published on web Feb. 23, 2007, Amer. Chemical Society, US.

Bosman, et al., "A Modular Approach toward Functionalized Three-Dimensional Macromolecules: From Synthetic Concepts to Practical Applications," J. Am. Chem. Soc. 2003, 125, 715-728; Published on Web Dec. 18, 2002.

Ren, et al., "Organic Catalyst-Mediated Ring-Opening Polymerization for the Highly Efficient Synthesis of Polyester-based Star Polymers," ACS Macro Letters 2012, 1, 681-686; published May 17, 2012.

* cited by examiner

TBDP
(Porphyrin, (M=2H))

Loaded Star Polymer
(Example 12)

STAR POLYMERS, METHODS OF PREPARATION THEREOF, AND USES THEREOF

GOVERNMENT SUPPORT

This invention was made with Government support under Agreement No. DMR-0213618 awarded by the National Science Foundation. The Government has certain rights in this invention.

BACKGROUND

The present invention relates to star polymer compositions, methods of their preparation and uses thereof, particularly water soluble star polymers comprising amphiphilic arms that create a core-shell (hydrophobic-hydrophilic) structure.

Star polymers are an increasingly attractive target for materials research. As used herein, the term "star polymer" is a uni-molecular, globular, soft matter nanoparticle comprising six or more polymer arms emanating from a central core. The uni-molecular micelle type structure overcomes reliance on dynamic self-assembly of independent polymer chains to form stable micellar structures. There are typically two structural classes of star polymer. A "static core" star polymer is constructed from a pre-formed core. The pre-formed core can be molecular or macromolecular. The polymer arms can be synthetically attached to the pre-formed core to produce the star polymer, or the arms can be synthetically grown from the surface of the pre-formed core. A "microgel core" star polymer, on the other hand, is not constructed from a pre-formed core. A microgel core star polymer comprises a core derived from a polymer synthesis, during which the polymer arms of the structure become covalently bound to a growing microgel network. Many examples of star polymer structures that comprise essentially homopolymer arms have been described.

Of specific interest are star polymer structures comprising amphiphilic polymer arms that can effectively form a partitioned hydrophobic environment within the nanoparticle structure in certain solvents. Star polymers comprising amphiphilic polymer arms have been disclosed. Qiao, et al., WO2007/051252 A1, discloses biodegradable star polymers formed by ring opening polymerization of cyclic carbonyl monomers using metal catalysts. Meier et al., WO2007/048423 A1; Lin et al., Biomolecules, vol. 9(10), (2008), pages 2629-36; and An et al., Polymer, vol. 47, (2006), pages 4154-62 describe organic soluble (i.e., non-water soluble) amphiphilic core-shell star polymers. The "shell" portion contains the polymer arms, generally attached to a static core (e.g., dendrimers, pentaerythritol, and the like). The shell has an inner hydrophilic region and an outer hydrophobic region, each of various compositions. Alternatively, Kreutzer et al., Macromolecules, vol. 39(13), (2006), pages 4507-16, and Zhao et al., U.S. Pat. No. 7,265,186 B2, constructed water soluble amphiphilic core-shell star polymers comprising arms that present a hydrophilic outer region of various compositions and a hydrophobic inner region of various compositions, attached to a static core (e.g., dendrimers, pentaerythritol, etc). Fukukawa, et al., Biomacromolecules, vol. 9(4), (2008), pages 1329-39, disclose water soluble star polymers comprising hydrophilic outer and inner shell regions, attached to a microgel core of varying hydrophobicity composed of either poly(ethylene glycol diacrylate) or poly(divinylbenzene). Conversely, Gao, et al., Macromolecules, vol. 41(4), (2008), pages 1118-1125 describe star polymers comprising a hydrophobic outer shell and a hydrophobic inner shell attached to a microgel core.

Known amphiphilic star polymers have one or more of the following drawbacks, particularly when considered for use as carriers of biologically active materials for gene and/or drug delivery: insufficient water solubility, insufficient hydrophilic/hydrophobic balance of the outer shell and inner shell, insufficient biocompatibility and/or biodegradability, and/or structural limitations associated with the use of a static core.

SUMMARY

Accordingly, in an embodiment, a composition of matter comprises an amphiphilic star polymer, the star polymer comprising a crosslinked microgel core and 6 or more independent polymer arms covalently linked to the core, the 6 or more arms each comprising a hydrophilic polymer chain segment and a hydrophobic polymer chain segment; wherein each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million.

In another embodiment, a composition comprises:

an amphiphilic star polymer, the star polymer comprising a living microgel core of crosslinked polymeric material and 6 or more independent polymer arms emanating from the core, wherein i) the core includes 6 or more sites capable of further synthetic transformation, ii) each of the 6 or more sites includes a functional group selected from the group consisting of alcohols, amines, carboxylic acids, azides, alkynes, alkenes, halogen groups, and combinations thereof, and iii) each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million; and a biologically active material in contact with the microgel core and/or with the 6 or more independent polymer arms.

In another embodiment, a method comprises:

agitating a mixture comprising i) a polymer arm precursor comprising an initiator group, a hydrophobic polymer chain segment, and a hydrophilic polymer chain segment, ii) a core precursor material comprising two or more polymerizable groups, iii) an organocatalyst, iv) an optional accelerator, and v) an optional solvent, thereby forming an amphiphilic star polymer by polymerization of the core precursor material; wherein a) the star polymer comprises a crosslinked living microgel core derived from the core precursor material, b) the star polymer comprises 6 or more independent polymer arms covalently linked to the core, the 6 or more polymer arms being derived from the polymer arm precursor, and c) each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million.

In another embodiment, a method comprises:

forming a mixture of an amphiphilic star polymer and a biologically active material in a first solvent; and injecting the mixture into a second solvent, the second solvent being a non-solvent for the biologically active material, thereby forming nanoparticles of a loaded star polymer;

wherein i) the star polymer comprises a crosslinked living microgel core and 6 or more independent polymer arms covalently linked to the core, ii) the 6 or more polymer arms each comprise a hydrophobic polymer chain segment and a hydrophilic polymer chain segment, and iii) each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million.

In another embodiment, an aqueous mixture comprises a star polymer comprising a crosslinked living microgel core and 6 or more independent polymer arms covalently linked to the core, the 6 or more arms each comprising a hydrophilic polymer chain segment and a hydrophobic polymer chain segment, wherein each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million; and a biologically active material in contact with the microgel core and/or with the 6 or more independent polymer arms.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIG. 4A shows the total loss of dye within 60 minutes at a temperature of 37° C. and a pH of 13.5. The near infrared absorbance at 900 nm is also shown. FIG. 4B shows the effect of pH on the release rate, and indicates the release time can be extended to approximately 30 hours by lowering the pH to about 11.5.

DETAILED DESCRIPTION

Figure 1A:
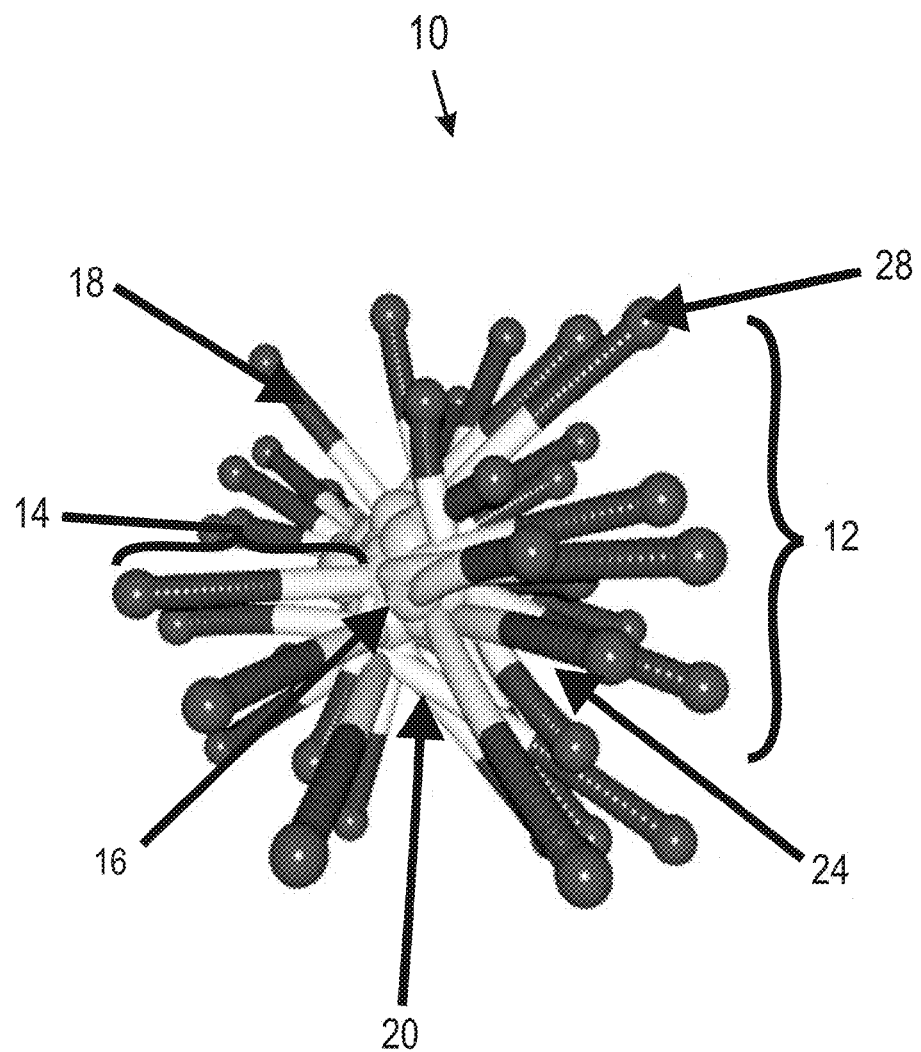
FIG. 1A is a 3-dimensional molecular model of an amphiphilic star polymer having a hydrophilic peripheral segment of the polymer arm and a hydrophobic inner segment.
Figure 1B:
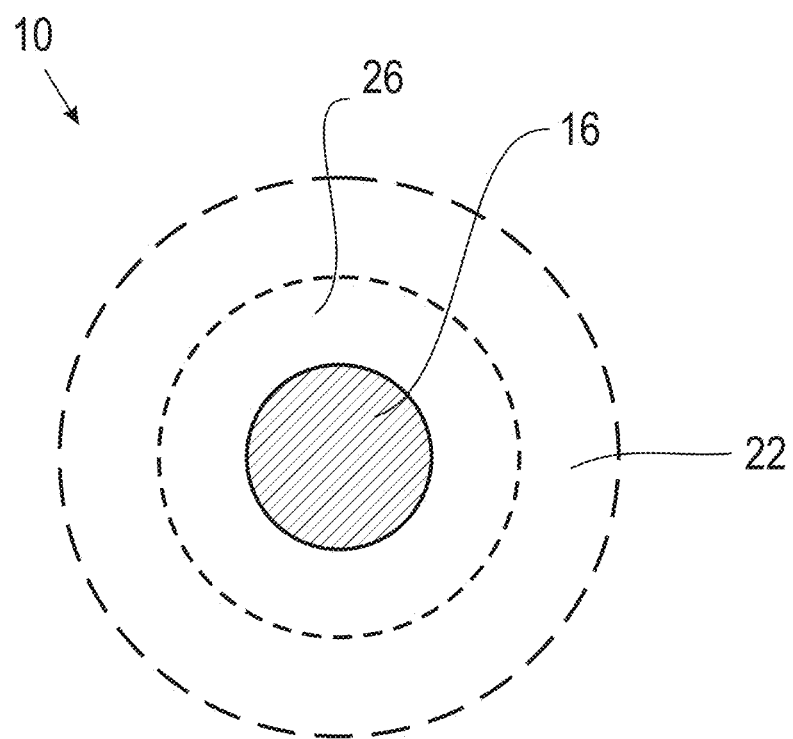
FIG. 1B is a cross-sectional view of a layer diagram of the amphiphilic star polymer of FIG. 1A, depicting the core shell structure, wherein the shell comprises a outer hydrophilic peripheral shell and a hydrophobic inner shell.

The invention is based on compositions comprising unimolecular star polymers, illustrated in one example in the three-dimensional molecular model of FIG. 1A and the graphical layer diagram of FIG. 1B. Star polymer 10 comprises a shell 12 composed of six or more independent amphiphilic polymer arms 14, each of which is covalently linked to a central microgel core 16. A polymer arm comprises a peripheral hydrophilic chain segment 18 and an inner hydrophobic chain segment 20. Shell 12 has two regions, a hydrophilic outer shell region 22 (FIG. 1B) comprising peripheral hydrophilic chain segments 18 and interstitial region 24 (FIG. 1A), and a hydrophobic inner shell region 26 composed of the hydrophobic inner chain segments 20 and interstitial region 24. The dashed boundary lines around outer shell region 22 and inner shell region 26 in FIG. 1B indicate the interstitial area is shared by the outer and inner shell regions. The microgel core 16 can be either hydrophobic or hydrophilic. The outer shell region 22, the inner shell region 26, and/or the microgel core 16 can further contain specific sites for further functionalization, which can be useful in controlling chemical interactions that favor the binding of, or the release of, a cargo material. For example, the microgel core 16 can be a living core, capable of initiating a polymerization or undergoing a different chemical modification. As another non-limiting example, the polymer arms 14 can comprise a functionally useful end group 28, such as a galactose moiety capable of selective recognition of liver cells. The amphiphilic arms and the microgel core can be formed by polymerization of a vinyl monomer, or more preferably by ring opening polymerization of a cyclic carbonyl monomer. The star polymers are useful, for example, as carriers for gene and drug delivery, materials that can influence stem cell differentiation, and in particular as carriers for materials useful in diagnostics or cellular imaging, such as a contrast enhancing agent.

"Restricted metals" herein include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Each one of the foregoing restricted metals has a concentration in the star polymer of greater than or equal to 0 parts per million and less than or equal to 100 parts per million (ppm). More particularly, each one of the foregoing restricted metals has a concentration in the star polymer of greater than or equal to 0 parts per billion and less than or equal to 100 parts per billion (ppb). Even more particularly, each one of the foregoing restricted metals has a concentration in the star polymer of greater than or equal to 0 parts per trillion and less than or equal to 100 parts per trillion (ppt). Preferably, each individual restricted metal has a concentration of 0 parts per million in the star polymer (i.e., the concentration is below the detection limits).

No restriction is placed on the concentration of boron, silicon, or any individual alkali metal in the star polymer, with the proviso that the star polymer has desirable properties, such as amphiphilic properties The term "biodegradable" is defined by the American Society for Testing and Materials as a degradation caused by biological activity, especially by enzymatic action, leading to a significant change in the chemical structure of the material. For purposes herein, a material is biodegradable if it undergoes 60% biodegradation within 180 days in accordance with ASTM D6400.

Herein, an amphiphilic material is a material that can be dispersed in an aqueous mixture in the form of nano-sized particles having a circular cross-sectional diameter of 2 nm to 500 nm.

No limitation is placed on the cargo material, with the proviso that the loaded star polymer can be dispersed in aqueous solution in the form of nano-sized particles, and the loaded star polymer comprising the cargo performs a useful function. Cargo materials include biologically active substances. Exemplary biologically active substances include biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), chromophores that aid in diagnostics (e.g., porphyrinoid compounds, including porphyrins and phthalocyanines), radioactive variants of the foregoing, and combinations of the foregoing. Some of the biologically active substances can alter the chemical structure and/or activity of a cell, or can selectively alter the chemical structure and/or activity of a cell type relative to another cell type. As an example, one desirable change in a chemical structure can be the incorporation of a gene into the DNA of the cell. A desirable change in activity can be the expression of the transfected gene. Another change in cell activity can be the induced production of a desired hormone or enzyme. A desirable change in cell activity can also be the selective death of one cell type over another cell type. No limitation is placed on the relative change in cellular activity caused by the biologically active substance, providing the change is desirable and useful. Other biologically active materials herein improve diagnostic capability without necessarily altering the structure or activity of the tissue, organ, bone, or cell. These include image contrast enhancing agents for magnetic resonance imaging and x-ray imaging. The cargo material can comprise a metal, including one or more of the above-described restricted metals.

The cargo material can be bound covalently or non-covalently (e.g., by hydrophobic or ionic interactions) to the star polymer. The cargo material does not have to be released from the loaded star polymer in order to perform a useful function. The cargo material can perform a useful function while bound to the star polymer or after release from the star polymer.

The star polymers are nanostructures represented by the general formula (1):

wherein the wavy line represents the crosslinked microgel core, and each T' is an independent polymer arm covalently linked to the microgel core. The star polymer comprises w' polymer arms T', wherein w' is greater than or equal to 6. The star polymer has a particle size of 2 nm to 500 nm. Each of the 6 or more polymer arms comprises a hydrophilic polymer chain segment and a hydrophobic polymer chain segment. The polymer arms can independently further comprise an optional side chain polymer (i.e., a polymer pendant to the backbone of the polymer arm, also referred to herein as the second polymer). The polymer arms can independently also comprise a side chain functional group selected from the group consisting of urea groups, carboxylic ester groups, carboxylic acid groups, carboxylic acid salts, latent carboxylic acid groups, quaternary amine groups, tertiary amine groups, secondary amine groups, primary amine groups, azides, alkynes, poly(alkylene ether) groups, and combinations thereof. The 6 or more polymer arms can independently be living polymer arms, and the microgel core can independently be a living microgel core. The polymer arms and the microgel core can independently comprise a homopolymer, random copolymer, block copolymer, or combinations thereof.

The star polymers are biodegradable and have a polydispersity index of 1.35 or less. The star polymers are formed using a polymerization method that involves the use of an organocatalyst rather than a catalyst comprising a structural metal. The star polymer contains no more than 100 ppm of any single restricted metal described above. In an embodiment, the microgel core includes 6 or more sites capable of further synthetic transformation, the sites including a functional group selected from the group consisting of alcohols, amines, carboxylic acids, azides, alkynes, alkenes, halogen groups, and combinations thereof.

Star Polymers Prepared by Vinyl Polymerizations.

Vinyl polymerization methods are well known and include but are not limited to free radical polymerizations, living anionic addition polymerizations, and living free radical polymerizations (e.g., nitroxide mediated radical polymerization (NMP), atom radical transfer Polymerization (ATRP), and reversible addition-fragmentation chain transfer (RAFT)).

Exemplary vinyl monomers include styrene and substituted styrenes, divinylbenzene and substituted divinylbenzenes, (meth)acrylate esters, ethylene glycol di(meth)acrylates, (meth)acrylamides, acrylonitrile, vinyl acetate, vinyl chloride, ethene, propene, and butadiene. Other vinyl monomers will be readily apparent to those skilled in the polymer art.

ATRP polymerizations are typically initiated by an alkyl halide and catalyzed by a transition metal. The reaction is illustrated in Scheme 1 with the polymerization of styrene using copper(I) bromide as the catalyst, ethyl 2-bromo-2-methylpropionate as the initiator, and N,N,N',N,N pentamethyldiethylenetriamine (PMDETA) as a stabilizing ligand.

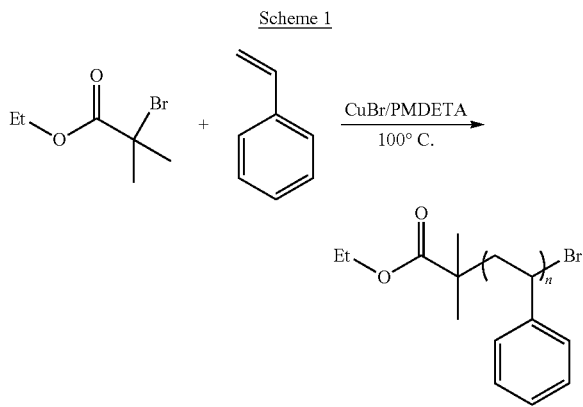

Scheme 1

ATRP produces polymers having narrow molecular distributions, but the metal catalyst can be cytotoxic and difficult to remove. Common monomers for ATRP include (meth)acrylates, (meth)acrylamides, acrylonitrile, and styrenes.

Anionic addition polymerizations of vinyl monomers (e.g., styrene, propene, butadiene), are typically initiated by nucleophilic alkyllithium compounds, Grignard reagents, metal alkoxides and metal hydroxides. The resulting anionic living polymers generally have low polydispersities but are non-biodegradable.

In general, star polymers prepared from vinyl monomers are less preferred due to one or more of the following drawbacks: i) the polymerizations require a metal-containing polymerization catalyst which contaminates the star polymer product with residual Group 3 to Group 12 metal; ii) the star polymers are less than biodegradable as defined by the ASTM D6400 standard, and/or iii) the star polymers have a polydispersity index greater than 1.35.

Star Polymers Prepared by Ring Opening Polymerization.

The star polymers are preferably derived by ring opening polymerization of one or more cyclic carbonyl monomers using organocatalysis to form the polymer arms and the microgel cores. The organocatalyst comprises no structural metal that is a restricted metal. The term "structural metal" refers to metal that is an essential component of the chemical formula of the polymerization catalyst, and includes ionic and non-ionic forms of the structural metal. The star polymers produced using an organocatalyst by ROP methods contain no more than 100 ppm of any single restricted metal. Moreover, the star polymers formed by organocatalyzed ring opening polymerizations of cyclic carbonyl monomers have been found to have narrower molecular weight distributions (i.e., lower polydispersity indexes) compared to star polymers formed by ring opening polymerization with a polymerization catalyst comprising a structural metal. The molecular weight distributions are also narrower than star polymers prepared by free radical polymerizations (FRP). The star polymers formed by ring opening polymerization are biodegradable, and they can be more biocompatible materials (i.e., non-immunogenic, non-cytotoxic material) due to lower levels of metal contaminants arising from a polymerization catalyst. In addition, sequential ROP polymerizations can be conducted in some instances in a single vessel.

In one process, the polymer arms are prepared first, followed by the core, wherein the formation of the crosslinked core conjoins six or more of the amphiphilic polymer arms. In an embodiment, a polymer arm T' has the general formula (2):

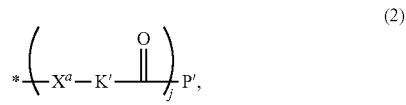

(2)

wherein the asterisk on the left of $X^a$ indicates the attachment point, or bond, to the microgel core. Each P' is a monovalent radical representing a peripheral hydrophilic polymer chain segment of the polymer arm, and is derived from a first polymer. The first polymer can be prepared by ring opening polymerization or by another type of polymerization. P' can further comprise a substituent group selected from the group consisting of urea groups, carboxylic acid groups, carboxylic acid salts, latent carboxylic acid groups, quaternary amine groups, tertiary amine groups, secondary amine groups, primary amine groups, azides, alkynes, poly(alkylene ether) groups, and combinations thereof. In formula (2), the moiety

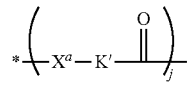

is a divalent radical comprising the hydrophobic chain segment of the polymer arm, and is derived by ring opening polymerization of one or more cyclic carbonyl monomers. The dash on the right side of the carbonyl represents the bond to P'. Each $X^a$ is a divalent radical independently selected from the group consisting of —O—, —NH—,

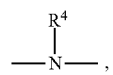

and —S—, wherein $R^4$ is a monovalent radical comprising 1 to 30 carbons. K' is a divalent radical comprising 1 to 10 backbone carbons linking $X^a$ to the carbonyl group. Each j is independently an integer greater than 1, more particularly greater than or equal to 4, and even more particularly greater than or equal to 10. Subscript j is chosen so as to achieve the desired hydrophobic/hydrophilic balance in the polymer arm, which depends on the backbone type of hydrophilic chain segment, the average molecular weight of the hydrophilic chain segment, and the cyclic carbonyl monomer or monomers used to prepare the hydrophobic chain segment. K' can further comprise a functional side chain group F'. The hydrophobic chain segment comprises a backbone selected from the group consisting of polyesters, polycarbonates, polyureas, polycarbamates, polythiocarbamates, polydithiocarbamates, and combinations thereof, which have a repeat structure as shown in (Table 1):

TABLE 1

| Polyester | 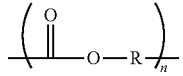 |
| Polycarbonate |  |
| Polyurea | 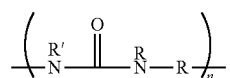 |
| Polycarbamate | 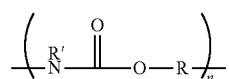 |
| Polythiocarbamate | 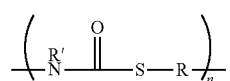 |
| Polythiocarbonate | 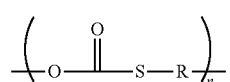 |
| Polydithiocarbonate | 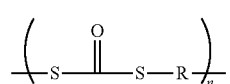 |

More particularly, a polymer arm has the general formula (3):

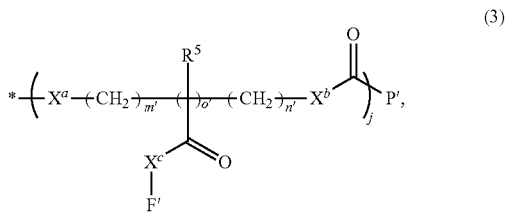

(3)

wherein $X^a$, j, and P' are defined as above. $X^b$ and $X^c$ are each divalent radicals independently selected from the group consisting of —O—,

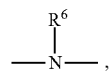

—NH—, and —S—, wherein each $R^6$ is independently hydrogen or a monovalent hydrocarbon radical comprising 1 to 30 carbons. Each $R^5$ is independently hydrogen or a monovalent hydrocarbon radical comprising 1 to 30 carbons. Each m' and n' is independently zero or an integer from 1 to 5. Each o' is independently zero or an integer from 1 to 3. Each functional group F' is independently a monovalent radical comprising from 0 to 10000 carbons. Subscripts m', n', and o' together cannot be zero within the same repeat unit. Each functional group F' can independently comprise a non-polymeric group or a polymeric group, referred to herein as an optional second polymer. The optional second polymer can be derived by ring opening polymerization or another type of polymerization.

In one embodiment, each $X^a$ and each $X^b$ is oxygen, m' and n' are each independently an integer from 1 to 3, and o' is zero or 1. In another embodiment, $X^c$ is oxygen, and F' is methyl or ethyl. In another embodiment, F' comprises a second polymer. In still another embodiment, the second polymer comprises a polyether chain. In another embodiment, P' comprises a polymer backbone selected from the group consisting of polyester, polycarbonate, and combinations thereof.

Scheme 2 illustrates the preparation of a biodegradable amphiphilic star polymer by ring opening polymerization, wherein a Polymer Arm Precursor is prepared first, followed by the Microgel Core.

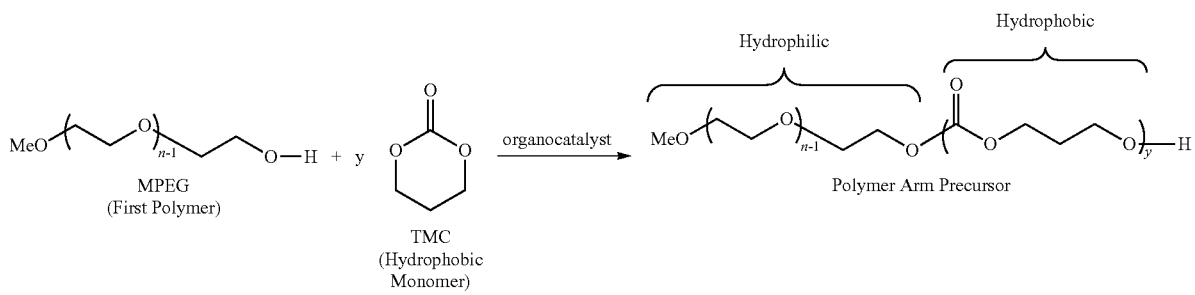

Scheme 2.

-continued

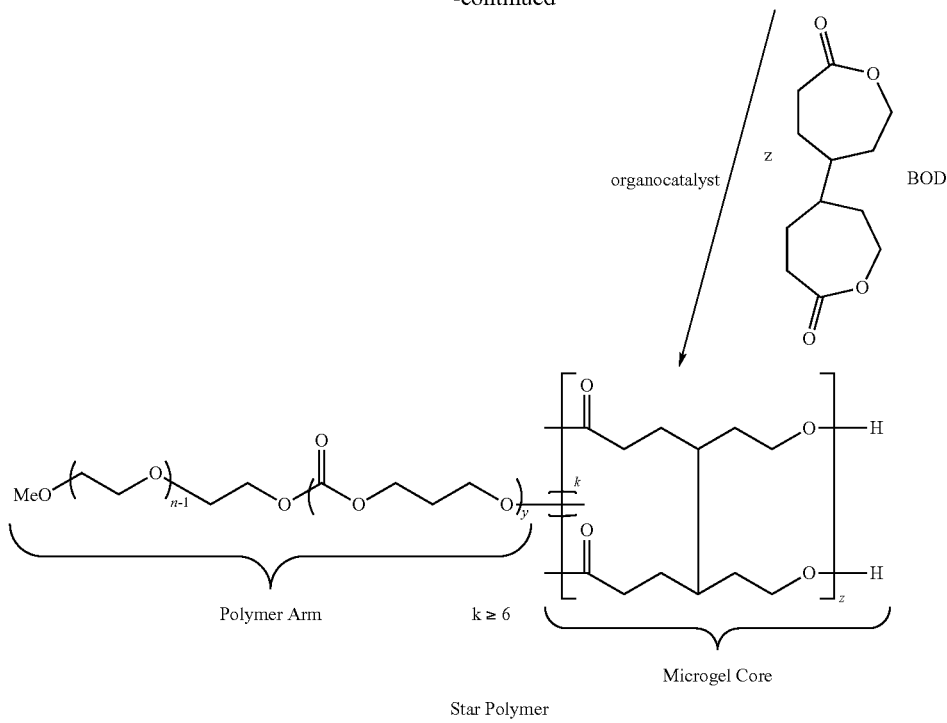

Star Polymer

In this example mono methyl end capped poly(ethylene glycol) (First Polymer, MPEG) initiates polymerization of trimethylene carbonate (TMC) in the presence of a suitable organocatalyst, thereby producing the Polymer Arm Precursor. In this instance, the Polymer Arm Precursor is a living block copolymer comprising a hydrophobic polycarbonate backbone segment derived from TMC. This segment has a terminal hydroxyl group capable of initiating a ring opening polymerization. The ring opening polymerization of BOD initiated by the Polymer Arm Precursor produces the Microgel Core, conjoining six or more of the Polymer Arm Precursors, thereby forming the Star Polymer. In this instance, the Microgel Core is a highly crosslinked living network comprising a polyester repeat structure, and further comprising six or more sites (terminal hydroxy groups) for further functionalization or ring opening polymerization if desired. The subscripts y and z indicate the relative moles of monomer used to make the Star Polymer. The subscript k is an integer greater than or equal to 6 and represents the number of Polymer Arms in the Star Polymer.

Thus, a method (Method 1) of preparing a polymer arm precursor comprises agitating a mixture comprising a first polymer, a first cyclic carbonyl monomer, an organocatalyst comprising no structural metal, an optional accelerator, and an optional solvent, thereby forming the polymer arm precursor by ring opening polymerization of the cyclic carbonyl monomer. The polymer arm precursor is a living polymer and comprises a hydrophilic chain segment, a hydrophobic chain segment, and an initiator group for ring opening polymerization. Herein, the polymer arm precursor is also referred to as a polymeric initiator for ring opening polymerization of a core precursor material.

In a method (Method 2) of forming a star polymer, which can involve one or more of the above-described polymerization techniques, a mixture comprises: i) a polymer arm precursor comprising an initiator group for polymerization, the arm precursor also comprising a hydrophobic polymer chain segment and a hydrophilic polymer chain segment, ii) a core precursor material comprising two or more polymerizable groups, iii) an organocatalyst, iv) an optional accelerator, and v) an optional solvent. The mixture is agitated, thereby forming an amphiphilic star polymer by polymerization of the core precursor material; wherein the star polymer comprises a crosslinked living microgel core derived from the core precursor material, the star polymer comprises 6 or more independent polymer arms covalently linked to the core, the 6 or more polymer arms being derived from the polymer arm precursor, and the star polymer contains no more than 100 ppm of any single restricted metal. In an embodiment, the core precursor material comprises two or more polymerizable cyclic carbonyl groups, and the microgel core is formed by ring opening polymerization of the two or more cyclic carbonyl groups. In an embodiment, each of the 6 or more polymer arms comprises a peripheral hydrophilic chain segment, and a hydrophobic chain segment located nearest the microgel core. In another embodiment, each of the 6 or more polymer arms comprises a peripheral hydrophobic chain segment, and a hydrophilic chain segment located nearest the microgel core. In another embodiment, the polymeric initiator comprises a backbone segment derived by ring opening polymerization of one or more cyclic carbonyl monomers. In another embodiment, the polymeric initiator comprises a backbone segment comprising a poly(alkylene ether). In another embodiment, the organocatalyst comprises a nitrogen base comprising three or more nitrogens.

As shown above in Scheme 1, the polymer arm precursor is a free polymer chain as opposed to the 6 or more polymer arms of the star polymer, which are covalently linked to the microgel core. Initiation of ring opening polymerization of the core precursor material by the polymer arm precursors causes the polymer arm precursors to be conjoined by the growing crosslinked microgel network. The core precursor material and the cyclic carbonyl monomer can each comprise a functional group selected from the group consisting of cyclic esters, cyclic carbonates, cyclic ureas, cyclic carbamates, cyclic thiocarbonates, cyclic thioureas, cyclic dithiocarbonates, and combinations thereof. In an embodiment, the core precursor material and the cyclic carbonyl monomer each comprise a functional group selected from the group consisting of cyclic esters, cyclic carbonates, and combinations thereof. In another embodiment, the first polymer is a mono end capped poly(alkylene glycol). In another embodiment, the method is performed in a single reaction vessel without isolating the polymer arm precursor.

In another method (Method 3) of preparing a biodegradable amphiphilic star polymer, the polymer arms are completed after formation of the microgel core. The method comprises agitating a first mixture comprising a first polymer comprising a protected functional group and an non-protected initiator group, a core precursor material comprising two or more polymerizable groups, an organocatalyst, an optional accelerator, and an optional solvent, thereby forming a protected first star polymer by polymerization of the core precursor material. The protected star polymer comprises a crosslinked microgel core and 6 or more independent first polymer arms comprising a protected functional group. The protected functional group of each of the 6 or more first polymer arms is then deprotected, thereby forming a second star polymer comprising 6 or more independent second polymer arms. The deprotected functional group of the 6 or more independent second polymer arms can be an initiator group suitable for extending the second polymer arms by polymerization. Alternatively, the deprotected functional group can be converted to an active leaving group useful in extending the second polymer arms, for example by a nucleophilic displacement reaction. The resulting star polymer comprises 6 or more independent polymer arms covalently bound to the microgel core, the polymer arms comprising a hydrophobic polymer chain segment and a hydrophilic polymer chain segment.

The protected functional group of the first polymer arms can be in the form of a protected alcohol, protected amine, or protected thiol group, which when deprotected forms an alcohol, amine, or thiol, respectively. The deprotected initiator group is preferably in the terminal subunit of each of the 6 or more deprotected second polymer arms.

Figure 2A:
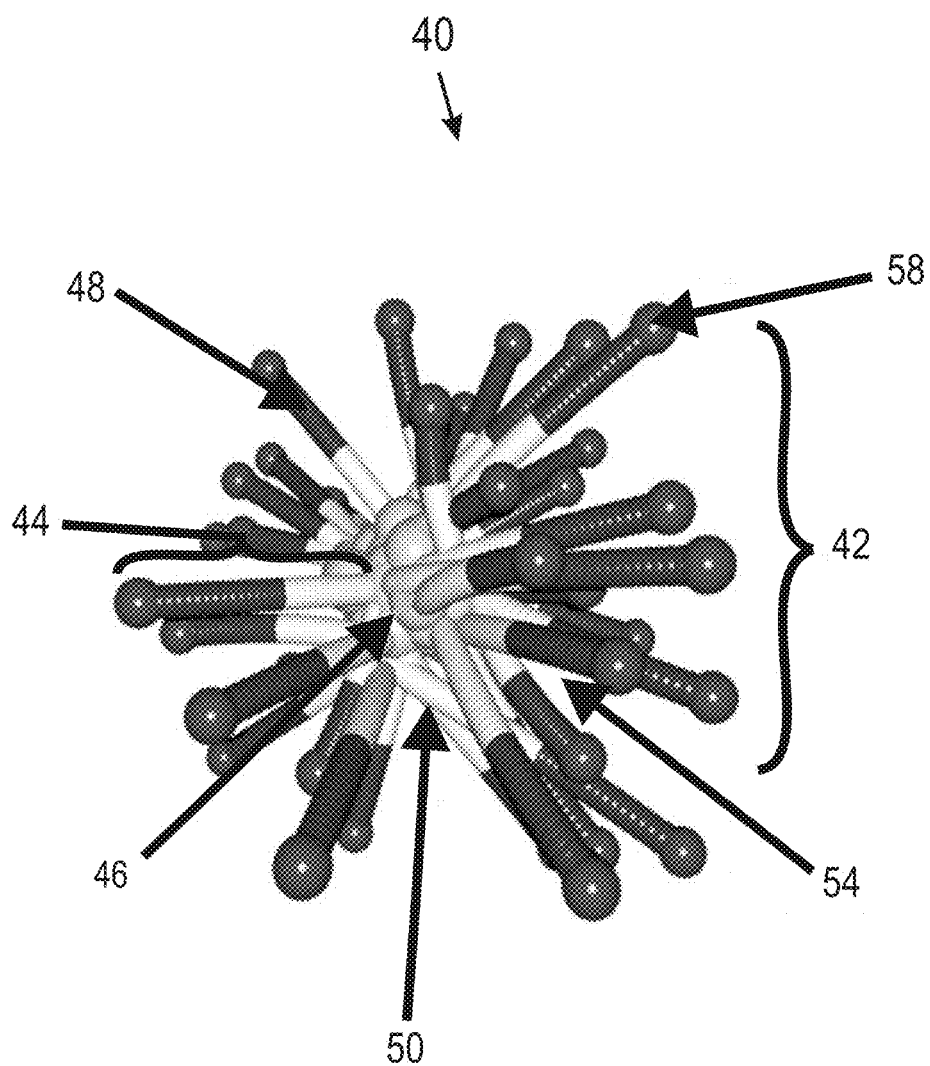
FIG. 2A is a 3-dimensional molecular model of an amphiphilic star polymer having a hydrophobic peripheral segment of the polymer arm and a hydrophilic inner segment.
Figure 2B:
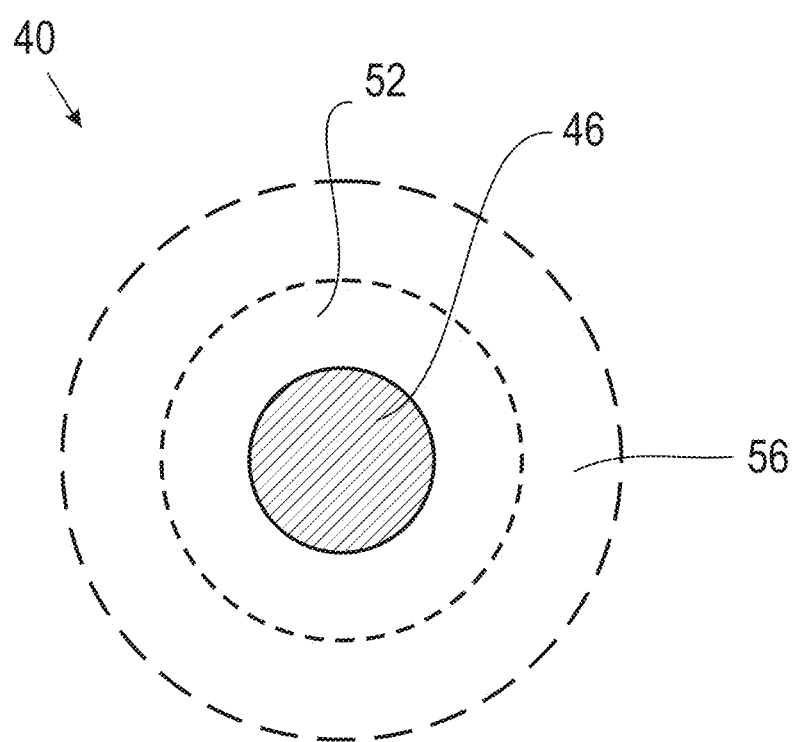
FIG. 2B is a cross-sectional view of a layer diagram of an amphiphilic star polymer of FIG. 2A depicting the core shell structure, wherein the shell comprises an hydrophobic peripheral shell and a hydrophilic inner shell.

Using the above-described methods, the hydrophilic chain segment of a polymer arm can be located at a peripheral end of each of the 6 or more polymer arms, as illustrated in FIG. 1A. Alternatively, the hydrophobic chain segment can be located at the peripheral end of each of the 6 or more polymer arms. This is illustrated in the molecular models of FIG. 2A and FIG. 2B, wherein star polymer 40 comprises a shell 42 composed of six or more independent amphiphilic polymer arms 44, each of which is covalently linked to a central microgel core 46. A polymer arm comprises a peripheral hydrophobic chain segment 48 and an inner hydrophilic chain segment 50. Shell 42 has two regions, a hydrophobic outer shell region 56 (FIG. 2B) comprising peripheral hydrophobic chain segments 48 and interstitial region 54 (FIG. 2A), and a hydrophilic inner shell region 52 composed of the hydrophlic inner chain segments 50 and interstitial region 54. The dashed boundary lines around inner shell region 52 and outer shell region 56 in FIG. 2B indicate the interstitial area is shared by the outer and inner shell regions. The microgel core 46 can be either hydrophobic or hydrophilic. The outer shell region 56, the inner shell region 52, and/or the microgel core 46 can further contain specific sites useful in controlling chemical interactions that favor the binding of, or the release of, a biologically active cargo material. For example, the microgel core 46 can be a living core, capable of initiating a polymerization or undergoing a different chemical modification. As another non-limiting example, the polymer arms 44 can comprise a functionally useful end group 58, such as a galactose moiety capable of selective recognition of liver cells.

A more specific method (Method 4) of preparing a polymer arm precursor comprises agitating a reaction mixture comprising one or more hydrophobic cyclic carbonyl monomers, a hydrophilic first polymer comprising a ROP initiator group, an organocatalyst comprising no structural metal, an optional accelerator, and an optional solvent, thereby forming a polymer arm precursor by ring opening polymerization. The polymer arm precursor is a living polymer, comprising an initiator group for ring opening polymerization. The polymer arm precursor comprises a hydrophobic chain segment derived from the one or more hydrophobic cyclic carbonyl monomers, and a hydrophilic chain segment derived from the first polymer. In an embodiment, the first polymer is a mono-end capped poly(alkylene glycol). In another embodiment, the first polymer is a poly(alkylene ether) comprising a protected amine end group and a non-protected hydroxyl end group, the hydroxyl group an initiator group for ring opening polymerization. In another embodiment, the first polymer comprises a mono end capped poly(ethylene glycol) or a mono end capped polypropylene glycol).

The polymer arm precursor can be chemically modified to introduce additional functionality after the ring opening polymerization. For example, the reaction mixture can comprise one or more latent hydrophobic cyclic carbonyl monomers; that is, a cyclic carbonyl monomer from which a hydrophobic repeat unit can be derived by a chemical transformation after the ring opening polymerization. Similarly, a latent hydrophilic cyclic carbonyl monomer is one from which a hydrophilic repeat unit can be derived by a chemical transformation after the ring opening polymerization.

In another method (Method 5) of preparing a polymer arm precursor, the hydrophilic and hydrophobic chain segments of the polymer arm precursor are each derived by a ring opening polymerization. The method comprises agitating a first mixture comprising one or more hydrophilic cyclic carbonyl monomers, an organocatalyst comprising no structural metal, an optional accelerator, and an initiator, thereby forming a first polymer by ring opening polymerization, wherein the first polymer comprises an initiator group for ring opening polymerization. A second mixture is formed comprising the first polymer, one or more hydrophobic cyclic carbonyl monomers, an optional second organocatalyst comprising no structural metal, an optional second accelerator, and an optional second solvent. The mixture is agitated, thereby forming a polymer arm precursor, wherein the polymer arm precursor comprises a hydrophobic chain segment derived from the one or more hydrophobic cyclic carbonyl monomers, and a hydrophilic chain segment derived from the first polymer. The first mixture can include one or more latent hydrophilic cyclic carbonyl monomers, and the second mixture can include one or more latent hydrophobic cyclic carbonyl monomers. The polymerizations can be performed in reverse order.

When the hydrophilic chain segment and the hydrophobic chain segment are each formed by a ring opening polymerization, the hydrophilic chain segment and the hydrophobic chain segment can comprise repeat units derived from the same or different cyclic carbonyl monomers. The hydrophilic chain segment and the hydrophobic chain segment can independently comprise a backbone segment selected from the group consisting of polycarbonates, polyesters, polyureas, polycarbamates, polythiocarbamates, polythiocarbonates, polydithiocarbonates, and combinations thereof.

The side chain groups and/or the end unit of the polymer arm or the polymer arm precursor can be further chemically functionalized after formation in order to control, for example, hydrophilic/hydrophobic balance, water dispersibility, cell membrane recognition properties, binding properties with respect to a given cargo material, and/or release properties for a given cargo material.

The polymer arm, the polymer arm precursor, and the optional second polymer can independently comprise an optional end cap group (ECG). End cap groups can impart stability and useful functionality to the final structure. End capping agents are numerous, and methods of their use are well established in the polymer art. End capping agents can be selected based on the functionality desired and their intended use. In an embodiment, the optional end cap group comprises a moiety selected from the group consisting of alkyl ester groups, aryl ester groups, poly(alkylene ether) groups, thiol groups, amine groups, carboxylic acid groups, quaternary amine groups, functional groups capable of targeting specific cell types, and combinations thereof. In an embodiment, the polymer arm comprises a peripheral end group comprising a galactose moiety for targeting liver cells. In another embodiment, the peripheral end group comprises a mannose moiety for binding mannose-specific proteins. In another embodiment, the peripheral end group comprises a quaternary amine.

The core precursor material for the ring opening polymerization can be a monomer, oligomer or a polymer comprising two or more polymerizable cyclic carbonyl moieties. More specifically, the core precursor material comprises two or more functional groups selected from the group consisting of cyclic esters, cyclic carbonates, cyclic carbamates, cyclic ureas, cyclic thiocarbamates, cyclic dithiocarbonates, and combinations thereof. Non-limiting examples of core precursor materials include bis-cyclic esters, bis-cyclic carbonates, bis-cyclic carbamates, bis-cyclic ureas, bis-cyclic thiocarbamates, and bis-cyclic dithiocarbonates. Exemplary bis-cyclic esters include but are not limited to:

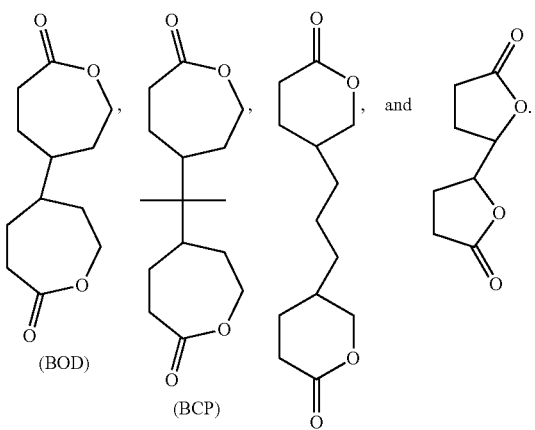

For simplicity, all examples herein assume the ideal case that all initiating groups react and, therefore, the length of polymeric blocks may be described by the division of the number of moles of monomer units (e.g., x, y, z . . . etc.) by the number of moles of initiating sites. However, the reaction of 100% of the initiating sites is not a requirement for successful implementation of the invention. Non-reacted nucleophilic initiating groups can serve as additional reaction or initiator sites during subsequent synthetic processes. Therefore, it is advantageous that a high percentage of the nucleophilic initiating groups undergo the ring opening reaction.

The above reaction illustrated in Scheme 2 is not meant to be restrictive. For example, the reaction of TMC can be followed by a sequential ring opening polymerization of a different hydrophobic cyclic carbonyl monomer, thereby forming a hydrophobic chain comprising a block copolymer derived from one or more hydrophobic cyclic carbonyl monomers. As stated above, the end cap group of the first polymer and/or the hydrophilic chain segment is optional. In addition, the hydrophilic chain segment or the hydrophobic chain segment can comprise a functional group selected from the group consisting of urea groups, carboxylic acid groups, carboxylic acid salts, latent carboxylic acid groups, quaternary amine groups, tertiary amine groups, secondary amine groups, primary amine groups, azides, alkynes, poly(alkylene ether) groups, and combinations thereof, with the proviso that the water dispersibility and carrier properties of the star polymer are not adversely affected.

Polyethers.

A polyether chain can provide an important means of introducing hydrophilicity into the star polymer. As stated above, a mono end capped polyether alcohol (e.g., poly(alkylene glycol) can be employed as an initiator for ring opening polymerization of a cyclic carbonyl monomer, thereby introducing a main chain hydrophilic block into the resulting polymer arm precursor.

The polyether alcohol can be a poly(alkylene glycol) of the general formula (5):

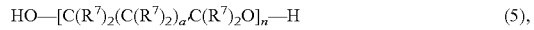

wherein a' is 0 to 8, n is an integer from 2 to 10000, and each $R^7$ is independently a monovalent radical consisting of hydrogen and an alkyl group of 1 to 30 carbons. Thus, the ether repeat unit comprises 2 to 10 backbone carbons between each backbone oxygen. More particularly, the poly(alkylene glycol) can be a mono endcapped poly(alkylene glycol), represented by the formula (6):

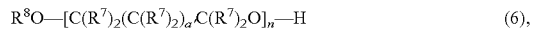

wherein $R^8$ is a monovalent hydrocarbon radical comprising 1 to 20 carbons.

As non-limiting examples, the polyether alcohol can be a poly(ethylene glycol) (PEG), having the structure HO—[$CH_2CH_2O$]$_n$—H, wherein the ether repeat unit $CH_2CH_2O$ (shown in the brackets) comprises two backbone carbons linked to a backbone oxygen. The polyether alcohol can also be a poly(propylene glycol) (PPG) having the structure HO—[$CH_2CH(CH_3)O$]$_n$—H, where the ether repeat unit $CH_2CH(CH_3)O$ comprises two backbone carbons linked to a backbone oxygen with a methyl side-chain. An example of mono end capped PEG is the commercially available monomethyl end capped PEG, wherein $R^8$ is a methyl group. Other examples include poly(oxetane), having the structure HO—[$CH_2CH_2CH_2O$]$_n$—H, and poly(tetrahydrofuran), having the structure HO—[$CH_2(CH_2)_2CH_2O$]$_n$—H The mono end capped poly(alkylene glycol) can comprise more elaborate chemical structures, represented by the general formula (7):

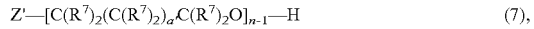

wherein Z' is a monovalent radical including the backbone carbons and oxygen of the end repeat unit, and can have 2 to 100 carbons. The following non-limiting examples illustrate mono end-derivatization of poly(ethylene glycol) (PEG). As described above, one end repeat unit of PEG can be capped with a monovalent hydrocarbon group having 1 to 20 carbons, such as the monomethyl PEG (MPEG), wherein Z' is MeOCH$_2$CH$_2$O— as shown further above for MPEG in Scheme 2. The dash on the end of the MeOCH$_2$CH$_2$O— indicates the point of attachment to the polyether chain. In another example, Z' includes a thiol group, such as HSCH$_2$CH$_2$O—, or a thioether group, such as MeSCH$_2$CH$_2$O—. In another example, one end unit of PEG is an aldyhyde, wherein Z' can be OCHCH$_2$CH$_2$O—. Treating the aldehyde with a primary amine produces an imine, wherein Z' is R$^9$N=CHCH$_2$CH$_2$O—. R$^9$ is a monovalent radical selected from hydrogen, an alkyl group of 1 to 30 carbons, or an aryl group comprising 6 to 100 carbons. Continuing, the imine can be reduced to an amine, wherein Z' is R$^9$NHCH$_2$CH$_2$CH$_2$O—. In another example, one end repeat unit of PEG can be oxidized to a carboxylic acid, wherein Z' is HOOCCH$_2$O—. Using known methods the carboxylic acid can be converted to an ester, wherein Z' becomes R$^9$OOCCH$_2$O—. Alternatively, the carboxylic acid can be converted to an amide, wherein Z' becomes R$^9$NHOCCH$_2$O—. Many other derivatives are possible. In a particular embodiment, Z' is a group comprising a biologically active moiety that interacts with a specific cell type. For example, the Z' group can comprise a galactose moiety which specifically recognizes liver cells. In this instance, Z' has the structure:

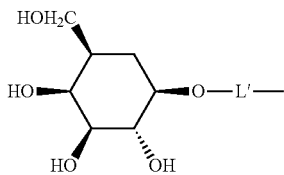

where L' is a divalent linking group comprising 2 to 50 carbons containing the end repeat unit. The hyphen on the right side of L' indicates the attachment point to the polyether chain. Z' can comprise other biologically active moieties such as mannose.

A polyether alcohol employed as an initiator for a ring opening polymerization can comprise a poly(alkylene glycol) or a mono-derivatized poly(alkylene glycol). The number average molecular weight of the polyether alcohol can be from 100 to 100,000, more specifically 100 to 10000, and even more specifically, 100 to 5000.

Cyclic Carbonyl Monomers.

The cyclic carbonyl monomers can have the general formula (8):

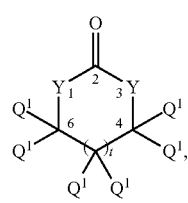

(8)

wherein t is an integer from 0 to 6, and when t is 0 carbons labeled 4 and 6 are linked together by a single bond. Each Y is a divalent radical independently selected from the group consisting of —O—, —S—,

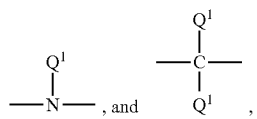

wherein the dashes "-" indicate the point of group attachment in the ring. The latter two groups are expressed herein as —N(Q$^1$)- and —C(Q$^1$)$_2$-. Each Q$^1$ is an independent monovalent radical. Each Q$^1$ group can independently be branched or non-branched. Each Q$^1$ group can independently comprise a polymer comprising from 1 to 10000 carbons. A Q$^1$ group can have the structure

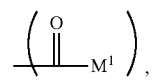

wherein the dash on the left side of the carbonyl indicates the point of attachment, M$^1$ is a monovalent radical, polymeric or non-polymeric. As examples, each M$^1$ can independently be selected from the group consisting of —R$^1$, —OR$^1$, —NHR$^1$, —NR$^1$R$^1$, and —SR$^1$ wherein the dash represents the point of attachment, and each R$^1$ is an independent polymeric or non-polymeric monovalent radical. In this example, each R$^1$ can independently be selected from the group consisting of alkyl groups comprising 1 to 100 carbons, and aryl groups comprising 6 to 100 carbons. Each Q$^1$ group can independently comprise one or more additional functional groups selected from the group consisting of ketone groups, aldehyde groups, alkene groups, alkyne groups, cycloaliphatic rings comprising 3 to 10 carbons, heterocylic rings comprising 2 to 10 carbons, ether groups, amide groups, ester groups, carboxylic acid groups, urea groups, and combinations of the foregoing additional functional groups. The heterocyclic ring can comprise oxygen, sulfur and/or nitrogen. Two or more Q$^1$ groups can together form a ring. In an embodiment, one or more of the Q$^1$ groups comprises a monovalent urea radical. In another embodiment, one or more of the Q$^1$ groups comprise a latent carboxylic acid group capable of being converted to a carboxylic acid after ring-opening polymerization. In another embodiment, one or more of the Q$^1$ groups comprises a functional group capable of reacting with a tertiary amine to form a quaternary amine. In an embodiment, each Q$^1$ is independently selected from the group consisting of hydrogen, alkyl groups comprising 1 to 100 carbons, and aryl groups comprising 6 to 100 carbons. In another embodiment, at least one Q$^1$ group is a group other than hydrogen.

A more specific cyclic carbonyl monomer has the general formula (9):

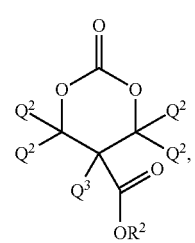

(9)

wherein each Q$^2$ and Q$^3$ is an independent monovalent radical and R$^2$ is a monovalent radical, polymeric or non-polymeric.

As examples, each $Q^2$ and $Q^3$ can independently be selected from the group consisting of hydrogen, halides, alkyl groups having 1 to 100 carbons, and aryl groups having 6 to 100 carbons. When $Q^2$ and $Q^3$ are not hydrogen, $Q^2$ and $Q^3$ represent pendant moieties to the cyclic carbonyl ring that become side chains to the ROP polymer chain. The —$CO_2R^2$ group also becomes a side chain to the ROP polymer after ring opening polymerization. In an embodiment, each $Q^2$ is hydrogen and $Q^3$ is a methyl or ethyl group. In an embodiment, $R^2$ comprises a monovalent urea radical. In another embodiment, $R^2$ comprises a latent carboxylic acid group capable of being converted to a carboxylic acid after ring-opening polymerization. In another embodiment, $R^2$ comprises a functional group capable of reacting with a tertiary amine to form a quaternary amine. In yet another embodiment, $R^2$ comprises a second polymer comprising from 1 to 10000 carbons.

Another more specific cyclic carbonyl monomer has the general formula (10):

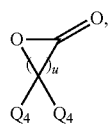

(10)

wherein each $Q^4$ is an independent monovalent radical, and u is an integer from 1 to 8. As examples, each $Q^4$ can independently be selected from the group consisting of hydrogen, halides, alkyl groups comprising 1 to 100 carbons, aryl groups comprising 6 to 100 carbon atoms, and groups having the structure

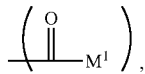

wherein $M^1$ is a monovalent radical, polymeric or non-polymeric. As examples, $M^1$ can be selected from the group consisting of —$R^1$, —$OR^1$, —$NHR^1$, —$NR^1R^1$, and —$SR^1$ wherein the dash represents the point of attachment, and $R^1$ is a monovalent radical, polymeric or non-polymeric. As examples, each $R^1$ can independently be selected from the group consisting of alkyl groups comprising 1 to 100 carbons, and aryl groups comprising 6 to 100 carbons. When $Q^4$ is not hydrogen, $Q^4$ represents a pendant moiety to the cyclic carbonyl ring that becomes a side chain to the ROP polymer after ring opening polymerization. The lactone ring can optionally comprise a carbon-carbon double bond; that is, optionally, a

group of formula (10) can independently represent a

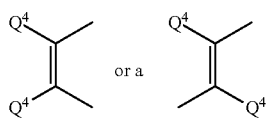

group. The lactone ring can also comprise a heteroatom not linked to the ring carbonyl or ring oxygen, such as oxygen, nitrogen, sulfur, or a combination thereof; that is, optionally a

group of formula (10) can independently represent a —O—, —S—, or —$NR^1$— group. In an embodiment, u is an integer from 1 to 6 and each $Q^4$ is hydrogen. In an embodiment, one or more of the $Q^4$ groups comprises a monovalent urea radical. In another embodiment, one or more of the $Q^4$ groups comprise a latent carboxylic acid group capable of being converted to a carboxylic acid after ring opening polymerization. In another embodiment, one or more of the $Q^4$ groups comprises a functional group capable of reacting with a tertiary amine to form a quaternary amine.

The cyclic carbonyl monomer can have the general formula (11):

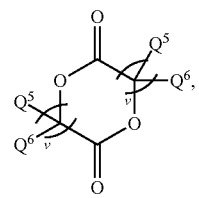

(11)

wherein each $Q^5$ is an independent monovalent radical. As examples, each $Q^5$ can independently be selected from the group consisting of hydrogen, halides, alkyl groups comprising 1 to 100 carbons, aryl groups comprising 6 to 100 carbon atoms, and groups having the structure

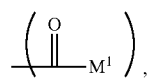

wherein $M^1$ is a monovalent radical, polymeric or non-polymeric, and each v is independently an integer from 1 to 6. As examples, $M^1$ can be selected from the group consisting of —$R^1$, —$OR^1$, —$NHR^1$, —$NR^1R^1$, and —$SR^1$ wherein the dash represents the point of attachment, and $R^1$ is a monovalent radical, polymeric or non-polymeric. As examples, each $R^1$ can independently be selected from the group consisting of alkyl groups comprising 1 to 100 carbons, and aryl groups comprising 6 to 100 carbons. Each $Q^6$ is an independent monovalent radical. As examples, each $Q^6$ can independently be selected from the group consisting of hydrogen, alkyl groups having 1 to 100 carbons, and aryl groups having 6 to 100 carbons. When $Q^5$ and $Q^6$ are not hydrogen, $Q^5$ and $Q^6$ represent pendant moieties to the cyclic carbonyl ring that become side chains to the ROP polymer after ring opening polymerization. In an embodiment, each v is 1, each $Q^5$ is hydrogen, and each $Q^6$ is a hydrocarbon group comprising 1 to 6 carbons. In an embodiment, one or more of the $Q^5$ and/or $Q^6$ groups comprises a monovalent urea radical. In another embodiment, one or more of the $Q^5$ and/or $Q^6$ groups comprises a latent carboxylic acid group capable of being converted to a carboxylic acid after ring-opening polymerization.

In another embodiment, one or more of the $Q^5$ and/or $Q^6$ groups comprises a functional group capable of reacting with a tertiary amine to form a quaternary amine.

In an embodiment, the polymer arm comprises repeat units derived from a cyclic carbonyl monomer of the general formula (12):

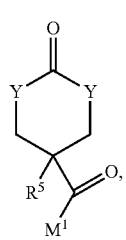

(12)

wherein each Y is independently selected from the group consisting of —O—, —NH—,

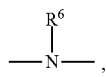

and —S—, $R^5$ and $R^6$ are independent monovalent radicals comprising 1 to 30 carbons, and $M^1$ is selected from the group consisting of —$OR^1$, —$NHR^1$, —$NR^1R^1$, and —$SR^1$ wherein the dash represents the point of attachment, and $R^1$ is a monovalent radical. $M^1$ can comprise a non-polymeric group or a second polymer, wherein the second polymer comprises 1 to 10000 carbons.

The cyclic carbonyl monomer can comprise a latent carboxylic acid. Non-limiting examples of latent carboxylic acids include esters that can be hydrolyzed under mild conditions (e.g., trifluoroethyl ester, pentafluorophenyl ester, or p-nitrophenyl ester, N-hydroxysuccinimimide ester, trimethylsilyl ester, tetrahydropyranyl ester). Other latent carboxylic acids include thermally labile tertiary esters (e.g., t-butyl esters). Still other latent carboxylic acids include esters capable of being reductively cleaved using hydrogen and a suitable catalyst (e.g., benzyl esters, cleavable by $H_2$/Pd—C). In an embodiment, the latent carboxylic acid group is any carboxylic ester that can be converted to a carboxylic acid by hydrogenation using a suitable catalyst. One example is the benzyl ester of MTCOBn.

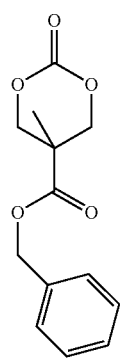

(MTCOBn)

The benzyl ester of MTCOBn can be cleaved to a carboxylic acid using $H_2$/Pd—C after the ring opening polymerization.

Another example of a latent carboxylic acid group is an acetal-protected carboxylic acid group, herein also referred to as an acetal ester group. The acetal ester group has the general formula (13):

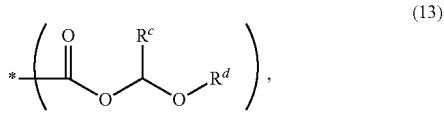

(13)

wherein * represents the site of attachment to a cyclic carbonyl moiety, and $R^c$ and $R^d$ are monovalent radicals independently comprising from 1 to 20 carbons. In an embodiment, $R^c$ is methyl and $R^d$ is ethyl. An example of cyclic carbonyl compound comprising an acetal ester is MTCOEE:

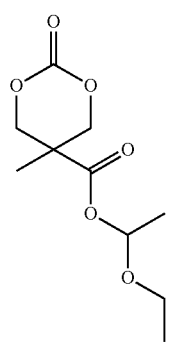

(MTCOEE)

When copolymerized into the polymer, repeat units derived from MTCOEE comprise a side chain acetal ester that is readily deprotected in the acidic endosomal environment. Once released into the cytoplasm, the resulting carboxylic acid groups of the cationic polymer can be deprotonated, Additional cyclic carbonyl monomers of formulas (9), (10), and (11) are listed in Table 2.

TABLE 2

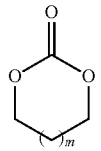

$m = 1$, Trimethylene carbonate (TMC)
$m = 2$, Tetramethylene carbonate (TEMC)
$m = 3$, Pentamethylene carbonate (PMC)

TABLE 2-continued
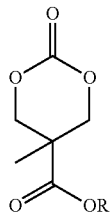
R = hydrogen (MTCOH)
R = methyl (MTCOMe)
R = t-butyl (MTCO$^t$Bu)
R = ethyl (MTCOEt)
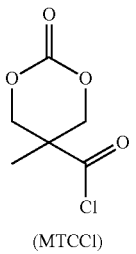
(MTCCl)
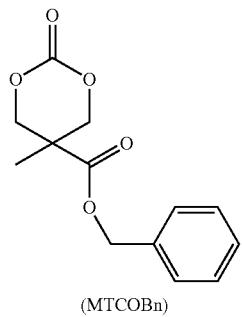
(MTCOBn)
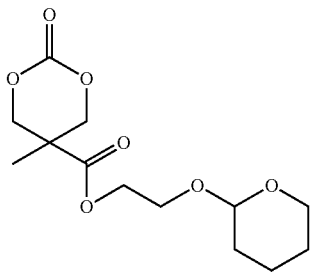 [SMILES: CC1(C(=O)OCCOC2CCCCO2)COC(=O)OC1]
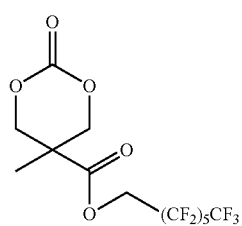
(CF$_2$)$_5$CF$_3$
TABLE 2-continued
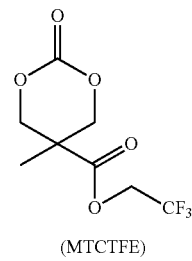 [SMILES: CC1(C(=O)OCC(F)(F)F)COC(=O)OC1]
(MTCTFE)
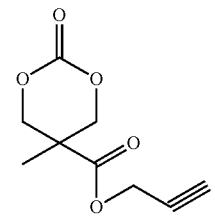
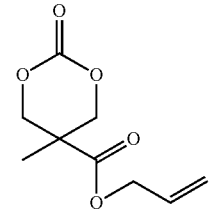
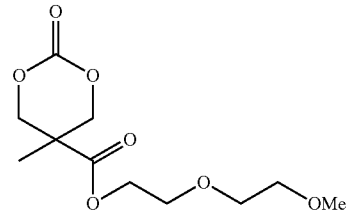 [SMILES: COCCOCCOC(=O)C1(C)COC(=O)OC1]
OMe
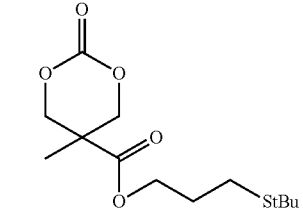
StBu
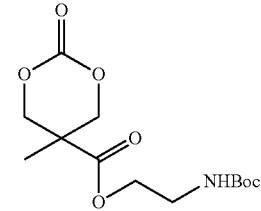 [SMILES: CC(C)(C)OC(=O)NCCOC(=O)C1(C)COC(=O)OC1]
NHBoc
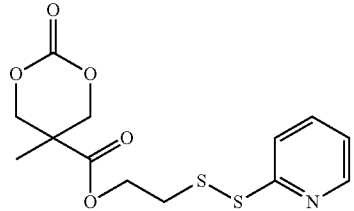 [SMILES: CC1(C(=O)OCCSSc2ccccn2)COC(=O)OC1]

TABLE 2-continued

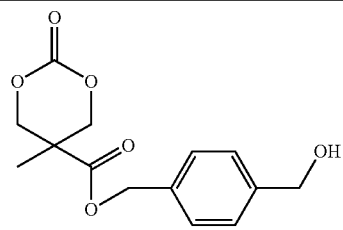

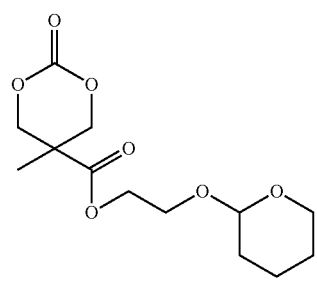 [SMILES: CC1(C(=O)OCCOC2CCCCO2)COC(=O)OC1]

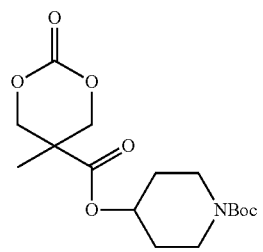 [SMILES: CC(C)(C)OC(=O)N1CCC(OC(=O)C2(C)COC(=O)OC2)CC1]

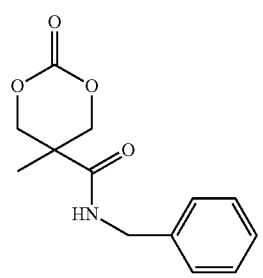 [SMILES: CC1(C(=O)NCc2ccccc2)COC(=O)OC1]

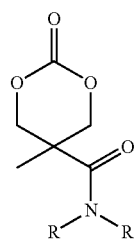

R = methyl
R = iso-propyl

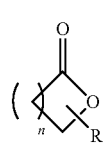

R = H; n = 1: beta-Propiolactone (b-PL)
R = H; n = 2: gamma-Butyrolactone (g-BL)
R = H; n = 3: delta-Valerolactone (d-VL)
R = H; n = 4: epsilon-Caprolactone (e-CL)
R = CH3; n = 1: beta-Butyrolactone (b-BL)
R = CH3; n = 2: gamma-Valerolactone (g-VL)

TABLE 2-continued

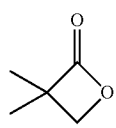

Pivalolactone
(PVL)

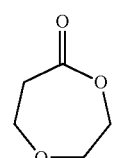

1,5-Dioxepan-2-one
(DXO)

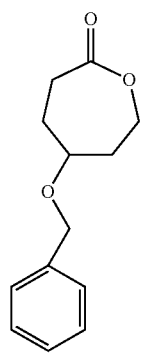

5-(Benzyloxy)oxepan-2-one
(BXO)

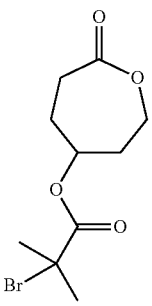

7-Oxooxepan-4-yl 2-bromo-2-
methylpropanoate
(BMP-XO)

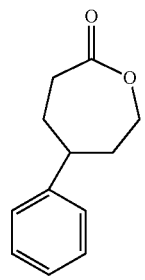

5-Phenyloxepan-2-one
(PXO)

TABLE 2-continued

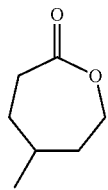

5-Methyloxepan-2-one
(MXO)

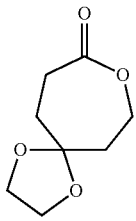

1,4,8-Trioxa(4,6)spiro-9-undecane
(TOSUO)

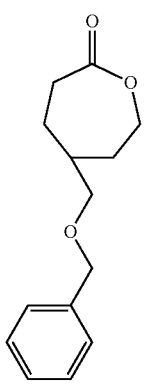

5-(Benzyloxymethyl)oxepan-2-one
(BOMXO)

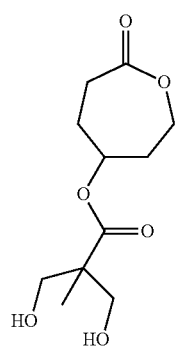

7-Oxooxepan-4-yl 3-hydroxy-2-
(hydroxymethyl)-2-methylpropanoate
(OX-BHMP)

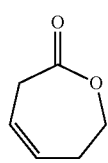

(Z)-6,7-Dihydrooxepin-2(3H)-one
(DHXO)

TABLE 2-continued

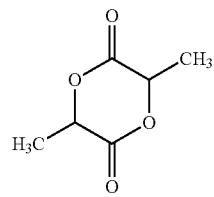

D-Lactide (DLA)
L-Lactide (LLA) or
racemic Lactide, 1:1 D:L forms (DLLA)

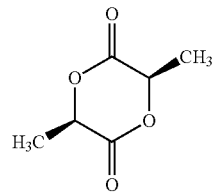

maso-Lactide (MLA)
(two opposite centers of asymmetry
R and S)

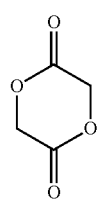

Glycolide
(GLY)

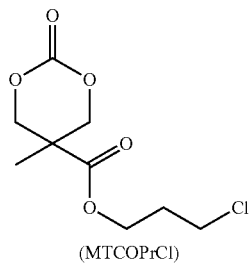

(MTCOPrCl)

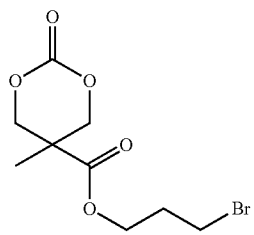

(MTCOPrBr)

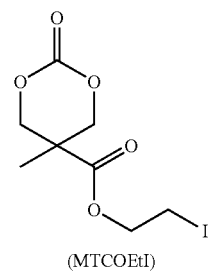

(MTCOEtI)

The cyclic carbonyl monomers can be purified by recrystallization from a solvent such as ethyl acetate or by other known methods of purification, with particular attention being paid to removing as much water as possible from the monomer. The monomer moisture content can be from 1 to 10,000 ppm, 1 to 1,000 ppm, 1 to 500 ppm, and most specifically 1 to 100 ppm, by weight of the monomer.

The cyclic carbonyl monomers can also comprise isotopically enriched forms of the cyclic carbonyl monomers. These include functional groups comprising elements selected from the group consisting of $^{13}C$, $^{14}C$, $^{15}N$, deuterium, tritium, and combinations thereof. The cyclic carbonyl monomers can also comprise a radioactive moiety suitable for targeting a specific cell type, such as a cancer cell.

The cyclic carbonyl monomers can comprise a reactive monovalent leaving group that when treated with a tertiary amine, produces a quaternary amine. Reactive monovalent leaving groups include alkyl halides (e.g., alkyl chlorides, alkyl bromides, or alkyl iodides), sulfonate esters (e.g., tosylates, or mesylates), epoxides, and oxetanes. Reaction with the tertiary amine is generally performed after the ring opening reaction when the reactive monovalent leaving group occupies a side chain position in the ROP polymer.

The tertiary amine can comprise a single nitrogen such as a trialkylamine, including but not limited to trimethylamine, triethylamine, tripropylamine, and the like. The tertiary amine can further comprise additional functional groups, in particular a carboxylic acid group, for example 3-(N,N-dimethylamino)propionic acid. In such instances, the cationic polymer will comprise first repeat units comprising a side chain moiety comprising a quaternary amine and a carboxylic acid group.

The tertiary amine can also comprise isotopically enriched versions of the tertiary amine, such as trimethylamine-$^{14}C$, trimethylamine-$^{15}N$, trimethylamine-$^{15}N$, trimethyl-$^{13}C_3$-amine, trimethyl-$d_9$-amine, and trimethyl-$d_9$-amine-$^{15}N$. The tertiary amine can also comprise a radioactive moiety suitable for targeting a specific cell type, such as a cancer cell.

The tertiary amine can be a bis-tertiary amine of the general formula (14):

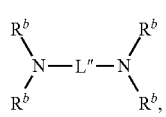

(14)

where L" is a divalent linking group comprising 2 to 30 carbons, and each monovalent $R^b$ group is independently selected from alkyl groups comprising 1 to 30 carbons or aryl groups comprising 6 to 30 carbons. Each $R^b$ group can independently be branched or non-branched. Each $R^b$ group can independently comprise additional functional groups such as a ketone group, aldehyde group, hydroxyl group, alkene group, alkyne group, cycloaliphatic ring comprising 3 to 10 carbons, heterocylic ring comprising 2 to 10 carbons, ether group, amide group, ester group, and combinations of the foregoing additional functional groups. The heterocyclic ring can comprise oxygen, sulfur and/or nitrogen. Two or more $R^b$ groups can also together form a ring. Representative L" groups include —$(CH_2)_{z'}$— where z' is an integer from 2 to 30, —$(CH_2CH_2O)_{z''}CH_2CH_2$— where z" is an integer from 1 to 10, —$CH_2CH_2SCH_2CH_2$—, —$CH_2CH_2SSCH_2CH_2$—, —$CH_2CH_2SOCH_2CH_2$—, and —$CH_2CH_2SO_2CH_2CH_2$—. L" can further comprise a monovalent or divalent cycloaliphatic ring comprising 3 to 20 carbons, a monovalent or divalent aromatic ring comprising 6 to 20 carbons, a ketone group, aldehyde group, hydroxyl group, alkene group, alkyne group, a heterocylic ring comprising 2 to 10 carbons, ether group, amide group, ester group, and combinations of the foregoing functional groups. The heterocyclic ring can comprise oxygen, sulfur and/or nitrogen. The bis-tertiary amine can also comprise isotopically enriched forms of the bis-tertiary amine, such as deuterium, carbon-13, and/or nitrogen-15 enriched forms thereof.

More specific bis-tertiary amines include N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3propanediamine (TEPDA), 1,4-bis(dimethylamino)cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof. In an embodiment, the bis-tertiary amine is TMEDA.

The above-described cyclic carbonyl monomers undergo ring-opening polymerization to form a ROP polymers in atactic, syndiotactic or isotactic forms. The particular tacticity depends on the cyclic monomer(s), isomeric purity, and the reaction conditions.

The reaction mixture for the ring opening polymerization comprises one or more cyclic carbonyl monomers; a catalyst; an optional accelerator; an optional solvent, and an initiator. The ring opening polymerization is generally conducted in a reactor under inert atmosphere such as nitrogen or argon. The polymerization can be performed by solution polymerization in an anhydrous non-protic solvent such as benzene, toluene, xylene, cyclohexane, n-hexane, dioxane, chloroform and dichloroethane, or by bulk polymerization. The reaction temperature can be from about ambient temperature to 250° C. Generally, the reaction mixture is heated at atmospheric pressure for 0.5 to 72 hours to effect polymerization, forming a second mixture.

Exemplary catalysts for ring opening polymerizations include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate and zirconium nitrate.

Structural metal from a polymerization catalyst can be entrapped by the crosslinked microgel core. The trapped metal can be cytotoxic and can interfere with the binding, release and/or the function of a cargo material. Therefore, star polymers comprising a minimum of each restricted metal described further above is highly desirable. Preferred catalysts for the ring opening polymerization are organocatalysts. An organocatalyst overcomes the problem of entrapped metal, in addition to providing a platform for synthesizing ring opened polymers of controlled, predictable molecular weights and narrow polydispersities. Examples of organocatalysts for ring opening polymerization of cyclic esters, cyclic carbonates and siloxanes are 4-dimethylaminopyridine, phosphines, N-heterocyclic carbenes (NHC), bifunctional aminothioureas, phosphazenes, amidines, and guanidines. In an embodiment the catalyst is N-(3,5-trifluoromethyl)phenyl-N'-cyclohexyl-thiourea (TU):

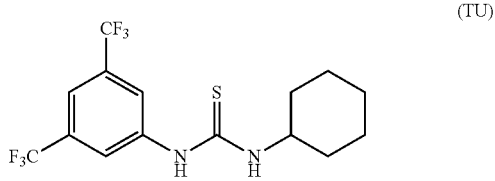 [SMILES: FC(F)(F)c1cc(NC(=S)NC2CCCCC2)cc(C(F)(F)F)c1]

Other organocatalysts comprise at least one 1,1,1,3,3,3-hexafluoropropan-2-ol-2-yl (HFP) group. Singly-donating hydrogen bond catalysts have the formula (15):

$$R^2-C(CF_3)_2OH \quad (15).$$

$R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 3.

TABLE 3

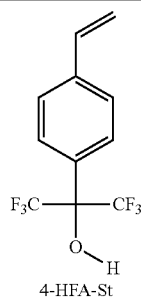

4-HFA-St

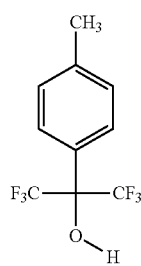

TABLE 3-continued

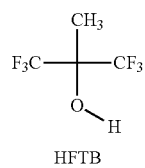

HFTB

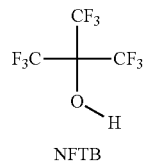

NFTB

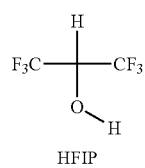

HFIP

Doubly-donating hydrogen bonding catalysts have two HFP groups, represented by the general formula (16):

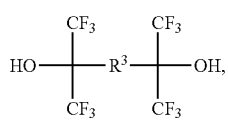

(16)

wherein $R^3$ is a divalent radical bridging group containing from 1 to 20 carbons, such as an alkylene group, a substituted alkylene group, a cycloalkylene group, a substituted cycloalkylene group, a heterocycloalkylene group, substituted heterocycloalkylene group, an arylene group, a substituted arylene group, or a combination thereof. Representative double hydrogen bonding catalysts of formula (16) include those listed in Table 4. In a specific embodiment, $R^2$ is an arylene or substituted arylene group, and the HFP groups occupy positions meta to each other on the aromatic ring.

TABLE 4

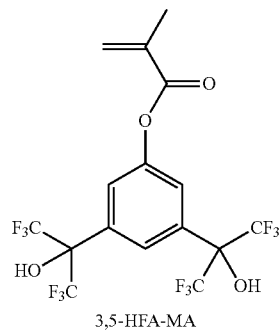

3,5-HFA-MA

TABLE 4-continued

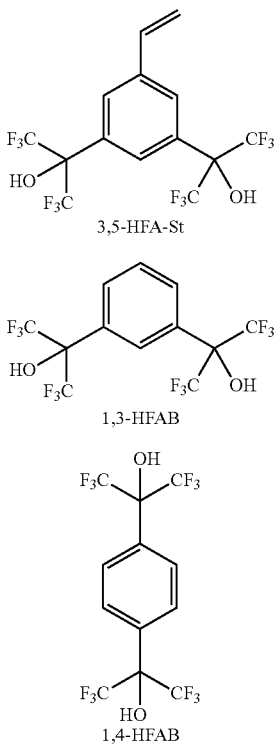

3,5-HFA-St 1,3-HFAB 1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are organocatalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Typical examples of such polymerizeable HFP-containing monomers may be found in: Ito et al., *Polym. Adv. Technol.* 2006, 17(2), 104-115, Ito et al., *Adv. Polym. Sci.* 2005, 172, 37-245, Ito et al., US20060292485, Maeda et al. WO2005098541, Allen et al. US20070254235, and Miyazawa et al. WO2005005370. Alternatively, pre-formed polymers and other solid support surfaces can be modified by chemically bonding an HFP-containing group to the polymer or support via a linking group. Examples of such polymers or supports are referenced in M. R. Buchmeiser, ed. "Polymeric Materials in Organic Synthesis and Catalysis," Wiley-VCH, 2003, M. Delgado and K. D. Janda "Polymeric Supports for Solid Phase Organic Synthesis," *Curr. Org. Chem.* 2002, 6(12), 1031-1043, A. R. Vaino and K. D. Janda "Solid Phase Organic Synthesis: A Critical Understanding of the Resin", *J. Comb. Chem.* 2000, 2(6), 579-596, D. C. Sherrington "Polymer-supported Reagents, Catalysts, and Sorbents: Evolution and Exploitation—A Personalized View," *J. Polym. Sci. A. Polym. Chem.* 2001, 39(14), 2364-2377, and T. J. Dickerson et al. "Soluble Polymers as Scaffold for Recoverable Catalysts and Reagents," *Chem. Rev.* 2002, 102(10), 3325-3343. Examples of linking groups include $C_1$-$C_{12}$ alkyl, $C_1$-$C_{12}$ heteroalkyl, an ether group, a thioether group, an amino group, an ester group, an amide group, or a combination thereof. Also contemplated are catalysts comprising charged HFP-containing groups bound by ionic association to oppositely charged sites on a polymer or a support surface.

The organocatalyst can also be a nitrogen base, as indicated above. Exemplary nitrogen base catalysts include triallylamine, triethylamine, tri-n-octylamine and benzyldimethylamine. Other nitrogen base catalysts, listed in Table 5, include pyridine (Py), N,N-dimethylaminocyclohexane (Me₂NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i--propylphenyl(imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i--propylphenyl)-4,5-dihydroimidazol-2-ylidene, 1,3-bis(2,6-di-i-propylphenyl)-4,5-dihydroimidazol-2-ylidene (Im-8) or a combination thereof.

TABLE 5

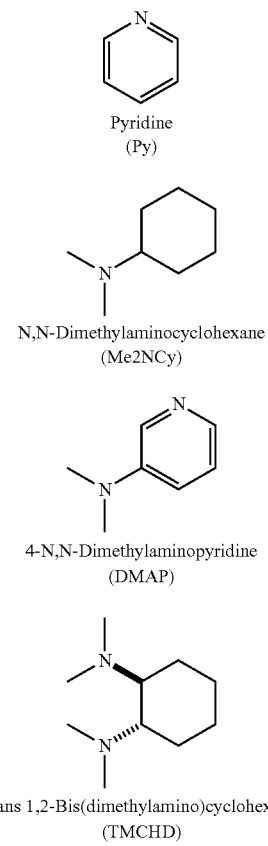

Pyridine
(Py)

N,N-Dimethylaminocyclohexane
(Me2NCy)

4-N,N-Dimethylaminopyridine
(DMAP)

trans 1,2-Bis(dimethylamino)cyclohexane
(TMCHD)

TABLE 5-continued

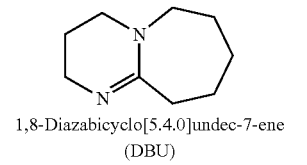

1,8-Diazabicyclo[5.4.0]undec-7-ene
(DBU)

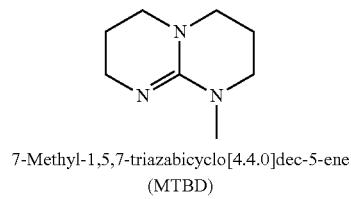

7-Methyl-1,5,7-triazabicyclo[4.4.0]dec-5-ene
(MTBD)

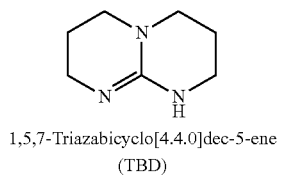

1,5,7-Triazabicyclo[4.4.0]dec-5-ene
(TBD)

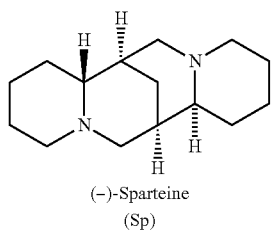

(−)-Sparteine
(Sp)

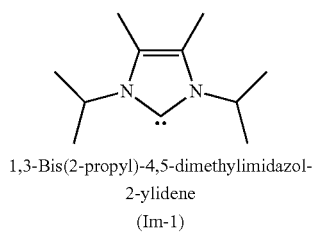

1,3-Bis(2-propyl)-4,5-dimethylimidazol-
2-ylidene
(Im-1)

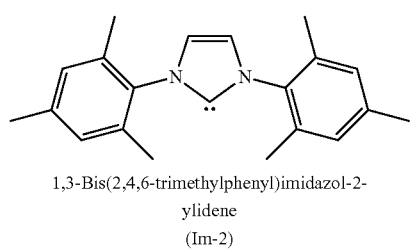

1,3-Bis(2,4,6-trimethylphenyl)imidazol-2-
ylidene
(Im-2)

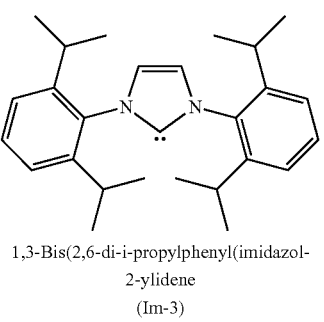

1,3-Bis(2,6-di-i-propylphenyl(imidazol-
2-ylidene
(Im-3)

TABLE 5-continued

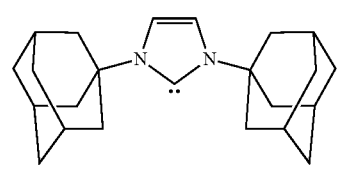

1,3-Bis(1-adamantyl)imidazol-2-yliden)
(Im-4)

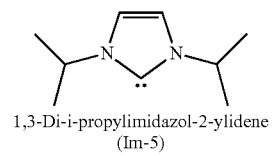

1,3-Di-i-propylimidazol-2-ylidene
(Im-5)

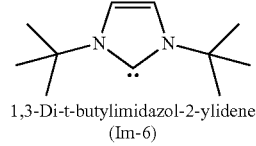

1,3-Di-t-butylimidazol-2-ylidene
(Im-6)

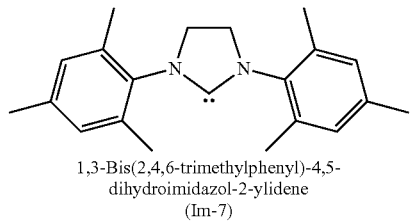

1,3-Bis(2,4,6-trimethylphenyl)-4,5-
dihydroimidazol-2-ylidene
(Im-7)

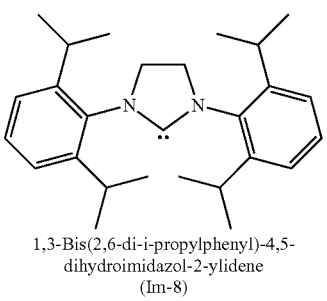

1,3-Bis(2,6-di-i-propylphenyl)-4,5-
dihydroimidazol-2-ylidene
(Im-8)

The above-described nitrogen bases can be used alone as a catalyst when producing linear polymers by ring opening polymerization, such as the polymer arm precursor. Alternatively, the nitrogen bases can serve as an optional accelerator when used in combination with a primary catalyst, such as TU, in a ring opening polymerization. When employed as an accelerator, each nitrogen is potentially capable of participating as a Lewis base. In general, stronger nitrogen base accelerators improve the polymerization rate.

Exceptions to the above have been found by the present inventors when attempting to generate the microgel core by ring opening polymerization using base catalysis alone. In these instances, nitrogen bases comprising 1 or 2 nitrogens were not effective in forming uni-molecular star polymers. The 1-nitrogen and 2-nitrogen base catalysts produced star polymers having high polydispersities (greater than 1.35), or products that were amorphous. After considerable experimentation, it was found that the formation of the microgel core by ring opening polymerization of a bis-cyclic carbonyl monomer to form a star polymer could be accomplished using a nitrogen base comprising three or more nitrogens. Uni-molecular nano-sized amphiphilic star polymers having a polydispersity of 1.35 or less were successfully produced using this type of catalyst. One such base catalyst is 1,5,7-triazabicyclo[4.4.0]dec-5-ene (TBD). In Example 1, described further below, a star polymer is formed using TBD as the sole catalyst. The star polymer has a polydispersity index of 1.26, a hydrodynamic radius of 10.9 nm, and contains less than 100 ppm of any restricted metal. The star polymer of Example 1 is also amphiphilic and biodegradable, making it an exceptional candidate as a carrier for biologically active materials for in vivo medical applications.

The ROP reaction mixture comprises at least one catalyst and, when appropriate, several catalysts together. The ROP catalyst is added in a proportion of 1/20 to 1/40,000 moles relative to the cyclic carbonyl monomers, and preferably of 1/100 to 1/20,000 moles.

The ROP reaction mixture also comprises an initiator. Initiators generally include nucleophiles such as alcohols, amines and thiols. The initiator can be monofunctional, difunctional, or multifunctional. The initiator can be polymeric or non-polymeric. For example, the initiator can be a polymeric alcohol, polymeric amine, or polymeric thiol.

More particularly, the initiator for the ring opening reaction is an alcohol. The alcohol initiator can be any suitable alcohol, including mono-alcohol, diol, triol, or other polyol, with the proviso that the choice of alcohol does not adversely affect the polymerization yield, polymer molecular weight, complexation with a biologically active material, and/or the desirable mechanical and physical properties of the star polymer. The alcohol can be multi-functional comprising, in addition to one or more hydroxyl groups, a halide, an ether group, an ester group, an amide group, or other functional group. Exemplary alcohols includes methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohol, benzenedimethanol, trimethylolpropane, a saccharide, poly(ethylene glycol), propylene glycol, alcohol functionalized block copolymers derived from oligomeric alcohols, alcohol functionalized branched polymers derived from branched alcohols, or a combination thereof. Monomeric diol initiators include ethylene glycols, propylene glycols, hydroquinones, and resorcinols. An example of a diol initiator is BnMPA, derived from 2,2-dimethylol propionic acid.

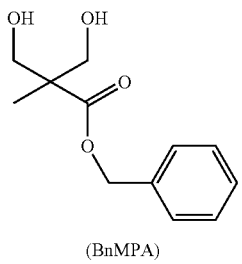 [SMILES: CC(CO)(CO)C(=O)OCc1ccccc1]

(BnMPA)

BnMPA is a precursor used in the preparation of cyclic carbonate monomers.

The ring-opening polymerization can be performed with or without the use of a solvent, more particularly with a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable cyclic carbonyl monomer concentration is about 0.1 to 5 moles per liter, and more particularly about 0.2 to 4 moles per liter. In a specific embodiment, the reaction mixture for the ring-opening polymerization is free of a solvent.

The ring-opening polymerization can be performed at a temperature that is about ambient temperature or higher, more specifically a temperature from 15° C. to 200° C., and more particularly 20° C. to 200° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours.

Whether performed in solution or in bulk, the ring opening polymerizations are conducted in an inert (i.e., dry) atmosphere and at a pressure of from 100 to 500 MPa (1 to 5 atm), more typically at a pressure of 100 to 200 MPa (1 to 2 atm). At the completion of the reaction, the solvent can be removed using reduced pressure.

The nitrogen base accelerator, when used, is present in an amount of 0.1 to 5.0 mol %, 0.1 to 2.5 mol %, 0.1 to 1.0 mol %, or 0.2 to 0.5 mol %, based on total moles of cyclic carbonyl monomer.

The amount of initiator for the ring opening polymerization is calculated based on the equivalent molecular weight per nucleophilic initiating group in the initiator (e.g., alcohol groups). The initiating groups are present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5 g per mole of monomer.

In a specific embodiment, the catalyst is present in an amount of about 0.2 to 20 mol %, and the hydroxyl groups of the initiator are present in an amount of 0.1 to 5.0 mol % based on the equivalent molecular weight per nucleophilic group in the initiator.

As stated above, the ring opening polymerization forms a polymer chain comprising a living polymer segment. In an embodiment, one backbone repeating unit of the ROP polymer chain is an ester repeating unit. The ROP polymer backbone can, for example, also comprise a polyester homopolymer, a random polyester copolymer, a polycarbonate homopolymer, a random polycarbonate copolymer, or a random polyestercarbonate copolymer. The ROP polymer chain can comprise a terminal hydroxyl group, terminal thiol group, or terminal amine group, each of which can initiate further ROP chain growth, if desired.

The ROP polymer can comprise hydrophilic repeat units, hydrophobic repeat units, and combinations thereof, thereby imparting amphiphilic properties to the star polymer. The ROP polymer chains can have a number average molecular weight $M_n$ as determined by size exclusion chromatography of at least 2500 g/mol, more specifically 4000 g/mol to 150000 g/mol, and even more specifically 10000 g/mol to 50000 g/mol. In an embodiment, the ROP polymer chain has a number average molecular weight $M_n$ of 10000 to 20000 g/mole. The ROP polymer chains also have a narrow polydispersity index (PDI), generally less than or equal to 1.35, more particularly from 1.01 to 1.35, even more particularly 1.1 to 1.30, and still more particularly 1.1 to 1.25.

As stated above, the ROP polymer can comprise a pendant latent carboxylic acid group, such as a benzyl ester. In this instance, the latent carboxylic acid group can be deprotected using $H_2$/Pd—C to form a pendant carboxylic acid group. If the protected carboxylic acid is in the form of a thermally labile carboxylic ester, such as a t-butyl ester, deprotection can be effected by heating the ROP polymer. If the protected carboxylic acid is hydrolytically unstable, such as a trifluoroethyl ester, the ROP polymer can be deprotected with mild aqueous acid or base to form a pendant carboxylic acid group. In a particular embodiment, the protected carboxylic acid is a benzyl ester.

The star polymers can comprise repeat units comprising a positive charge, a negative charge, or a mixture thereof.

In aqueous solution the star polymers disperse to form nanoparticles having an average particle size of from 2 nm to 500 nm, 10 nm to 250 nm, and more particularly 50 nm to 200 nm, 50 nm to 150 nm, 50 nm to 120 nm, and even more particularly from 50 nm to 100 nm, as measured by dynamic light scattering (Brookhaven Instrument Corp., Holtsville, N.Y., U.S.A.) equipped with a He—Ne laser beam at 658 nm (scattering angle: 90°. The particle size measurements are repeated for 5 runs for each sample, and the particle size are reported as the average of 5 readings. For the foregoing particle sizes, the aqueous solution can have a pH of from 5.0 to 8.0. This pH range can be increased for non-biodegradable compositions, such as those having a microgel core prepared from divinylbenzene.

Also disclosed are loaded star polymers, comprising the star polymer and a cargo material selected from the group consisting of drugs, genes, dyes, image contrast enhancing materials, and combinations thereof. The cargo material can comprise a metal, including one or more of the above-described restricted metals. The cargo material can also comprise a radioactive heavy metal. The loaded star polymers are also referred to herein as loaded nanoparticles. In aqueous solution at a pH of from 5.0 to 8.0, the loaded nanoparticles have an average particle size of from 2 nm to 500 nm, 2 nm to 250 nm, 2 nm to 150 nm, 2 nm to 120 nm, and more particularly 10 nm to 120 nm, 20 nm to 120 nm, 30 nm to 120 nm, and even more particularly from 50 nm to 120 nm, as measured by dynamic light scattering (Brookhaven Instrument Corp., Holtsville, N.Y., U.S.A.) equipped with a He—Ne laser beam at 658 nm (scattering angle: 90°). The particle size measurements are repeated for 5 runs for each sample, and the particle size are reported as the average of 5 readings. The loaded nanoparticles can comprise, for example 0.1 to 90 wt. %, more particularly 5 to 50 wt. %, and even more particularly 15 to 50 wt. % of a biologically active material based on total dry weight of the loaded nanoparticles. In an embodiment, the biologically active cargo material is a drug. In another embodiment, the biologically active material is a contrast enhancing agent.

The present loaded star polymers can comprise both small molecular weight biologically active materials in the size range from 100 daltons to about 1,000 daltons as well as larger macromolecular materials, such as peptide and protein drugs in the size range from about 1,000 daltons to about 100,000 daltons, and beyond.

Contrast enhancing agents that have been considered for nuclear magnetic resonance imaging include soluble salts of paramagnetic metal ions, paramagnetic chelates and metallic complexes, and nitroxide stable free radicals. Paramagnetic metals ions include: from the transition metals series: titanium ($Ti^{3+}$), iron ($Fe^{3+}$), vanadium ($V^{4+}$), cobalt ($Co^{3+}$), chromium ($Cr^{3+}$), nickel ($Ni^{2+}$), manganese ($Mn^{2+}$), and copper ($Cu^{2+}$); from the Lanthanide series: praseodynium ($Pr^{3+}$), gadolinium ($Gd^{3+}$), europium ($Eu^{3+}$), and dysprosium ($Dy^{3+}$); from the Actinide series: protactinium ($Pa^{4+}$); and from nitroxide stable free radicals: pyrrolidine derivatives, and piperidine derivatives. Of these, the most favored contrast enhancing agents include complexes of ferric, chromium, and gadolinium ions, and stable nitroxide free radicals. Exemplary contrast enhancing agents for x-ray imaging include barium salts and halogenated materials, more particularly brominated and/or iodinated materials.

Organic contrast enhancing agents include porphyrinoids, which include but are not limited to porphyrins, corrins, chlorins, bacteriochlorophylls, phthalocyanines, tetraazaphyrins, texaphyrins, saphyrins, and the like. A nonlimiting example of a porphyrinoid compound is 5,10,15,20-(3,5-ditertbutylphenyl)porphyrin, where the ligand M can be a metal or two hydrogens (M=2H) (DTBP):

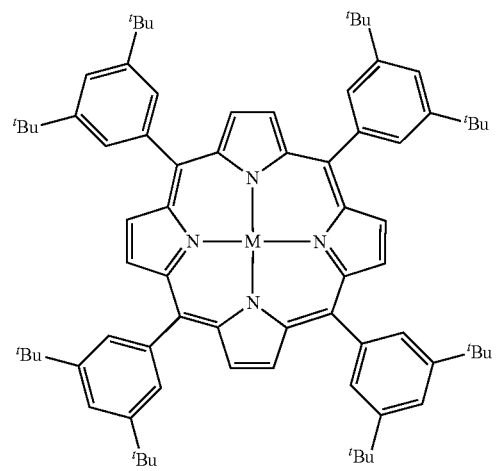

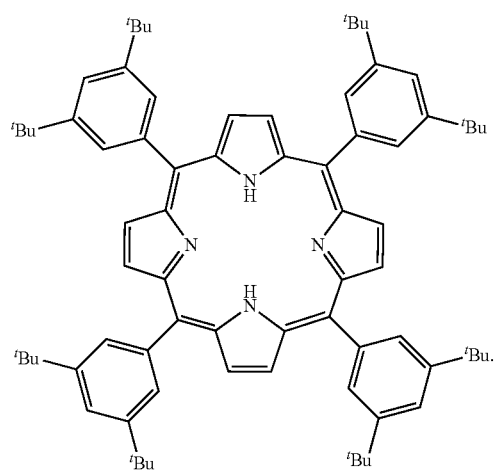

(DTBP)

Another nonlimiting example of a porphyrinoid compound is tert-butyl phthalocyanine, wherein the ligand M can be a metal or two hydrogens (M=2H) (TBP):

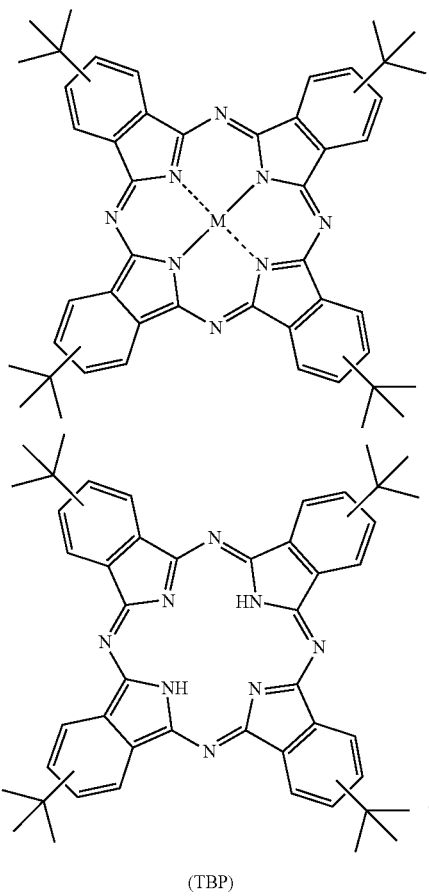

(TBP)

The contrast enhancing material can also comprise a combination of a porphyrinoid compounds. The porphyrinoid compound can further comprise a metal ligand that is a restricted metal.

The porphyrinoid compound can be in a non-aggregated state in the loaded star polymer, detectable by the fluorescence of an aqueous mixture of the loaded star polymer. In an embodiment, 10% to 100% by weight of the porphyrinoid compound in the loaded star polymer is in a non-aggregated state. In another embodiment, 50% to 100% by weight of the porphyrinoid compound in the loaded star polymer is in a non-aggregated state.

Exemplary protein drugs include peptide hormones such as insulin, glucagon, parathyroid hormone, calcitonin, vasopression, renin, prolactin, growth hormone, the gonadotropins including chorionic gonadotropin, follicle stimulating hormone, thyroid stimulating hormone and leutenizing hormone; physiologically active enzymes such as transferases, hydrolases, lyases, isomerases, phosphatases, glycosidases, superoxide dismutase, factor VIII, plasminogen activators; and other therapeutic agents including protein factors such as epidermal growth factor, insulin-like growth factor, tumour necrosis factor, transforming growth factors, fibroblast growth factors, patelet-derived growth factors, erythropoietin, colony stimulating factors, bone morphogenetic proteins, interleukins and interferons. Exemplary non-protein macromolecules include polysaccharides, nucleic acid polymers, and therapeutic secondary metabolites including plant products such as vinblastine, vincristine, taxol and the like.

Other exemplary drugs include Aspirin, Diflunisal, Diclofenac, Aceclofenac, Acemetacin, Etodolac, Indometacin, Sulindac, Tolmetin, Ibuprofen, Carprofen, Fenbufen, Fenoprofen, Flurbiprofen, Ketoprofen, Ketorolac, Loxoprofen, Naproxen, Oxaprozin, Tiaprofenic acid, Suprofen, Mefenamic acid, Meclofenamic acid, Lumiracoxib, Oxyphenbutazone, Piroxicam, Lornoxicam, Meloxicam, and Tenoxicam. Steroidal Anti-Inflammatory Drugs include Hydrocortisone, Prednisone, Prednisolone, Methylprednisolone, Dexamethasone, Betamethasone, Triamcinolone, Beclometasone, Fludrocortisone acetate, and Aldosterone. Chemotherapeutic drugs include Doxorubicin and DNA alkylating Agents such as Melphalan, Chlorambucil, Dacarbazine, Temozolomide, and Streptozotocin. Antimetabolite drugs include Methotrexate, Pemetrexed, Raltitrexed, Tioguanine, Fludarabine, Pentostatin, Cladribine, Floxuridine, and Gemcitabine. Alkaloid drugs include Vincristine, Vinblastine, Vinorelbine, Vindesine, and Topoisomerase. Inhibitors include Etoposide, Teniposide, Irinotecan, and Topotecan. Taxanes include Paclitaxel and Docetaxel. Anticoagulants include Warfarin, Acenocoumarol, Phenprocoumon, Argatroban, and Ximelagatran.

Still other exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Oraprel®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

Also disclosed is a method of preparing a loaded star polymer, comprising i) forming a mixture of an amphiphilic star polymer and a biologically active material in a first solvent; and ii) injecting the mixture into a second solvent, the second solvent being a non-solvent for the biologically active material, thereby forming nanoparticles of a loaded star polymer; wherein the star polymer comprises a crosslinked living microgel core and 6 or more independent polymer arms covalently linked to the core, the 6 or more polymer arms each comprise a hydrophobic chain segment and a hydrophilic chain segment, and the star polymer comprises no more than 100 ppm of any single restricted metal.

Also disclosed is an aqueous mixture comprising i) a star polymer comprising a crosslinked living microgel core and 6 or more independent polymer arms covalently linked to the core, the 6 or more arms each comprising a hydrophilic polymer chain segment and a hydrophobic polymer chain segment, the star polymer comprising no more than 100 ppm of any single restricted metal; and ii) a biologically active material in contact with the microgel core and/or with the 6 or more independent polymer arms. In an embodiment the biologically active material is an image contrast enhancing material. In another embodiment, the contrast enhancing material is a porphyrinoid compound. In another embodiment, the contrast enhancing material is selected from the group consisting of

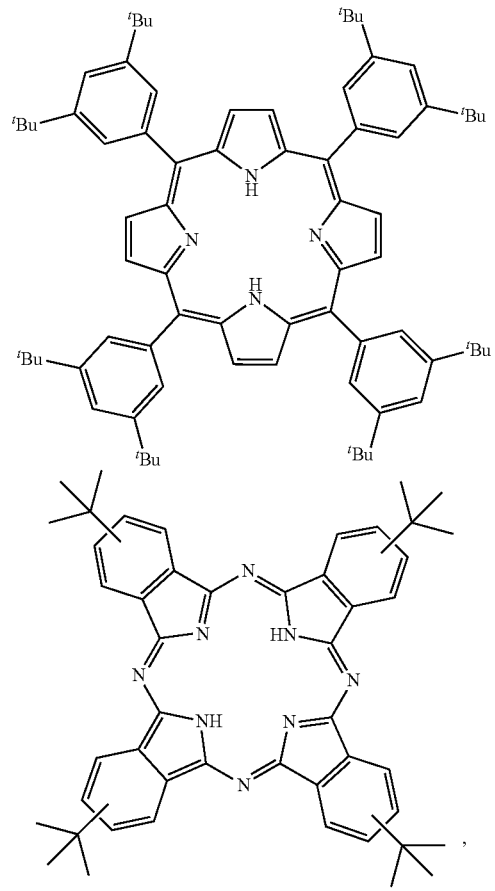

and combinations thereof.

In another embodiment, 10% to 100% of the image enhancing material is not aggregated in the loaded star polymer. In another embodiment, 50% to 100% of the image enhancing material is not aggregated in the loaded star polymer.

Further disclosed is a method of treating a cell, comprising contacting the cell with an aqueous mixture comprising the above described loaded star polymer. The biologically active cargo can comprise a single biologically active material or a mixture of biologically active materials. The biologically active material can be a substance selected from the group consisting of drugs, genes, dyes, image contrast enhancing materials, and combinations thereof. The biologically active cargo can be a drug, for example doxorubicin. In an embodiment, the biologically active material is a porphyrinoid compound. Cells can be contacted in vitro, ex vivo, or in vivo. Contacting induces 0% to 20%, 0% to 15%, 0% to 10%, 0% to 5%, 0% to 2%, or more particularly 0% to 1% cytotoxicity. In an embodiment, contacting induces no cytotoxicity.

No restriction is placed on the type of cell that can be treated with the above-described loaded nanoparticles. In particular, the cells can be eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described loaded star polymers can be used as non-viral transfection vectors. The target gene is not limited to any particular type of target gene or nucleotide sequence. For example, the target gene can be a cellular gene, an endogenous gene, an oncogene, a transgene, or a viral gene including translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NFI, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

The preparation and use of the star polymers and loaded star polymers is further illustrated by the following examples.

EXAMPLES

Materials used in the following examples are listed in Table 5.

TABLE 5

| Name | Description | Company |
| --- | --- | --- |
| MPEG | Poly(ethylene glycol) mono methyl ether, $M_n$ = 5000 | Fluka |
| TBD | 1,5,7-Triazabicyclo[4.4.0]dec-5-ene (organocatalyst) | Sigma Aldrich |
| BOD | 4-4'-Bioxepanyl-7,7'-dione | TCI America |
| BPEG | Boc-protected amino-poly(ethylene glycol) | Iris Biotech GmbH |
| DANSYL-Cl | 5-dimethylaminonaphthalen-1-sulfonyl chloride | Sigma Aldrich |

Preparation of 4-4'-Bioxepanyl-7,7'-dione (BOD)

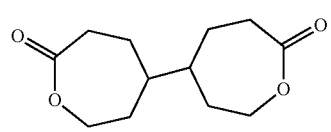

BOD

A solution of urea hydrogen peroxide ($CO(NH_2)_2$—$H_2O_2$) (20.0 g, 212 mmol) in 100 mL of formic acid (99%) was stirred at 23° C. for 90 minutes. The solution was then cooled to 0° C. before the addition of 4,4'-Bicyclohexanone (10.0 g, 51.4 mmol) over 5 to 10 minutes. The solution was then allowed to warm to ambient temperature and stirred for a further 4 hours. 200 mL of water was added to the mixture followed by extraction with chloroform. The organic fractions were collected, washed with a saturated aqueous sodium bicarbonate solution and dried with $Na_2SO_4$. The organic fraction was collected, the solvent removed under reduced pressure and the residue recrystallized from ethyl acetate to yield the product as a white amorphous solid (3.50 g, 60%). $^1$H NMR (400 MHz, $CDCl_3$), δ (ppm): 4.34 (R, R) 4.17 (S, R) (t, 2H, —$CH_2$OOC—), 2.73 (R, R) 2.60 (S, R) (t, 2H, —$CH_2$COO—), 1.93-1.83 (m, 2H, —$CH_2CH_2$OOC—), 1.70-1.60 (m, 2H, —$CH_2CH_2$COO—), 1.49 (q, 1 H, —$CHCH_2$—).]

Example 1

Single Pot Preparation of a Star Polymer SP-1

The numerical subscripts in the polymer structure represent relative mmoles of material used. In MPEG, n represents the degree of polymerization of approximately 110 based on average molecular weight $M_n$=5000.

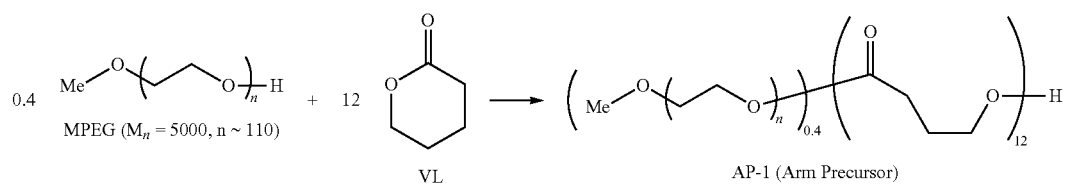

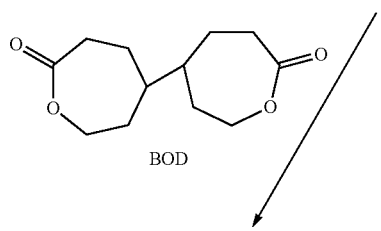

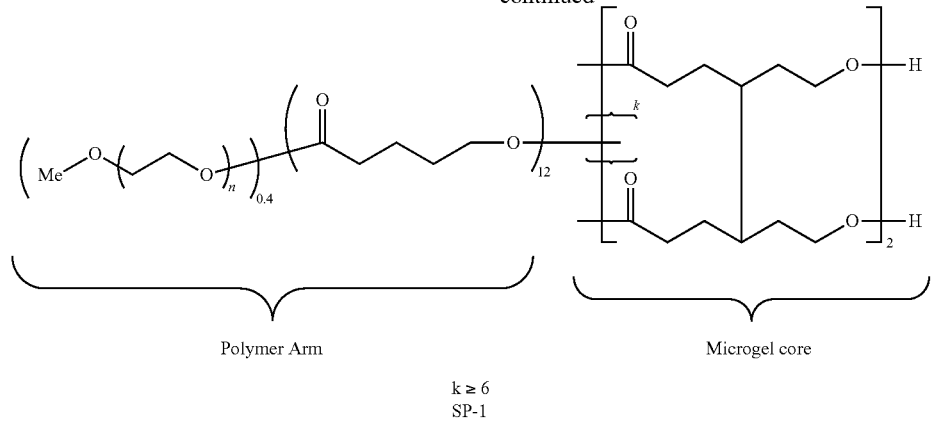

Polymer Arm | Microgel core k ≥ 6
SP-1

A solution of delta-valerolactone (1.2 g, 12.0 mmol) in anhydrous toluene (2.2 mL) was added to a stirring solution of poly(ethylene glycol) monomethyl ether (MPEG) ($M_n$=5000, 2.0 g, 0.4 mmol), and 1,5,7-triazabicyclo[4.4.0]dec-5-ene (TBD) (catalyst, 8.7 mg, 62.2 micromoles) in anhydrous toluene (7 mL). The reaction solution was stirred at room temperature under a nitrogen atmosphere for 15 minutes to generate a "living" block copolymer arm precursor AP-1. A solution of 4,4'-bioxepanyl-7,7'-dione (BOD) (0.5 g, 2.0 mmol) and TBD (8.7 mg, 62.2 micromoles) in anhydrous toluene (5.2 mL) was then added, and the reaction mixture was stirred at room temperature for a further 16 hours. The reaction mixture was then slowly added to cold diethyl ether (200 ml) with rapid stirring and the resulting precipitate isolated by filtration before being dried under reduced pressure to afford the crude product (3.6 g). The crude product was then dissolved in methanol (40 mL) and ethyl ether (70 mL) was added slowly, with rapid stirring until the onset of a persistent and uniform cloudiness. The mixture was allowed to settle overnight, forming a yellow oil on the bottom of the flask. The solution was decanted off and the oil was dissolved in a minimum amount of methanol and the solution was then slowly added to cold diethyl ether (200 ml) with rapid stirring and the resulting precipitate isolated by filtration before being dried under reduced pressure to afford the star polymer SP-1 as a white amorphous solid (1.8 g, 52%). 1H NMR (CDCl3, 400 MHz): delta (ppm)=4.21 (br, 2H, —O—CH2-CH2-OOC—), 4.06 (br, 112H, —CH2-CH2-COO—), 3.63 (br, 442H, —O—CH2-CH2-O—), 3.45 (s, 3H, CH3-O—CH2-), 2.32 (br, 112H, —CH2-CH2-COO—), 1.66 (br, 240H, —OOC—CH2-CH2-CH2-CH2-OOC—). Gel permeation chromatography (GPC) with refractive index (RI) detection: $M_n$=70000 g/mol, polydispersity index (PDI)=1.22. Dynamic light scattering (DLS) with refractive index detection (RI): $M_n$=363900 g/mol, PDI=1.26. Hydrodynamic radius (Rh)=10.9 nm.

Table 6 illustrates examples of the experimental conditions trialed in the development of a method of forming the following room temperature, polylactone (non-water-soluble) star polymer using an organocatalytic synthetic protocol with nitrogen base TBD. A solution of delta-valerolactone VL (10 g, 99.9 mmol) in 12.8 g of toluene (dry) was added to a stirring solution of benzyl alcohol (0.360 g, 3.33 mmol, [VL]$_o$/[BnOH]$_o$=30) and TBD (72 mg, 0.52 mmol) in 30 g of toluene (dry) under a nitrogen atmosphere and allowed to stir at room temperature to yield the "living" polymer arm. After 15 minutes a solution of BOD (3.762 g, 16.6 mmol, [BOD]$_o$/[Arm]$_o$=5) and TBD (72 mg, 0.52 mmol) in 96 g toluene (dry) was added quickly to the reaction mixture and allowed to stir at room temperature for a further 16 hours. The reaction mixture was then precipitated from cold methanol, filtered, and dried at room temperature under 100 mmHg. The crude polymer (10.11 g) was dissolved in 200 mL of acetone and 250 mL of methanol was added slowly, forming an emulsion. The emulsion was allowed to settle overnight, forming yellow oil on the bottom of the flask. The solution is decanted off and the oil was dissolved in a minimum amount of acetone and precipitated from cold methanol, filtered, and dried yielding the title compound as a white amorphous polymer (5.41 g, 54%). 1H NMR (CDCl3, 400 MHz): delta (ppm)=7.34 (br, 5H, H-Ph-), 5.1 (s, 2H, Ph-CH2-COO—), 4.06 (br, 92H, —CH2-CH2-OOC—), 3.65 (br, 2H, from the core —CH2-OH), 2.32 (br, 92H, —CH2-CH2-COO—), 1.65 (br, 200H, —OOC—CH2-CH2-CH2-CH2-OOC—). GPC (RI): Mn (PDI)=51 991 g/mol (1.22). DLS (RI): Mn, PDI, $R_h$=545 700 g/mol, 1.15, 4.9 nm.

TABLE 6

| Entry[1] | TBD[2] (mol %) | BOD[4] (eq) | Toluene (mL) | Chloroform (mL) | Time (h) | Mn[5] (kDa) | Result[6] | PDI (Mw/Mn) |
|---|---|---|---|---|---|---|---|---|
| 1 | 0.5 | 1.0 | 8.0 | 0.0 | 72 | 17.6 | 4 | >2 |
| 2 | 0.5 | 1.0 | 0.0 | 7.5 | 16 | 4.7 | 5 | 1.06 |
| 3 | 0.5 | 1.0 | 8.5 | 1.5 | 16 | 17.4 | 4 | >2 |
| 4 | 0.5 | 5.0 | 8.5 | 1.5 | 5 | 88.0 | 1 | 1.54 |
| 5 | 0.5 | 10.0 | 8.5 | 1.5 | 16 | 45.8 | 1 | 1.33 |
| 6 | 0.5 | 5.0 | 5.0 | 5.0 | 16 | 23.8 | 1 | 1.29 |
| 7 | 0.5 | 5.0 | 8.5 | 0.8 | 16 | 87.6 | 1 | 1.48 |
| 8 | 0.5 | 5.0 | 10.0 | 0.0 | 20 | 102.0 | 1 | 1.64 |
| 9 | 0.5 | 5.0 | 7.5 | 0.0 | 16 | N/A | 5 | N/A |
| 10 | 1.0[3] | 5.0 | 10.0 | 0.0 | 16 | 61.4 | 1 | 1.28 |

[1]In each case the loading and molecular weight (approx. 1 g, Mn ~3 000 g/mol) of the linear poly(valerolactone) arms created in situ was kept constant.
[2]mol % relative to initial monomer concentration
[3]added in two equivalents amounts in two steps, the first as for previous arm formation and the second added along with the addition of the BOD
[4]equivalents relative to linear arm macroinitiator
[5]Mn of major product determined by GPC analysis
[6]results where 1 = monomodal, 2 = bimodal, 3 = trimodal, 4 = multimodal, 5 = no result Example 2

Single pot preparation of star polymer SP-2 having a protected polymer arm end group and SP-3 having a deprotected polymer arm end group, where the subscripts represent relative moles.

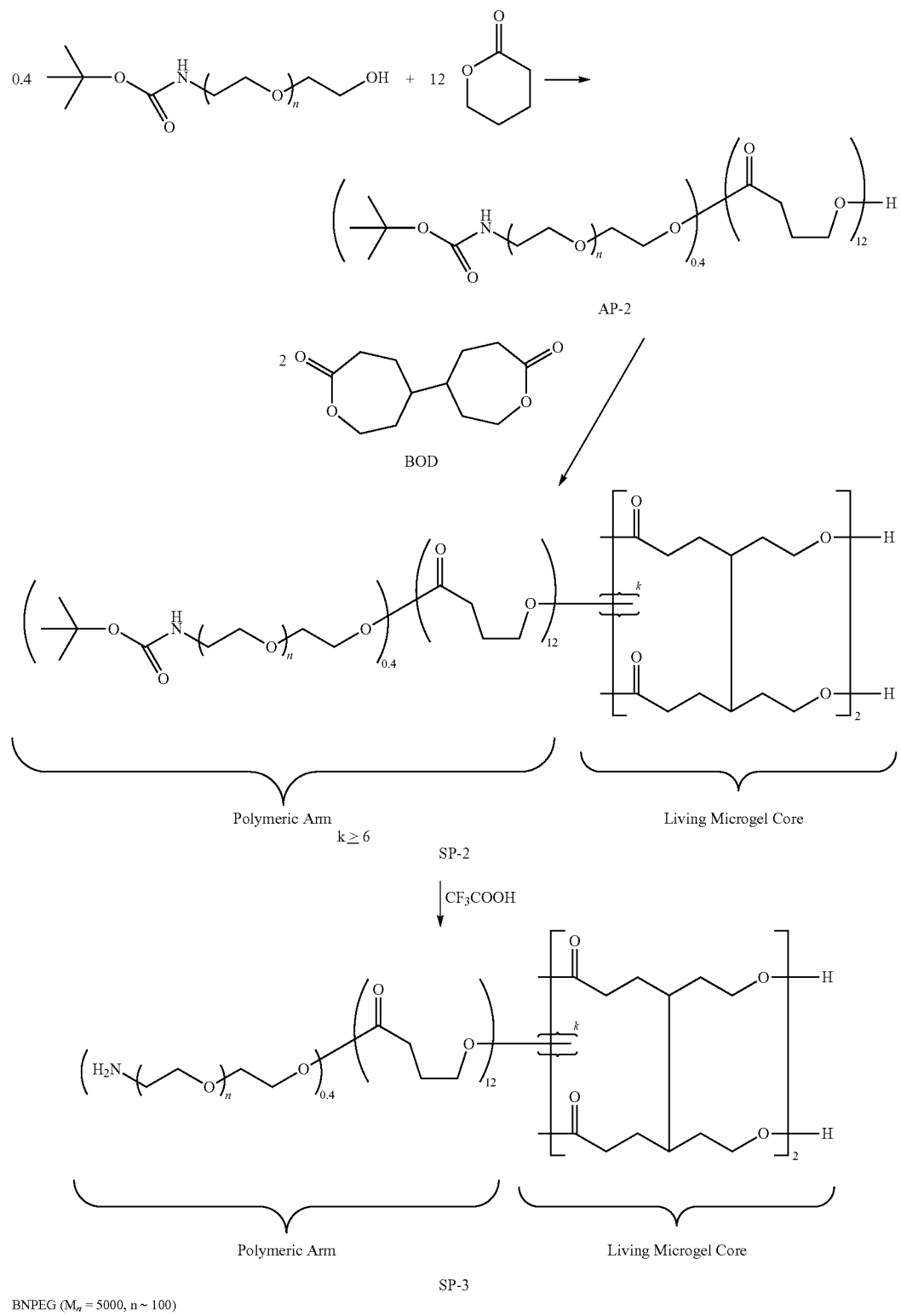

BNPEG ($M_n = 5000$, n ~ 100)

A solution of delta-valerolactone (1.2 g, 12.0 mmol) in anhydrous toluene (2.2 mL) was added to a stirred solution of Boc-protected amino-poly(ethylene glycol) (BNPEG) (2.0 g, 0.4 mmol) and TBD (8.7 mg, 62.2 micromoles) in anhydrous toluene (7.0 mL). The reaction mixture was allowed to stir at room temperature under a nitrogen atmosphere to generate the "living" block copolymer arm precursor AP-2. A solution of 4-4'-bioxepanyl-7,7'-dione (BOD) (0.5 g, 2.0 mmol) and TBD (8.7 mg, 62.2 micromoles) in anhydrous toluene (5.2 mL) was then added and the reaction mixture was allowed to stir at room temperature a further 16 hours. The reaction solution was then slowly added to cold diethyl ether (300 ml) with rapid stirring and the resulting precipitate isolated by filtration before being dried under reduced pressure to afford the crude star polymer product SP-2 (3.6 g). The crude product was then dissolved in methanol (40 mL) before ethyl ether (70 mL) was added slowly, with rapid stirring until the onset of a persistent and uniform cloudiness. The mixture was then allowed to settle overnight, forming a yellow oil on the bottom of the flask. The solution was decanted off, the oil dissolved in minimal methanol and the solution was then slowly added to cold diethyl ether (300 ml) with rapid stirring and the resulting precipitate isolated by filtration before being dried under reduced pressure to afford the BOC-protected star polymer SP-2 as a white amorphous solid (1.8 g, 49%). $^1$H NMR (CDCl3, 400 MHz): delta (ppm)=4.06 (br, 118H, —CH2-CH2-OOC—), 3.63 (br, 468H, —O—CH2-CH2-O—), 2.32 (br, 118H, —CH2-CH2-COO—), 1.66 (br, 260H, —OOC—CH2-CH2-CH2-CH2-OOC—), 1.42 (s, 9H, CH3-OOCNH—). GPC Mn (PDI)=71500 g/mol (1.24). DLS (RI): Mn=368000 g/mol, PDI=1.23, $R_h$=11.1 nm. Trifluoroacetic acid (0.2 mL, 2.6 mmol) was added to a solution of BOC-protected title compound star polymer (0.3 g, approx. 0.7 micromoles) in anhydrous methylene chloride (2.5 mL) before the reaction solution was left to stir at room temperature under a nitrogen atmosphere for 16 hours. The reaction solution was then slowly added to cold, degassed diethyl ether (150 mL) with rapid stirring and the resulting precipitate isolated by filtration under nitrogen (leaving slightly wet with diethyl ether), to afford the deprotected star polymer SP-3 as a white amorphous solid. The star polymer was stored slightly wet with diethyl ether under nitrogen at −18° C. $^1$H NMR (CDCl$_3$, 400 MHz): delta (ppm)=4.06 (br, 118H, —CH2-CH2-OOC—), 3.63 (br, 468H, —O—CH2-CH2-O—), 2.32 (br, 118H, —CH2-CH2-COO—), 1.66 (br, 260H, —OOC—CH2-CH2-CH2-CH2-OOC—).

Example 3

Preparation of Dansylated Star Polymer, SP-4

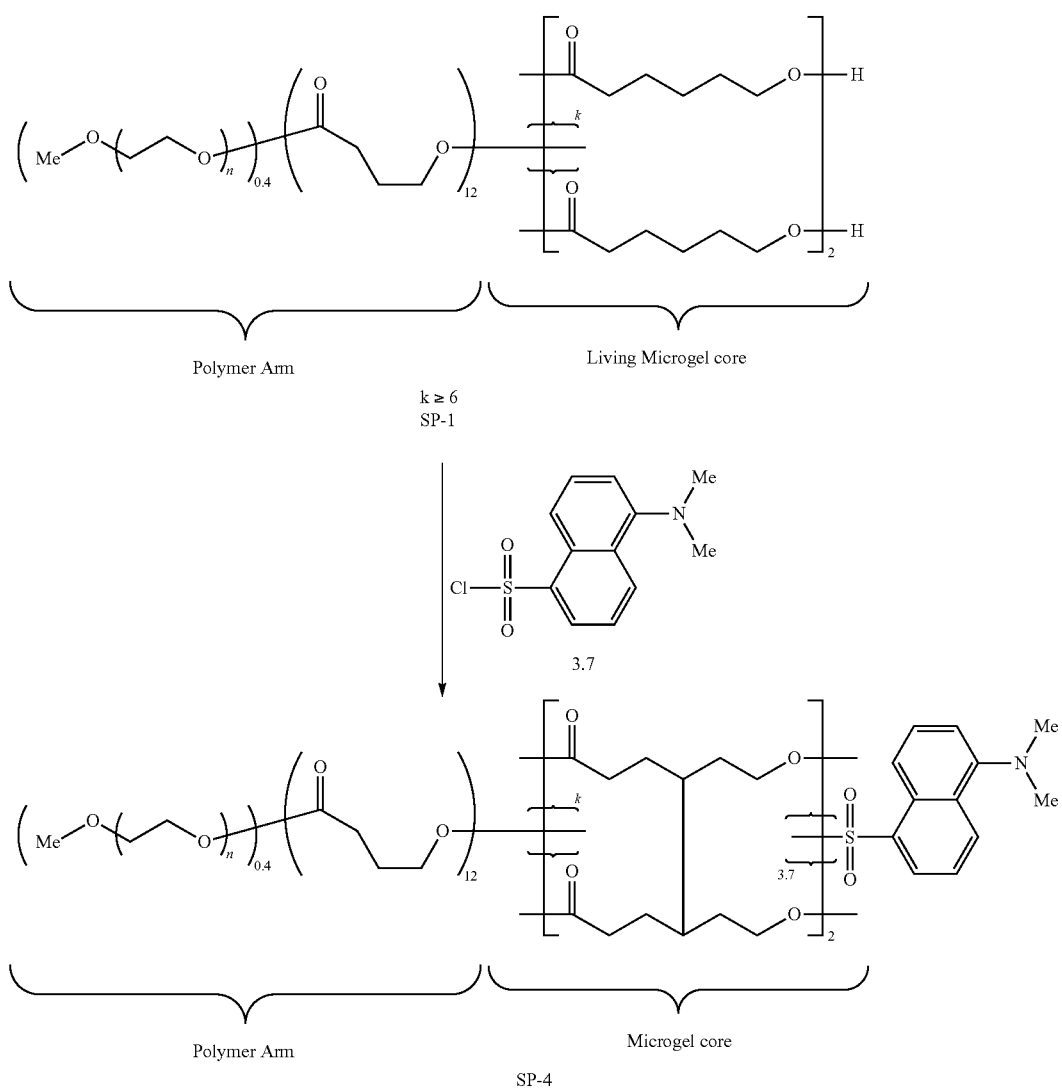

The star polymer SP-1 of Example 1 (1.0 g, approximately 3 micromoles based on average molecular weight, $M_n$ (360

Figure 3:
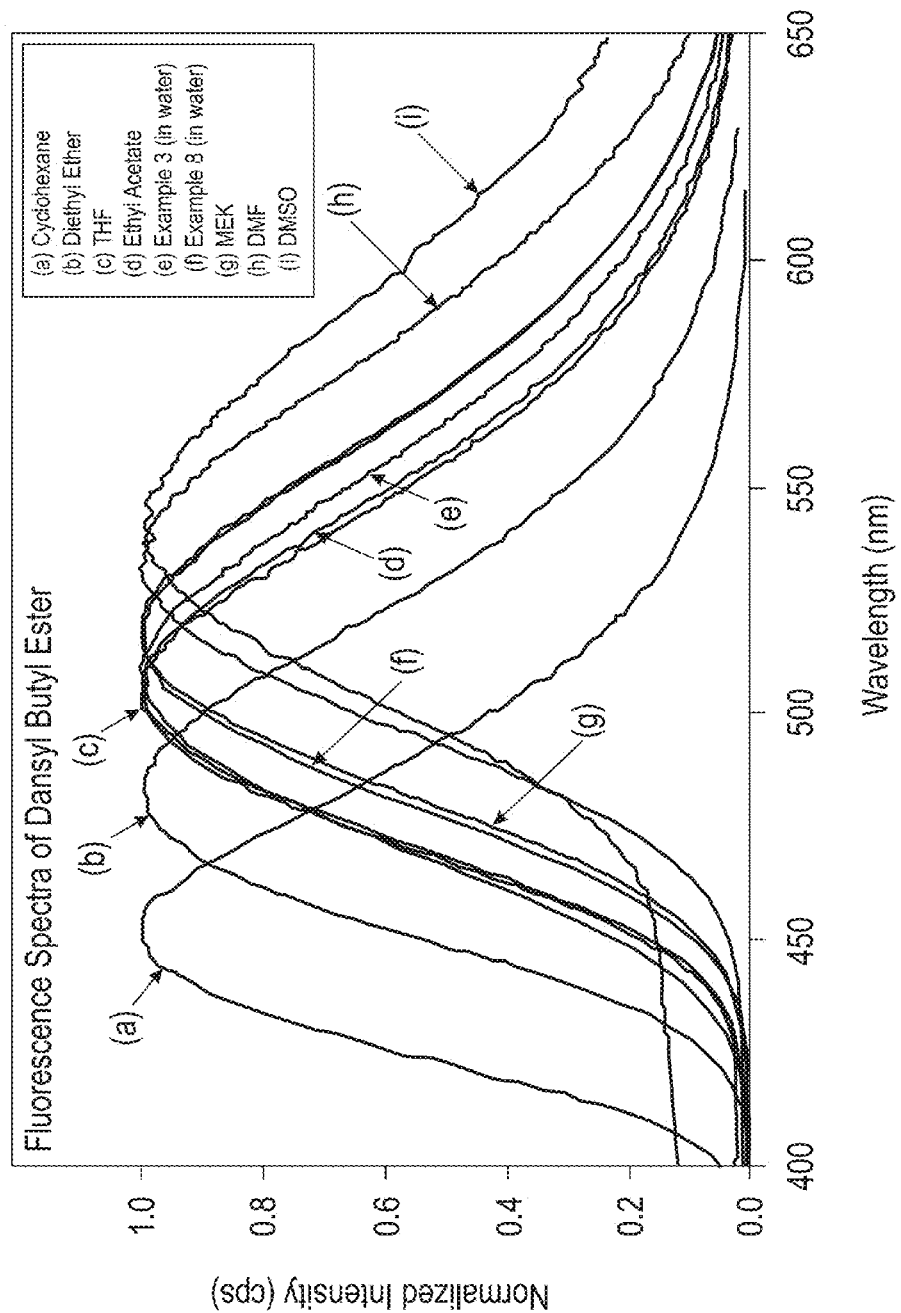
FIG. 3 is a graph comparing the UV-Visible absorption curves (absorbance versus wavelength in nanometers) of dansyl butyl ester (DBE) dissolved in various organic solvents, with the aqueous loaded star polymers of Example 3 (prepared by covalent bonding of dansyl chloride to the core of the star polymer of Example 1) and Example 8 (prepared by adsorption of dansyl butyl ester to the star polymer of Example 1).

KDa)) and 5-dimethylaminonaphthalen-1-sulfonyl chloride (dansyl chloride) (1.0 g, 3.7 mmol) were dissolved in anhydrous pyridine (7 mL) and left to stand at −18° C. for 16 hours. The reaction solution was then slowly added to cold diethyl ether (300 ml) with rapid stirring and the resulting precipitate isolated by filtration before being dried under reduced pressure to afford the crude product SP-4. The crude product was then dissolved in minimal methylene chloride, cooled and filtered. The filtrate was then slowly added to cold diethyl ether (300 ml) with rapid stirring and the resulting precipitate isolated by filtration before being dried under reduced pressure to afford dansylated star polymer SP-4 as a white amorphous solid (0.9 g, 90%). $^1$H NMR (CDCl$_3$, 400 MHz): delta (ppm)=8.83 (d, 1H, dansyl), 8.45 (t, 2H, dansyl), 7.97 (br, 3H, dansyl), 7.75 (d, 2H, from the core —CH═CH2-C—SO2-), 7.34 (br, 2H, from the core —CH═CH—C—SO2-), 4.21 (br, 2H, —O—CH2-CH2-OOC—), 4.06 (br, 112H, —CH2-CH2-OOC—), 3.63 (br, 444H, —O—CH2-CH2-O—, from the core —CH2-O-dansyl), 3.45 (s, 3H, CH3-O—CH2-), 2.88 (s, 6H, from dye (CH3)2-N—), 2.41 (s, 3H, CH3-Ph-), 2.32 (br, 112H, —CH2-CH2-COO—), 1.66 (br, 240H, —OOC—CH2-CH2-CH2-CH2-OOC—). FIG. 3 is a UV-VISIBLE absorption spectrograph comparing the absorption curves of Example 3 in water with dansyl butyl ester (DBE) in several solvents.

Example 4

Preparation of Polystyrene Star Polymers SP-5, SP-6 and SP-7

(A). Synthesis of "Protected" 3-(tert-Butyldimethylsilyloxy)-1-propyl-terminated Polystyrene Star-polymer SP-5 (Typical Procedure)

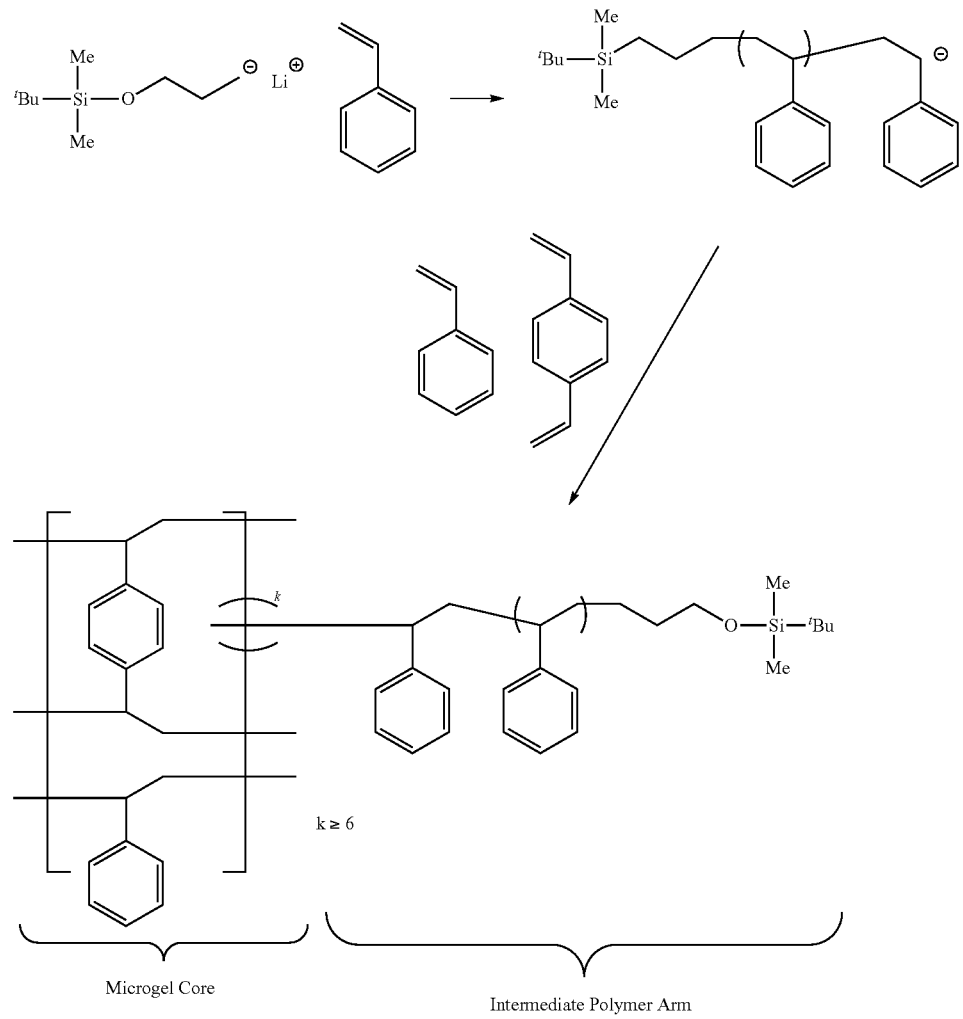

3-(tert-Butyldimethylsilyloxy)-1-propyl lithium (0.60 mL, 20 wt % solution in cyclohexane) was added to a stirred solution of styrene (12.00 mL) in a cyclohexane (200 mL) and THF (10 mL) mixture under an argon atmosphere. After 20 min an aliquot (approximately 2 mL) was taken, quenched in degassed MeOH (approx. 150 mL) and a representative sample of the "free" polystyrene arm collected by filtration. A mixture of p-divinylbenzene (2.70 mL) and styrene (0.12 mL) in cyclohexane (3.00 mL) was added and the reaction mixture stirred for a further 40 min. The reaction solution was then quenched by slow addition to a rapidly stirred solution of MeOH and EtOH (1.5 L, 1:1). The precipitate formed was isolated by filtration and air dried to a constant weight. The crude star-polymer was then dissolved in CH$_2$Cl$_2$ (100 mL) before the slow addition of acetone (150 mL) and then iso-propyl alcohol (30 mL). The solution was allowed to stand until the product formed a substantial oily layer on the bottom of the container. The mixture was decanted allowing isolation of the oil which was then dried in a vacuum oven to constant weight affording the "protected" intermediate star-polymer SP-5 (9.5 g). $^1$H NMR (400 MHz, CDCl$_3$) delta=0.18 (br s, 6H) 0.85 (br s, 9H), 1.44 (br s, 330 H) 1.85 (br s, 165 H), 3.35 (br s, 2 H) 6.50-6.60 (br m, 330 H), 7.10 (br s, 495 H). Analytical GPC: $M_w/M_n$=1.15. Light Scattering: $M_w$=600 000 g/mol, $M_w/M_n$=1.09, $R_h$(avg) 10.8 nm. $^1$H NMR (400 MHz, CDCl$_3$) analysis of the "free arm" sample indicated arm length of approx. 165 repeat units. This implied the approximate number of "arms" in the star-polymer was about 36.

(B). Synthesis of "Deprotected" Hydroxy-terminated Polystyrene Star-Polymer SP-6 (Typical Procedure)

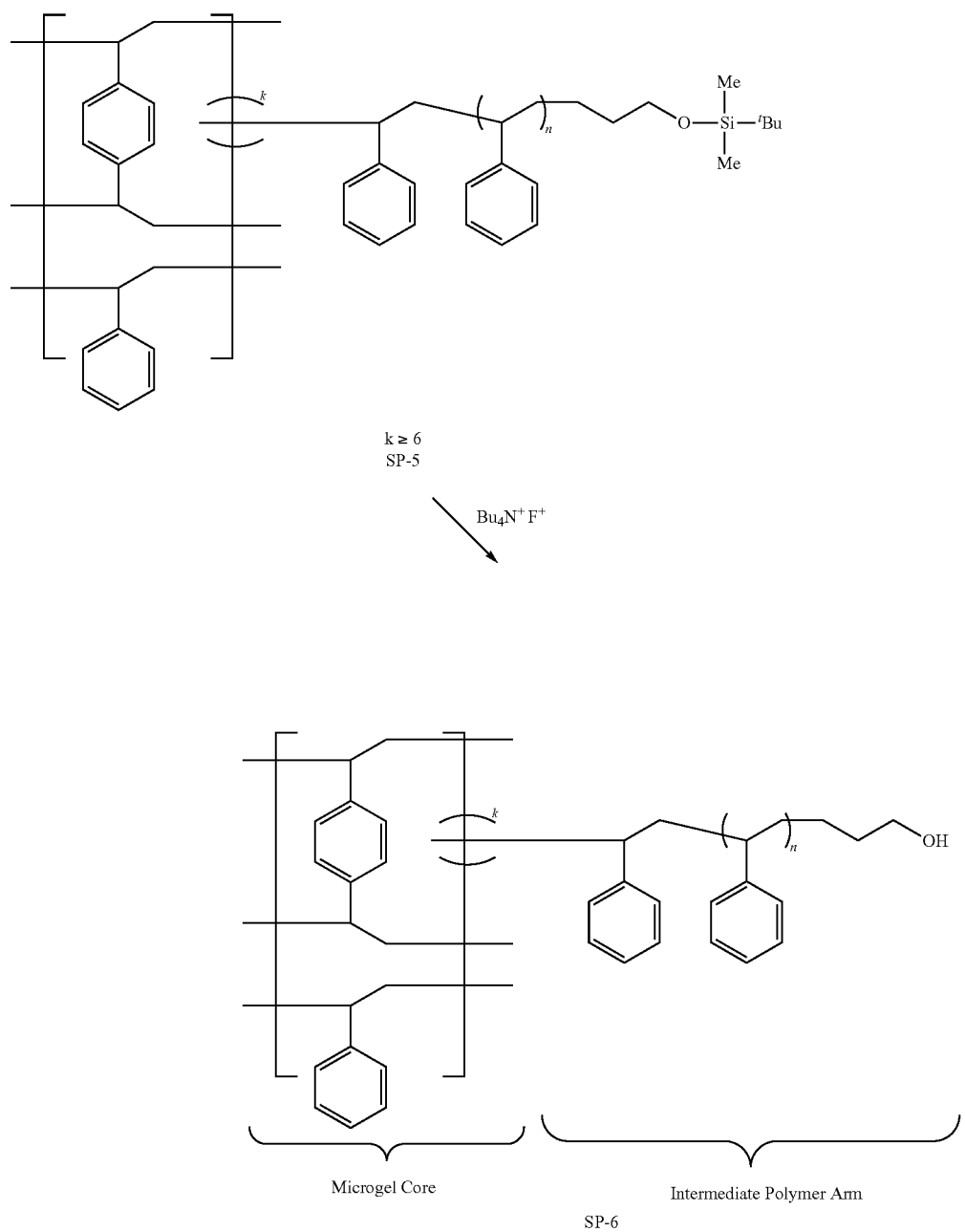

Intermediate star polymer SP-5 (9.0 g) was dissolved in THF (9.0 mL) and tetrabutylammonium fluoride (1.0 M solution in THF, 9.0 mL) was added. The reaction solution was stirred for 60 hours at room temperature before being warmed to 50° C. for 1 hour. The solution was allowed to cool to room temperature before it was slowly added to MeOH (1 L) with rapid stirring. The precipitate formed was isolated by filtration and air dried to a constant weight to afford the "deprotected" Intermediate star-polymer SP-6 (8.5 g). $^1$H NMR (400 MHz, CDCl$_3$) delta=1.44 (br s, 330 H) 1.85 (br s, 165 H), 3.45 (br s, 2 H) 6.50-6.60 (br m, 330 H), 7.10 (br s, 495 H). Analytical GPC: $M_w/M_n$=1.14. Light Scattering: $M_w$=608 000 g/mol, $M_w/M_n$=1.14, $R_h$(THF, average) 10.6 nm.

(C). Synthesis of "Activated" (p-Toluenesulfonyl)-terminated Polystyrene Star Polymer SP-7 (Typical Procedure)

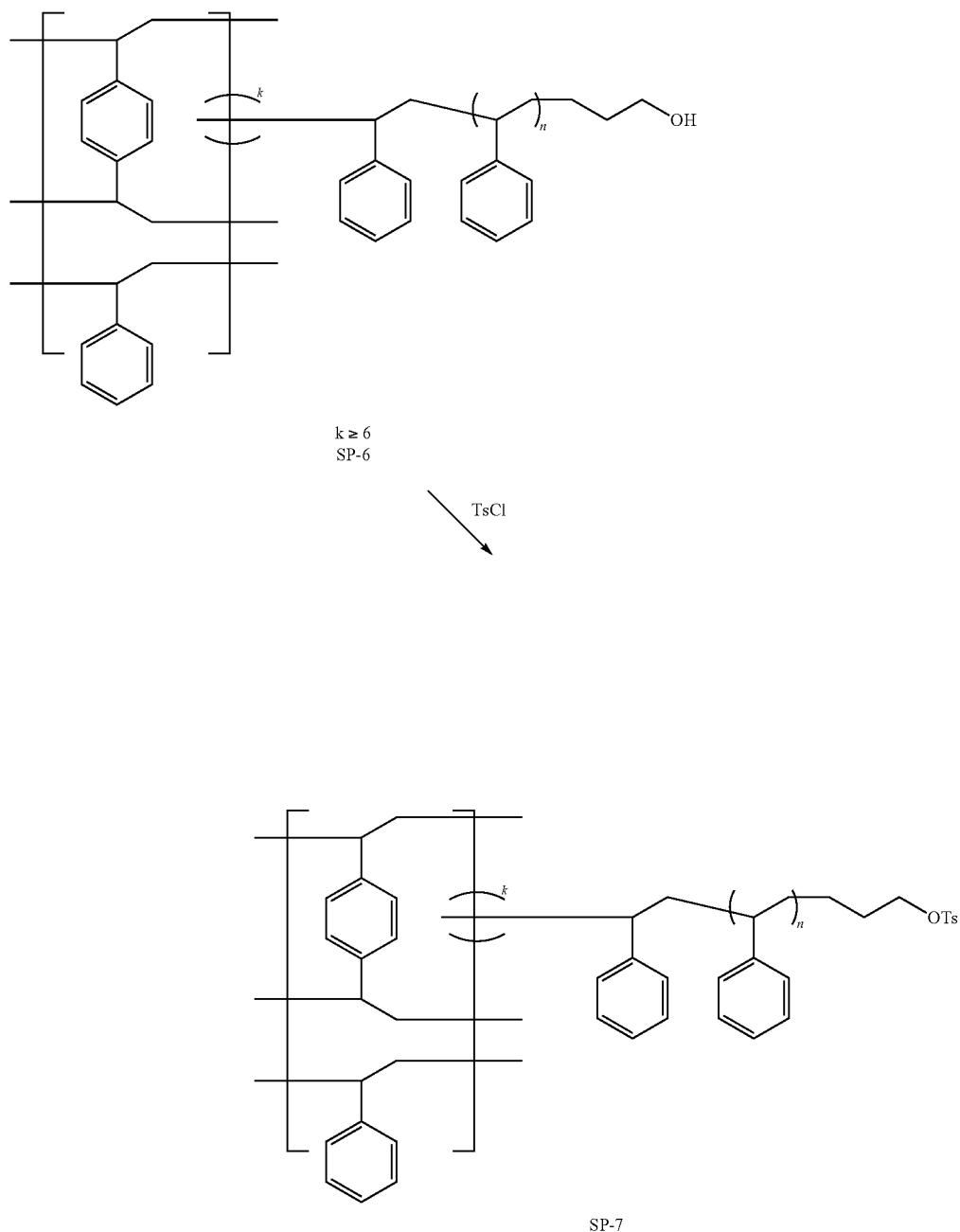

Star polymer SP-6 (5.0 g) was dissolved in anhydrous pyridine (50 mL) and cooled using an external ice bath. p-Toluenesulfonyl chloride (5.0 g) was slowly added to the reaction solution with rapid stirring. The reaction flask was sealed and kept at 0° C. for 18 hours. The reaction mixture was then slowly added to water (500 mL) with rapid stirring. The precipitate formed was isolated by filtration and air dried to a constant weight. This crude product was then dissolved in THF (10 mL) and slowly added to MeOH (500 mL) with rapid stirring. The precipitate formed was isolated by filtration and air dried to a constant weight to afford the "activated" star polymer SP-7 (4.8 g). $^1$H NMR (400 MHz, CDCl$_3$) delta=1.44 (br s, 330 H) 1.85 (br s, 165 H), 2.38 (br s, 3 H), 3.85 (br s, 2 H) 6.50-6.60 (br m, 330 H), 7.10 (br m, 497 H) 7.72 (br s, 2 H). Analytical GPC: $M_w/M_n$=1.15. Light Scattering: $M_w$=594 000 g/mol, $M_w/M_n$=1.09, $R_h$(avg) 10.7 nm.

Example 5

Preparation of Mono Methyl Poly(Ethylene Glycol) Terminated Polystyrene Copolymer SP-8

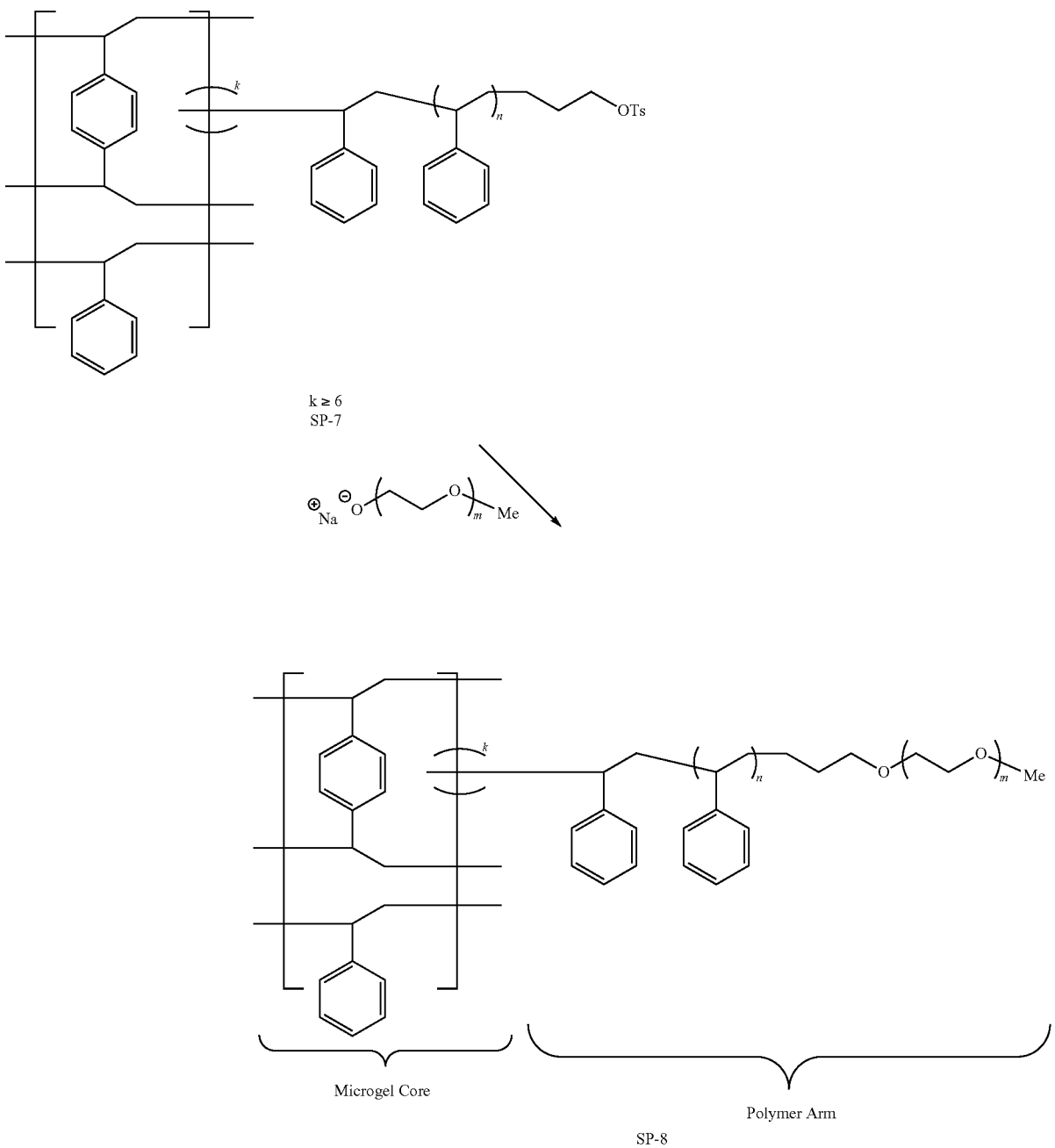

A suspension of sodium in mineral oil (40 wt %) (0.2 mL) was carefully added to a solution of dry poly(ethylene glycol) monomethyl ether (MPEG) ($M_n$=5000 g/mol, 0.5 g) in anhydrous toluene (7.0 mL) and stirred for 1 hour under a nitrogen atmosphere. A solution of tosylate-functionalized polystyrene star polymer SP-7 (See Example 4 (C) above) (0.1 g) in anhydrous toluene (3 mL) was then added, and the reaction was heated to 95° C. for 72 hour. The reaction solution was allowed to cool to room temperature before being carefully added dropwise to methanol (100 mL) with rapid stirring. The resulting solution was dialyzed against methanol (6000-8000 molecular weight cutoff (MWC)) before the solvent was removed to afford the star polymer SP-8 (0.2 g). $^1$H NMR (400 MHz, CDCl$_3$) delta (ppm)=1.00 (br s, 4 H), 1.43 (br s, 60 H), 1.79 (br s, 32 H), 3.26 (s, 2 H), 3.38 (s, 3 H), 3.47-3.90 (s, 180 H), 6.50-6.80 (br m, 60 H), 7.09 (br s, 90 H). $v_{max}$ (Thin Film): 3081.9 s, 3059.2 s, 3025.7 s, 2921.2 s 2921.2 br s, 2866.7 br s, 1946.5 m, 1875.1 m, 1805.7 m, 1748.5 m, 1670.8 m, 1601.2 s, 1492.9 s, 1452.6 s, 1349.3 s, 1298.8 s, 1249.9 m, 1113.1 br s, 1030.6 s cm$^{-1}$.

Example 6

Polystyrene-tar Polymer Peripherally Functionalized with Atom Transfer Radical Polymerization (ATRP)-initiator Moiety (Sp-9)

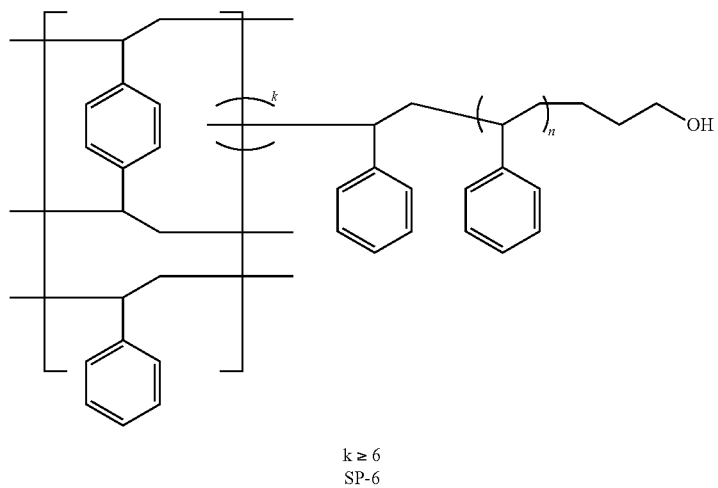

k ≥ 6
SP-6

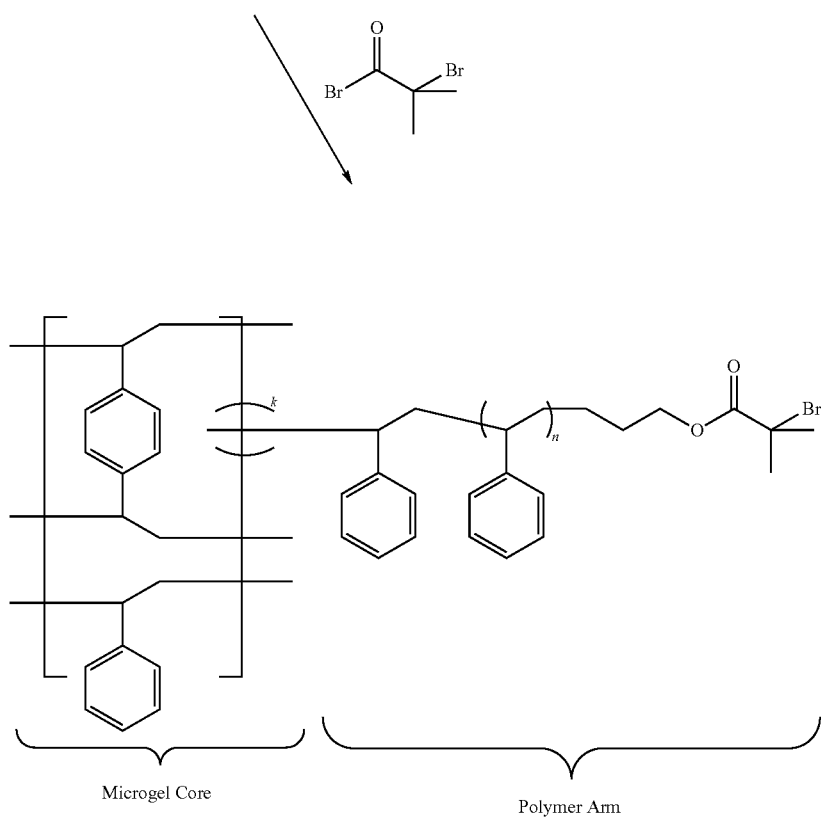

SP-9

A solution of 2-bromoisobutyryl bromide (1.4 g, 4 equivalents per star polymer alcohol end group) in anhydrous dichloromethane (30 mL) was added dropwise over 15 minutes to a solution of hydroxyl-PS star polymer (5.0 g) (see SP-6, Example 4B) and triethylamine (0.75 g) in anhydrous dichloromethane (30 mL) at 0° C. The mixture was allowed to warm up to room temperature for 14 hours, then heated to a gentle reflux for 4 hours. Pure product SP-9 was obtained after repeated precipitation into methanol. GPC and DLS analysis showed no significant change from that of the OH- star polymer starting material. 1H NMR (CDCl3, 4000 MHz) characterization of the product confirmed quantitative end-group transformation.

Example 7

Polystyrene Star Polymer Terminated with Random Copolymer Derived from Dimethylaminoethyl Methacrylate (DMAEMA) and Oligo(Polyethylene Glycol) Methacrylate (EGM), SP-10

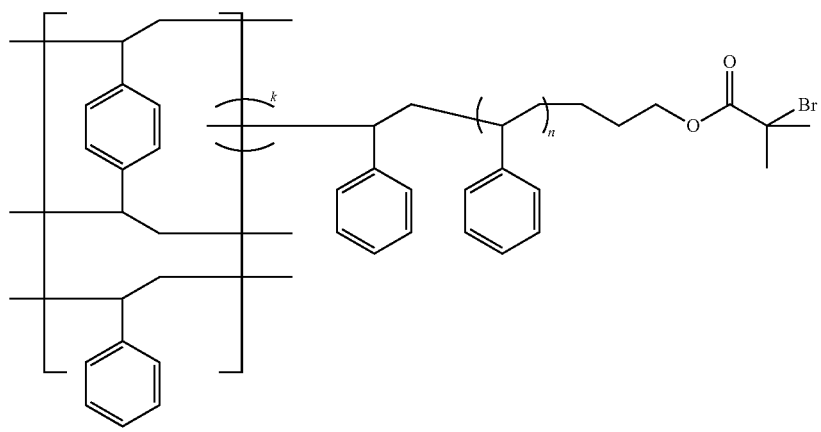

SP-9

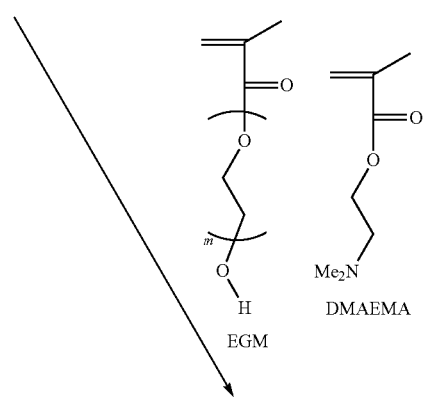

EGM   DMAEMA

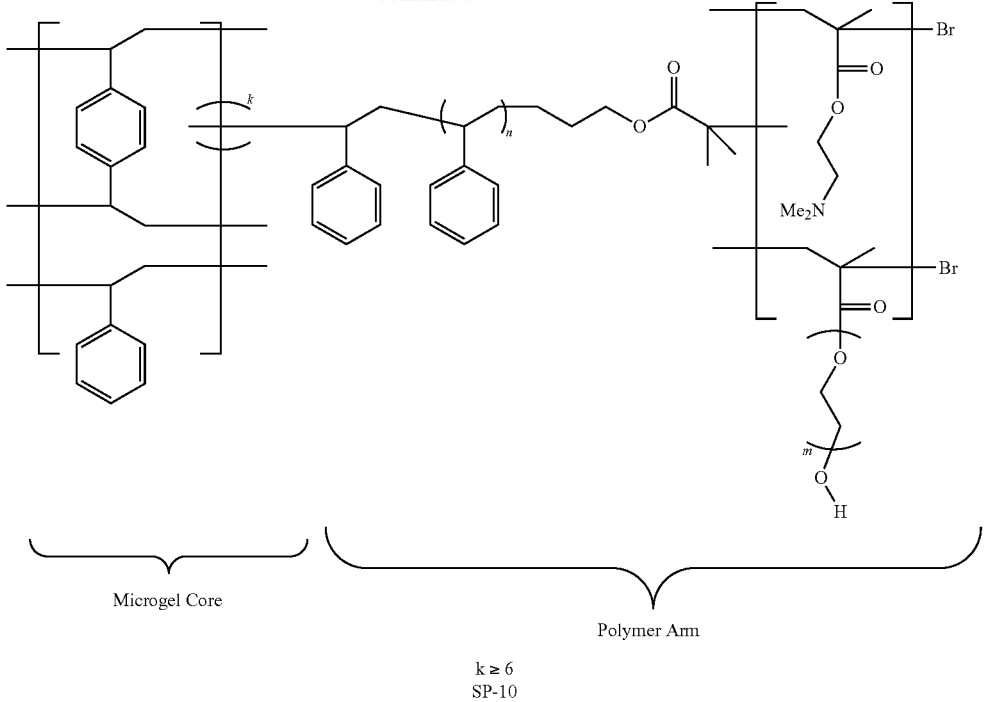

Microgel Core / Polymer Arm k ≥ 6
SP-10

ATRP-initiator peripherally functional polystyrene (PS) star polymer SP-9 (0.2 g), N,N-dimethylaminoethyl-methacrylate (DMAEMA) (0.7 g), oligo(ethylene glycol) methacrylate (EGM) (DP 4.5, 0.4 g), cupper(I) chloride (5.4 mg) and 4,4'-nonyl-2,2'-bipyridine (45.0 mg) were dissolved in toluene (5.0 mL). The solution was degassed and sealed under a nitrogen atmosphere before being heated to 90° C. for 15 hours. The reaction solution was then cooled and added to hexane (50 mL) with rapid stirring. The precipitate thus formed was isolated, dissolved in methylene chloride and again added to hexane (50 mL) with rapid stirring. The precipitate thus formed was isolated and air dried to a constant weight to produce star polymer SP-10 (0.4 g) as a white solid. $^1$H NMR (400 MHz, CDCl$_3$) delta (ppm)=0.90 (br s, 24 H), 1.08 (br s, 14 H), 1.45 (br s, 74 H), 1.86 (br s, 77 H), 2.33 (br s, 54 H), 2.63 (br s 24), 3.41 (br s, 9 H), 3.59 (br s, 6H), 3.69 (br s, 42 H), 4.11 (br s, 22), 6.50-6.60 (br m, 70 H), 7.13 (br s, 105 H). Analytical GPC (THF): retention time 25.6 min, $M_w/M_n$=1.14. DLS (THF): $M_w$=97,000 g/mol, $M_w/M_n$=1.06, hydrodynamic radius $R_{h(avg)}$=14.0 nm.

Examples 8-10

Loaded Star Polymers

The following procedure employing hydrophobic solvatochromic dyes represents a general method for preparing water based formulations comprising nanoparticles of amphiphilic star polymers loaded with pharmaceutical materials, using hydrophobic/hydrophilic interactions.

A solution was prepared containing hydrophobic dye material (5 mg) and core-shell ROP star-polymer SP-1 from Example 1 (25.0 mg, approximately 0.1 micromoles) in THF (0.1 mL, about 10 mM). The solution was added drop-wise to water (0.9 mL) with rapid stirring, causing the water to rapidly and uniformly color from the dye. Excess solid dye material not adsorbed to the star polymer was removed by passing the mixture through a 0.2 micrometer syringe filter, thereby forming a clear and uniformly colored aqueous solution. The further addition of water had no visible effect on the homogeneity of the solution. UV-Visible absorption spectra of the aqueous formulations containing the various solvatochromic dye materials were used to demonstrate the association of these model hydrophobic materials with the star polymer in the aqueous environment.

Example 8 is a loaded star polymer prepared by the above procedure using the hydrophobic dye dansyl butyl ester (DBE), wherein the dye is bound to the star polymer by hydrophobic interactions (i.e., adsorption, rather than covalent binding as in Example 3):

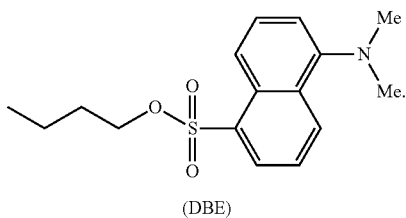 [SMILES: CCCCOS(=O)(=O)c1cccc2c(N(C)C)cccc12]

(DBE)

FIG. 3 compares the UV-Visible absorption spectra of a solution of dansyl butyl ester (DBE) in different organic solvents, with the aqueous loaded star polymers of Example 3 and Example 8. Table 7 summarizes the solvatochromic data for DBE alone in the various solvents with Example 8 loaded nanoparticle in water (labeled Aqueous Formulation A in Table 7). The lamda max of the dye alone varies from 452 nm-538 nm. The loaded nanoparticle in water has a lamda max of 515 nm.

TABLE 7

| Lamda$_{Em\ Max}$ (nm) | Dye Environment | Environment Polarity |
|---|---|---|
| 452 | Cyclohexane | 0.2 |
| 483 | Diethyl Ether | 2.7 |
| 502 | Tetrahydrofuran | 4.0 |
| 507 | Ethyl Acetate | 4.4 |
| 515 | Aqueous Formulation A | |
| 528 | Methylethyl Ketone | 4.7 |
| 532 | Dimethylformamide | 6.4 |
| 538 | Dimethylsulfoxide | 7.2 |
| NA | Water | 10.2 |

Example 9 is a loaded star polymer prepared by the above described procedure using the hydrophobic dye nile red (NR):

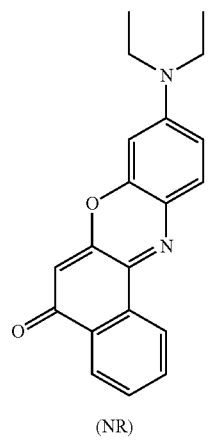

(NR)

Table 8 compares the solvatochromic data for Nile Red alone in various solvents with the Example 9 loaded star polymer in water (labeled Aqueous Formulation B in Table 8). The lamda max of the dye alone varies from 491 nm-553 nm. The loaded nanoparticle in water has a lamda max of 548 nm.

TABLE 8

| Lamda max (nm) | Dye Environment | Environment Polarity |
|---|---|---|
| 491 | Cyclohexane | 0.2 |
| 511 | Diethyl Ether | 2.7 |
| 528 | Tetrahydrofuran | 4.0 |
| 523 | Ethyl Acetate | 4.4 |
| 539 | Methylethyl Ketone | 4.7 |
| 543 | Dimethylformamide | 6.4 |
| 548 | Aqueous Formulation B | |
| 553 | Dimethylsulfoxide | 7.2 |
| NA | Water | 10.2 |

Figure 4A:
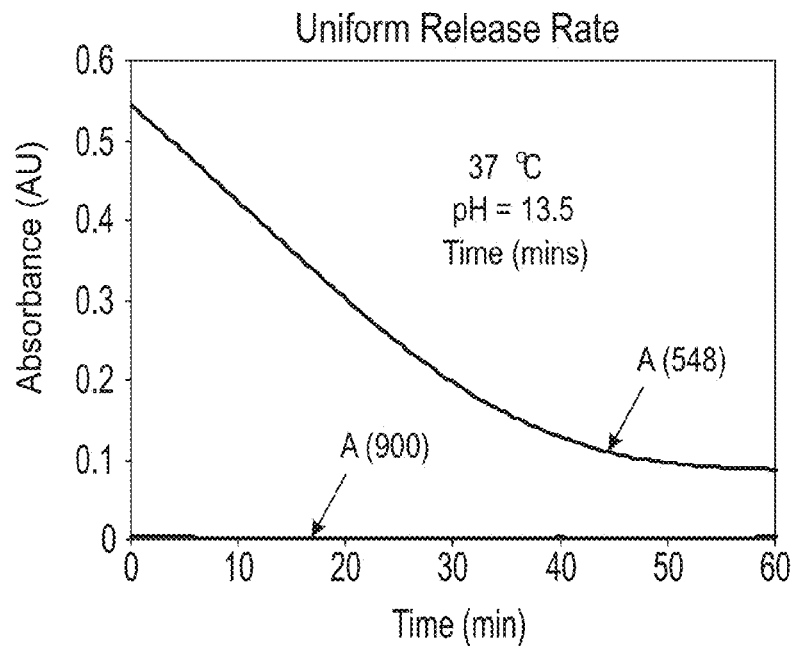
FIGS. 4A and 4B are graphs showing the release rates of Nile Red as the star polymer carrier undergoes hydrolytic degradation, as measured by the UV-Visible absorbance at 548 nm with time.
Figure 4B:
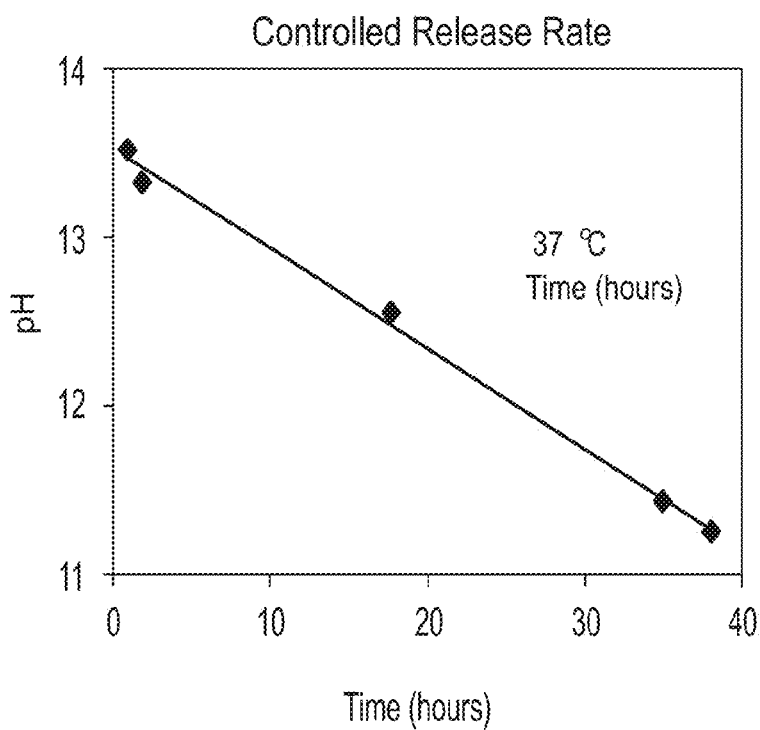

FIGS. 4A and 4B are graphs showing the release rates of Nile Red as the star polymer carrier undergoes hydrolytic degradation, as measured by the UV-Visible absorbance at 548 nm with time. FIG. 4A shows the total loss of dye within 60 minutes at a temperature of 37° C. and a pH of 13.5. The near infrared absorbance at 900 nm is also shown for comparison. FIG. 4B shows the effect of pH on the release rate, and indicates the release time can be extended to approximately 100 hours by lowering the pH to about 7.5.

Figure 5A:
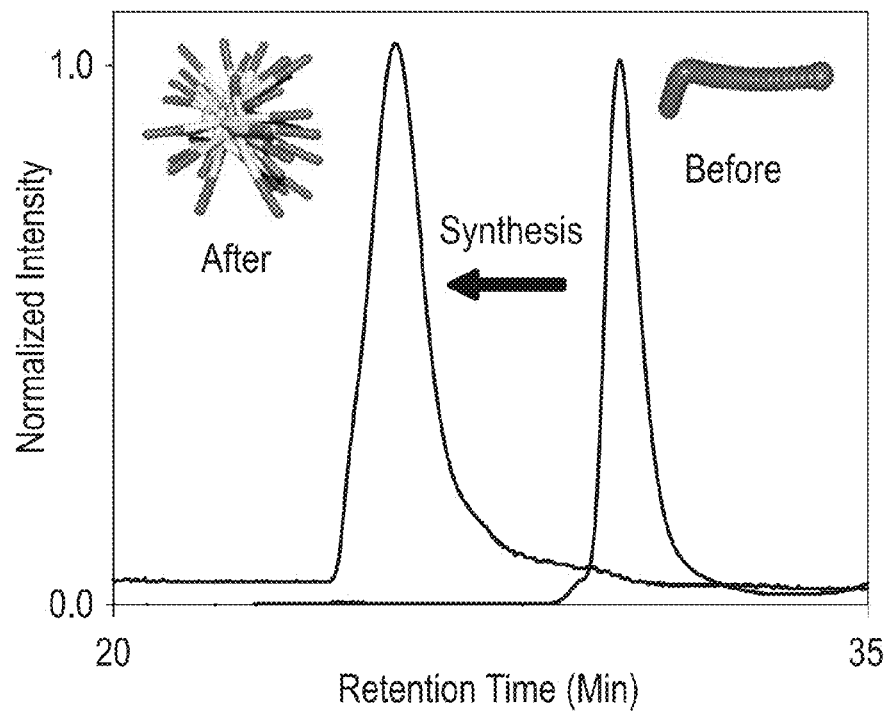
FIGS. 5A and 5B are gel permeation chromatographs (GPC) showing the hydrolytic degradation of the loaded star polymer of Example 9, which releases the mono methyl poly(ethylene glycol) of the polymer arm. The peak on the right side of the graph is the mono methyl poly(ethylene glycol) portion of the polymer arm (in FIG. 5A before synthesis of the star polymer, and in FIG. 5B after hydrolytic degradation of the loaded star polymer). The peak on the left is the loaded star polymer.
Figure 5B:
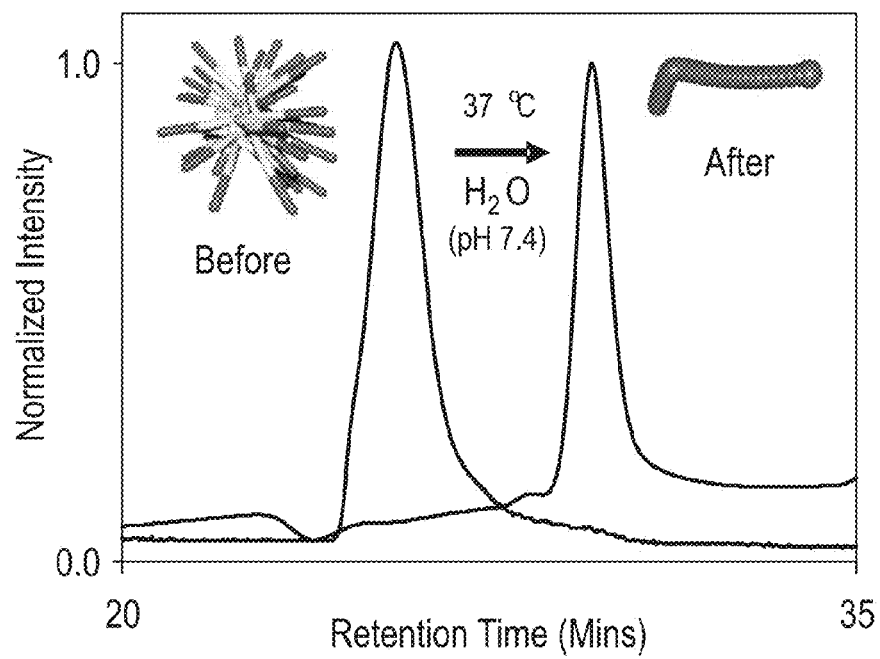

FIGS. 5A and 5B are gel permeation chromatographs (GPC) of the loaded star polymer of Example 9 before and after hydrolytic degradation of the star polymer. The peak on the right side of the graph is the mono methyl poly(ethylene glycol) fragment of the polymer arm. The peak on the left is the loaded star polymer.

Example 10 is a loaded star polymer prepared by the above described procedure using tert-butyl phthalocyanine (TBP), a potential image contrast enhancing agent.

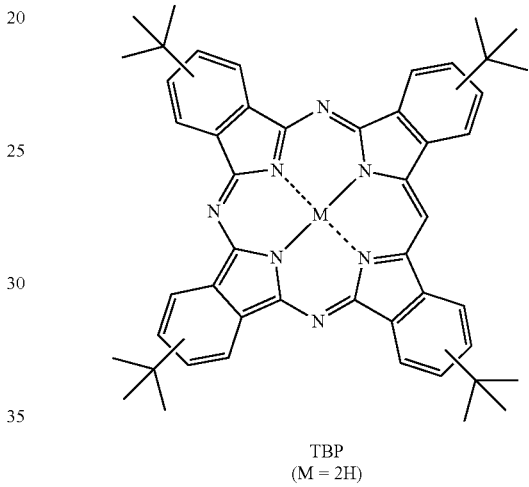

TBP
(M = 2H)

Figure 6:
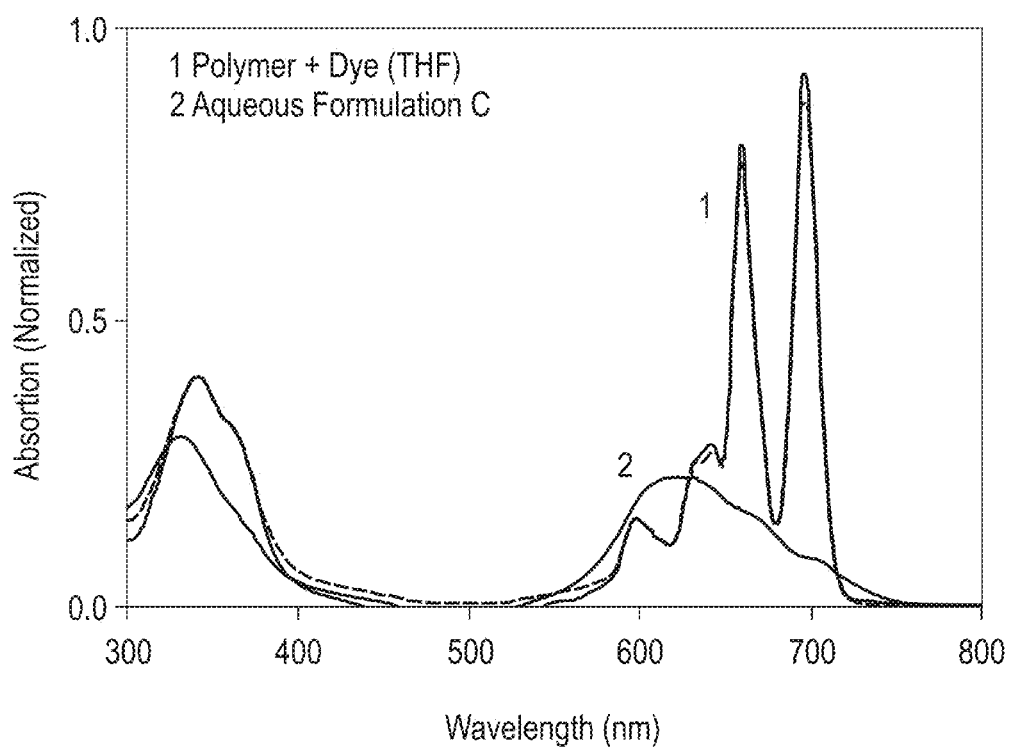
FIG. 6 is a graph comparing the UV-Visible absorption spectrum of a solution of the star polymer of Example 1 and TBP dye in THF (curve labeled 1) with an aqueous solution of the loaded star polymer comprising TBP (curve labeled 2).

FIG. 6 is a graph comparing the UV-Visible absorption spectrum of a solution of the star polymer of Example 1 and TBP dye in THF (curve labeled 1) with an aqueous solution of the star polymer loaded with TBP (curve labeled 2). Example 11. Comparison of metal and organic catalysts in ROP polymerizations. The results indicate that a significant portion of the adsorbed porphyrin in the star polymer is in a non-aggregated state.

Example 11

Comparison of Metal and Organic Catalysts in ROP Polymerizations

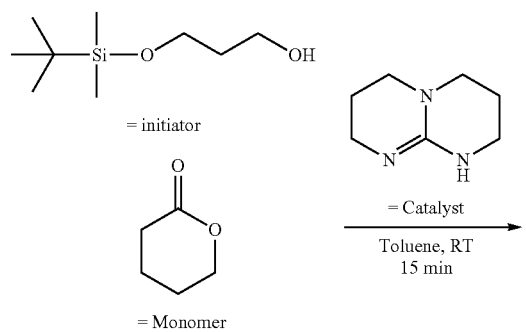

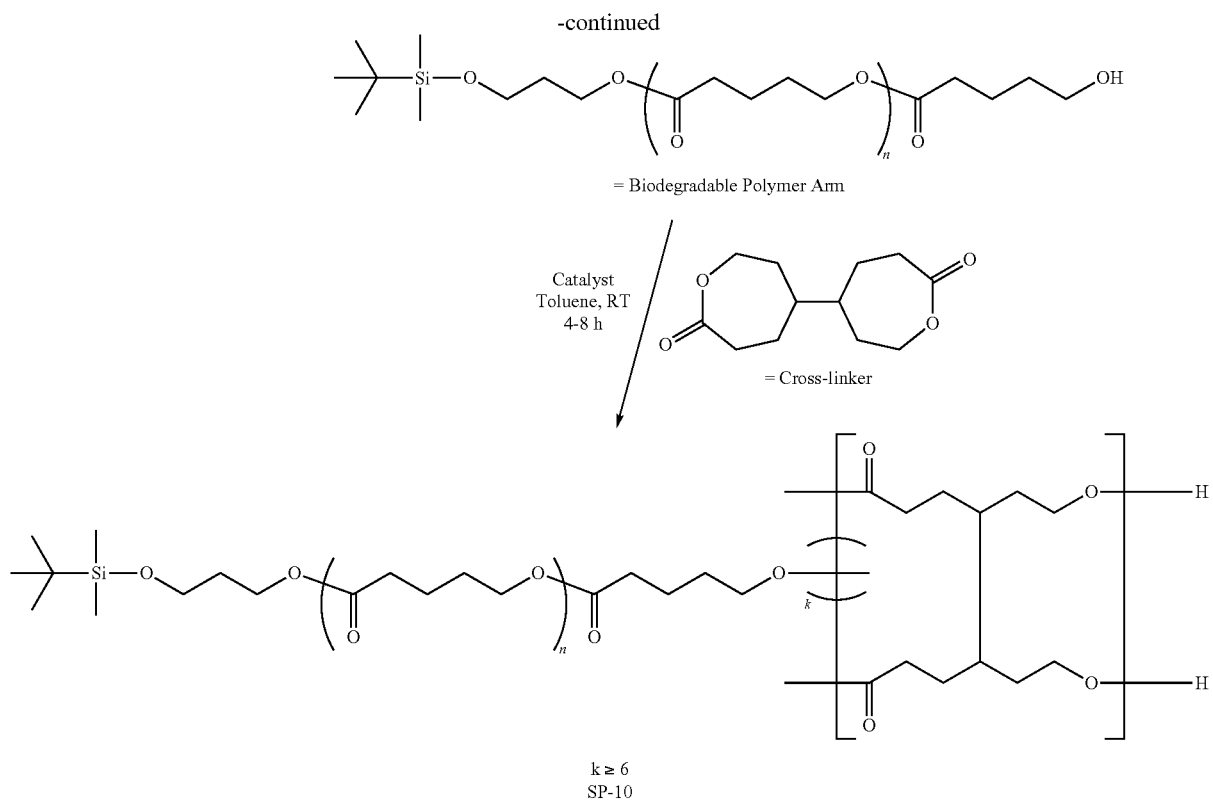

k ≥ 6
SP-10

A polymer arm was constructed by ROP polymerization of delta-valerolactone, initiated by t-butyldimethylsilyl-1-propanol, and catalyzed by organocatalyst 1,5,7-triazabicyclo[4.4.0]dec-5-ene (TBD). The microgel core was generated by ROP polymerization of bis-epsilon-caprolactone using the same catalyst, thereby generating star polymer SP-10. Thus, a solution of delta-valerolactone (10.0 g, 99.9 mmol) in 12.8 g of toluene (dry) was added to a stirring solution of tert-butyldimethylsilyl-1-propanol (0.6 g, 3.5 mmol, [VL]$_o$/[Initiator]$_o$=30) and TBD (72.0 mg, 0.5 mmol) in 30 g of toluene (dry) under a nitrogen atmosphere and allowed to stir at room temperature to yield the linear polymer arm. After 15 min a solution of BOD (3.8 g, 16.6 mmol, [BOD]$_o$/[Arm]$_o$=5) and TBD (72.0 mg, 0.5 mmol) in 96.0 g toluene (dry) was added quickly to the reaction mixture and allowed to stir at room temperature for a further 16 hours. The reaction mixture was then precipitated from cold methanol, filtered, and dried at room temperature under 100 mmHg. The crude polymer (10.8 g) was dissolved in 200 mL of acetone and 230 mL of methanol was added slowly, forming an emulsion. The emulsion was allowed to settle overnight, forming yellow oil on the bottom of the flask. The solution was decanted off and the oil was dissolved in a minimum amount of acetone and precipitated from cold methanol, filtered, and dried yielding the star polymer SP-10 as a white amorphous polymer (5.3 g, 49%). $^1$H NMR (CDCl$_3$, 400 MHz): delta (ppm)=4.06 (br, 118H, —CH$_2$—CH$_2$—OOC—), 3.65 (br, 4H, —CH$_2$—O—Si— and from the core —CH$_2$—OH), 2.32 (br, 118H, —CH$_2$—CH$_2$—COO—), 1.81-1.61 (br, 258H, —OOC—CH$_2$—CH$_2$—CH$_2$—CH$_2$—OOC—, Si—O—CH$_2$—CH$_2$—CH$_2$—OOC—), 0.86 (s, 9H, CH$_3$—C—Si—), 0.02 (s, 6H, CH$_3$—Si—). GPC(RI): Mn (PDI)=53 300 g/mol (1.26). DLS (RI): Mn=333 000 g/mol, PDI=1.32, R$_h$=5.5 nm.

The procedure was repeated using a metal catalyst, Sn(Oct)$_2$ and the method described in J. T. Wiltshire and G. G. Qiao, *Macromolecules*, 2006, 39, 9018-27 in order to compare the molecular weight distribution of the products. Delta-valerolactone (1.0 g, 10.0 mmol) was added to a mixture of toluene (8.8 mL), tert-butyldimethylsilyl-1-propanol (52.2 mg, 0.3 mmol), and Sn(Oct)$_2$ (27.3 microliters, 0.1 mmol). A condenser and CaCl$_2$ drying tube were attached to the flask, which was then heated at 110° C. with stirring. After 24 hours a solution of BOD (0.4 g, 1.7 mmol) in 1.5 mL of chloroform was injected into the reaction mixture and left to react for a further 16 hours. The reaction mixture was then cooled, and the solvent was removed under reduced pressure with the crude polymer being dissolved in THF and precipitated into methanol. The precipitate was collected by filtration and dried under vacuum.

Figure 7A:
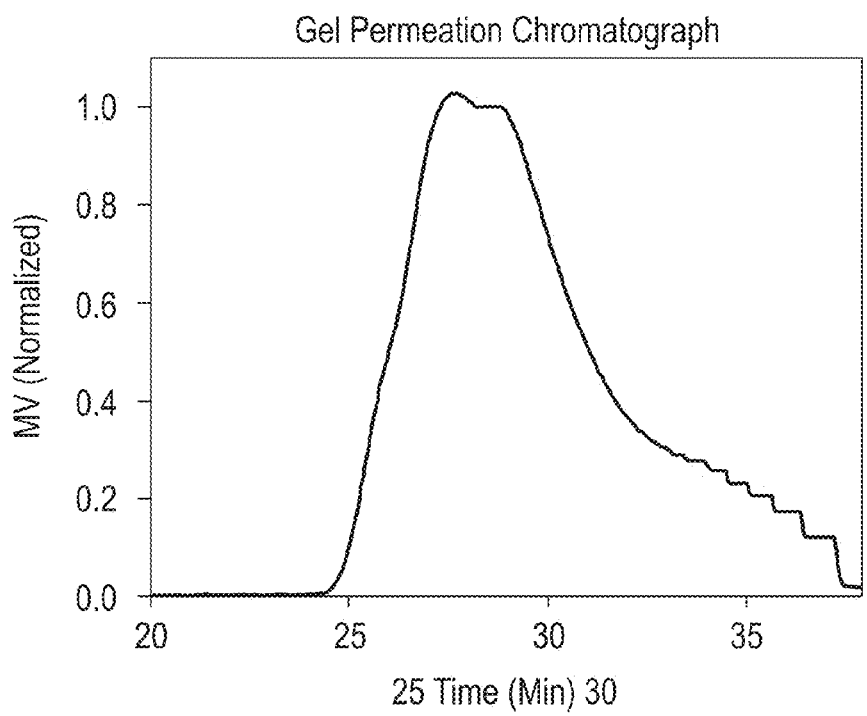
FIGS. 7A and 7B are gel permeation chromatographs showing the difference in molecular weight distribution of the crude star polymer of Example 11 formed by each of two catalysts, a metal catalyst $Sn(Oct)_2$ and organocatalyst 1,5,7-triazabicyclo[4.4.0]dec-5-ene (TBD).
Figure 7B:
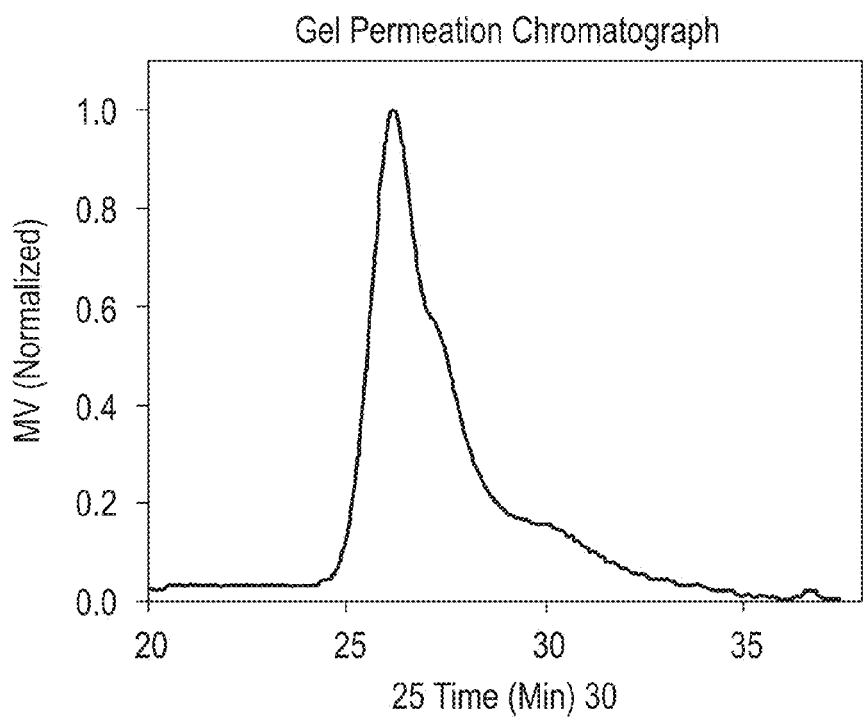

FIGS. 7A and 7B are gel permeation chromatographs of the crude SP-10 formed by each catalyst. The molecular weight distribution is much narrower with the organic catalyst TBD. Thus, the organic catalyst provides a significant advantage in controlling the physical and solution properties of these biodegradable materials.

Example 12

Loaded Star Polymer

The above-described procedure of Examples 8-10 was used to prepare a loaded star polymer containing star polymer SP-1 and 5,10,15,20-(3,5-ditertbutylphenyl)porphyrin (M=2H) (DTBP):

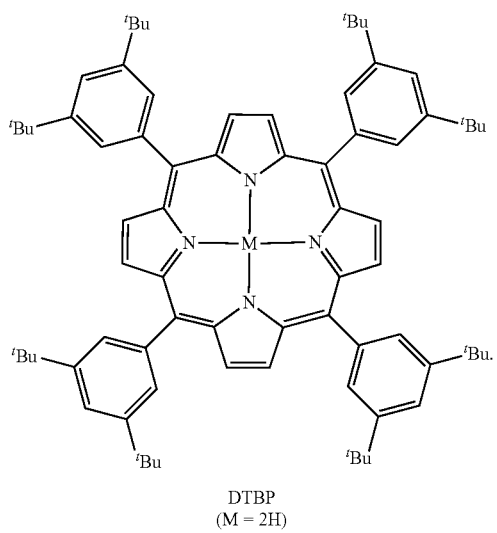

DTBP
(M = 2H)

Figure 8:
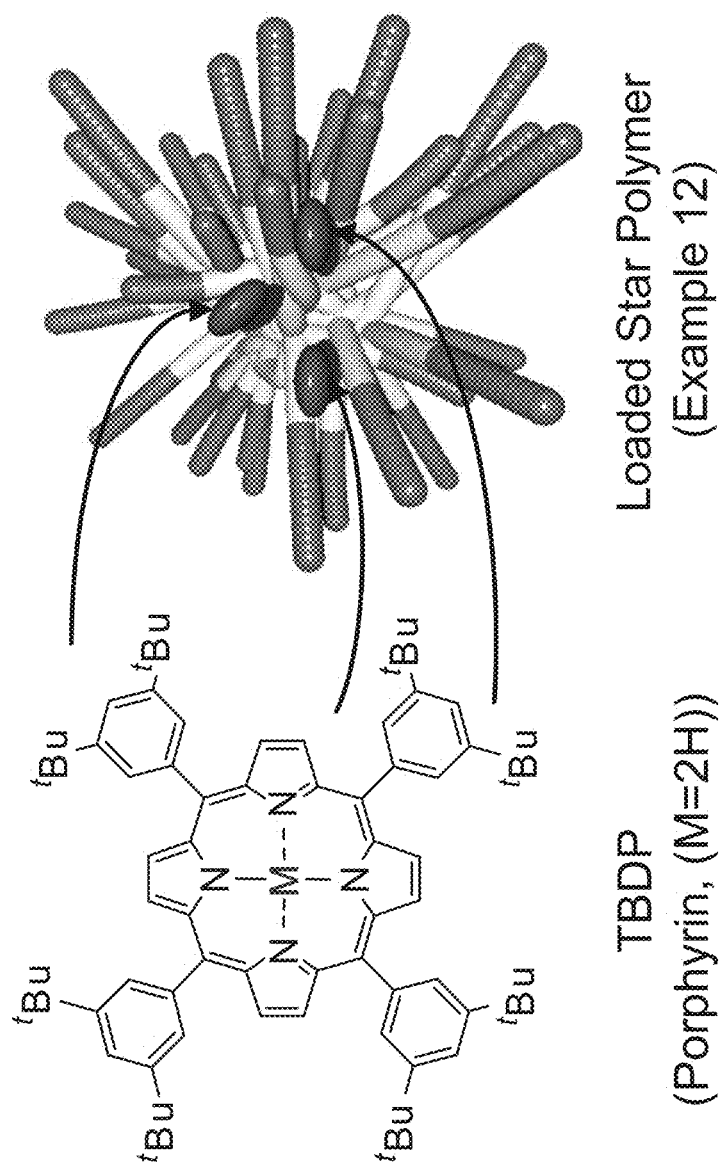
FIG. 8 is an illustration of a molecular model exemplifying what is believed to be the 3-dimensional structure of the loaded star polymer of Example 12, in this case containing three molecules (although not limited to three) of the porphyrin dye occluded in the star polymer arms.
Figure 9:
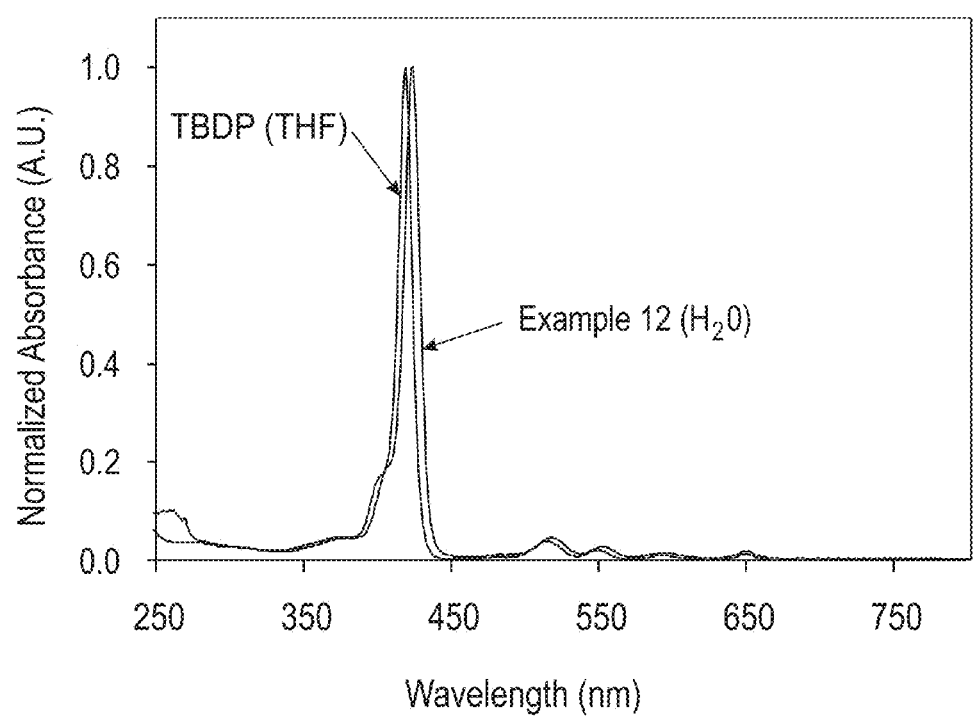
FIG. 9, a graph of the UV-Visible absorption curve of the loaded star polymer of Example 12, which essentially overlaps with the absorption curve of the porphyrin dye DTBP (M=2H) alone in THF.

FIG. 8 is an illustration of a molecular model exemplifying what is believed to be the 3-dimensional structure of the loaded star polymer, in this case with three molecules of the porphyrin dye DTBP (although not limited to three) occluded in a loaded star polymer arms. The porphyrin dye is believed to be in contact with the inner hydrophobic polymer chain segment of the polymer arms and the hydrophobic microgel core. Evidence of this is shown in FIG. 9, a graph of the UV-Visible absorption curve of the loaded star polymer, which essentially overlaps with the absorption curve of the porphyrin dye DTBP alone in THF.

Figure 10:
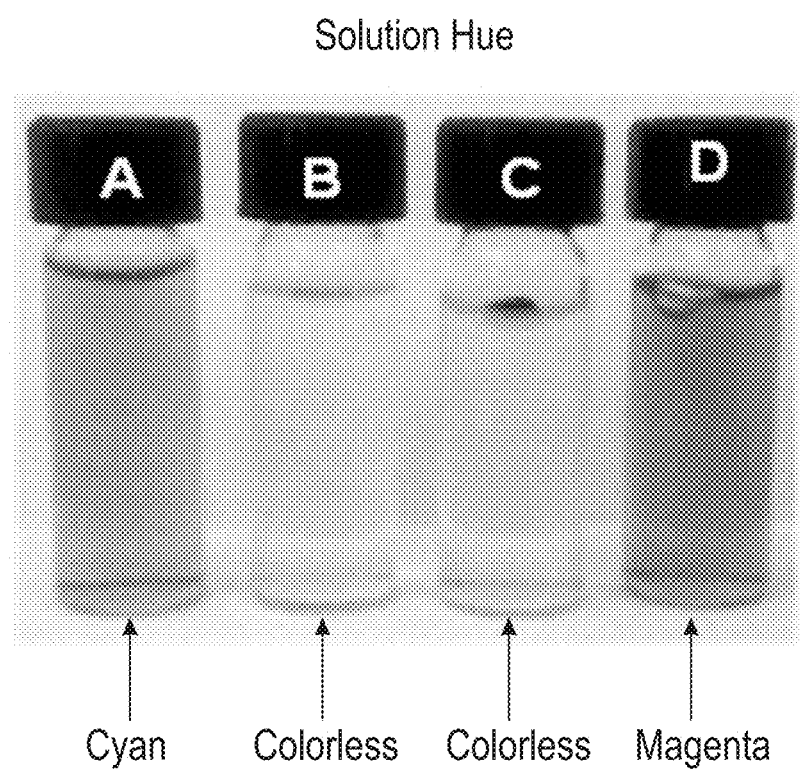
FIG. 10 is a photograph of four aqueous mixtures. Vials labeled A and D contain the loaded star polymers of Example 10 and Example 12, respectively. Vial B contains the star polymer of Example 1 alone. Vial C contains porphyrin DTBP (M=2H) alone. Vial A has a cyan hue, vials B and C are colorless, and vial D is magenta.

FIG. 10 is a photograph of four aqueous mixtures. The vial labeled A is an aqueous solution of the loaded star polymer of Example 10 (star polymer SP-1 occluded with tert-butyl phthalocyanine (M=2H)). The solution is clear and has a cyan hue. The vial labeled B is a solution of the star polymer SP-1 (Example 1) alone in water. The solution is clear and colorless. The vial labeled C is an aqueous mixture of 5,10,15,20-(3,5-ditertbutylphenyl)porphyrin (M=2H) (DTBP) alone in water. The aqueous mixture is clear and colorless. The vial labeled D is an aqueous mixture of the loaded star polymer of Example 12 containing DTBP (M=2H) occluded in the star polymer SP-1. The aqueous mixture is clear and has a magenta hue.

In summary, compositions comprising a water soluble, amphiphilic core-shell star polymer structures have been disclosed comprising no more than 100 ppm of a restricted metal as defined herein. The star polymers comprise a hydrophilic outer shell, a hydrophilic inner shell, and a living polymeric microgel core. The star polymers can further comprise specific sites for chemical interaction which can exist in either the outer, inner and/or core region. The polymeric microgel core conjoins the amphiphilic polymer arms of the star polymer. The hydrophobic inner shell and the hydrophilic outer shell can be of varying size through either the use of differing lengths of the polymeric units which comprise these sections or through the use of preformed hydrophobic core and arm sections of varied size. The incorporation of polymeric components of varying bio-compatibilities (e.g., non-immunogenic, biodegradable, and/or biocompatible) is a specific advantage of these structures. The star polymers form stable dispersions in water and in particularly buffered aqueous solutions of physiological relevance, and can be loaded with biologically active cargo materials. The synthesis of the unimolecular star polymers employs biocompatible compositions using biocompatible polymerization techniques in a one-pot "arm first/living core" approach. The use of non-toxic organic catalysis for the ring opening polymerization of monomers known to produce biocompatible polymers is another key advantage of these materials. The use of bis-monomers of similar constitution to form the living polymer core of the star polymer is another key advantage. The use of initiators containing additional latent functionality provides access to generating peripheral functionality into the star polymer structures. The living nature of the microgel core provides a convenient means to generate interior functionality onto the star polymer structure. The use either living polymer arms formed in situ in a "two step, one pot" process or suitable functionalized preformed polymer arms in a "one-step, one-pot" process is also advantageous. The living polymer arms can be amphiphilic block copolymers of biocompatible constitution, which can provide direct access to unimolecular micellar type core-shell star polymer materials. This invention also describes a method for providing water-based formulations of water soluble, amphiphilic, microgel based star polymers and pharmaceutical materials in which the pharmaceutical agent is associated with the polymeric carrier through non-covalent interaction. The loaded nanoparticles can comprise large biologically active cargo materials, facilitated by hydrophobic/hydrophilic interactions to associate hydrophobic pharmaceuticals in aqueous environments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:
1. A composition of matter, comprising:
a water soluble biodegradable amphiphilic star polymer, the star polymer comprising a crosslinked living microgel core and 6 or more independent polymer arms covalently linked to the core, the 6 or more arms each comprising a hydrophilic polymer chain segment and a hydrophobic polymer chain segment; wherein each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million, and wherein the microgel core comprises a polymer segment selected from the group consisting of polyesters, polycarbonates, polycarbamates, polyureas, polyithiocarbamates, polyithiocarbonates, polydithiocarbonates, and combinations thereof.

2. The composition of claim 1, wherein the microgel core comprises 6 or more sites capable of further synthetic transformation, the sites including a functional group selected from the group consisting of alcohols, amines, carboxylic acids, azides, alkynes, alkenes, halogen groups, and combinations thereof.

3. The composition of claim 1, wherein each of the 6 or more polymer arms comprises a backbone segment selected from the group consisting of polyesters, polycarbonates, polycarbamates, polyureas, polythiocarbamates, polythiocarbonates, polydithiocarbonates, and combinations thereof.

4. The composition of claim 1, wherein the star polymer is biodegradable in accordance with ASTM D6400.

5. The composition of claim 1, wherein the star polymer has a polydispersity index of less than or equal to 1.35.

6. The composition of claim 1, wherein one or more of the 6 or more polymer arms comprises a side chain functional group selected from the group consisting of urea groups, carboxylic ester groups, carboxylic acid groups, carboxylic acid salts, latent carboxylic acid groups, quaternary amine groups, tertiary amine groups, secondary amine groups, primary amine groups, azides, alkynes, poly(alkylene ether) groups, and combinations thereof.

7. A composition, comprising:
a loaded star polymer comprising a water soluble biodegradable amphiphilic star polymer and a hydrophobic biologically active material occluded therein, the star polymer comprising a living microgel core of crosslinked polymeric material and 6 or more independent polymer arms covalently linked to the core, the 6 or more arms each comprising a hydrophilic polymer chain segment and a hydrophobic polymer chain segment, wherein i) the core includes 6 or more sites capable of further synthetic transformation, ii) each of the 6 or more sites includes a functional group selected from the group consisting of alcohols, amines, carboxylic acids, azides, alkynes, alkenes, halogen groups, and combinations thereof, iii) each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million, iv) the microgel core is a polymer selected from the group consisting of polyesters, polycarbonates, polycarbamates, polyureas, polythiocarbamates, polythiocarbonates, polydithiocarbonates, and combinations thereof, v) the biologically active material is bound by noncovalent interactions with the microgel core and/or with the 6 or more independent polymer arms, vi) the biologically active material is selected from the group consisting of drugs, genes, dyes, image contrast enhancing materials, and combinations thereof.

8. The composition of claim 7, wherein the biologically active material is an image contrast enhancing material, and the image contrast enhancing material is a porphyrinoid compound.

9. A method, comprising:
agitating a mixture comprising i) a polymer arm precursor comprising an initiator group, a hydrophobic polymer chain segment, and a hydrophilic polymer chain segment, ii) a core precursor material comprising two or more polymerizable cyclic carbonyl groups, iii) an organocatalyst, iv) an optional accelerator, and v) an optional solvent, thereby forming a water soluble biodegradable amphiphilic star polymer by an organocatalyzed ring opening polymerization of the core precursor material; wherein a) the star polymer comprises a crosslinked living microgel core comprising a polymer segment selected from the group consisting of polyesters, polycarbonates, polycarbamates, polyureas, polythiocarbamates, polythiocarbonates, polydithiocarbonates, and combinations thereof, b) the star polymer comprises 6 or more independent polymer arms covalently linked to the core, the 6 or more polymer arms being derived from the polymer arm precursor, and the 6 or more arms each comprising a hydrophilic polymer chain segment and a hydrophobic polymer chain segment, and c) each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million.

10. The method of claim 9, wherein each of the 6 or more polymer arms comprises a peripheral hydrophilic polymer chain segment, and a hydrophobic polymer chain segment located nearest the microgel core.

11. The method of claim 9, wherein each of the 6 or more polymer arms comprises a peripheral hydrophobic polymer chain segment, and a hydrophilic polymer chain segment located nearest the microgel core.

12. The method of claim 9, wherein the polymer arm precursor comprises a backbone segment derived by ring opening polymerization of one or more cyclic carbonyl monomers.

13. The method of claim 9, wherein the polymer arm precursor comprises a backbone segment comprising a poly(alkylene ether).

14. The method of claim 9, wherein the organocatalyst comprises a nitrogen base comprising three or more nitrogens.

15. A method, comprising:
forming a mixture of a water soluble biodegradable amphiphilic star polymer and a hydrophobic biologically active material in an organic solvent; and
injecting the mixture into water, the water being a non-solvent for the biologically active material, thereby forming nanoparticles of a loaded star polymer comprising the star polymer and the biologically active material occluded therein; wherein i) the star polymer comprises a crosslinked living microgel core and 6 or more independent polymer arms covalently linked to the core, ii) the 6 or more polymer arms each comprise a hydrophobic polymer chain segment and a hydrophilic polymer chain segment, iii) each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million, iv) the microgel core comprises a polymer chain segment selected from the group consisting of polyesters, polycarbonates, polycarbamates, polyureas, polythiocarbamates, polythiocarbonates, polydithiocarbonates, and combinations thereof, and v) the biologically active material is bound by noncovalent interactions with the microgel core and/or with the 6 or more independent polymer arms, and vi) the biologically active material is selected from the group consisting of drugs, genes, dyes, image contrast enhancing materials, and combinations thereof.

16. The method of claim 15, wherein the microgel core and the 6 or more polymer arms each comprise a polymer segment independently selected from the group consisting of polyethers, polyesters, polycarbonates, polycarbamates, polythiocarbamates, polythiocarbonates, polydithiocarabonates, and combinations thereof.

17. The method of claim 15, wherein the biologically active material is a porphyrinoid compound.

18. An aqueous mixture comprising a loaded star polymer, the loaded star polymer comprising:
a water soluble biodegradable amphiphilic star polymer; and
a hydrophobic biologically active material occluded therein, wherein i) the star polymer comprises a crosslinked living microgel core and 6 or more independent polymer arms covalently linked to the core, the 6 or more arms each comprising a hydrophilic polymer chain segment and a hydrophobic polymer chain segment, wherein each individual metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table has a concentration in the star polymer of greater than or equal to 0 parts per million and less than or equal to 100 parts per million, ii) the biologically active material is bound by noncovalent interactions with the microgel core and/or with the 6 or more independent polymer arms, iii) the biologically active material selected from the group consisting of drugs, genes, dyes, image contrast enhancing materials, and combinations thereof, and iv) the microgel core comprises a polymer segment selected from the group consisting of polyesters, polycarbonates, polycarbamates, polyureas, polythiocarbamates, polythiocarbonates, polydithiocarbonates, and combinations thereof.

19. The aqueous mixture of claim 18, wherein the biologically active material is an image contrast enhancing material.

20. The aqueous mixture of claim 19, wherein the image contrast enhancing material is a porphyrinoid compound.

21. The aqueous mixture of claim 19, wherein the image contrast enhancing material is selected from the group consisting of

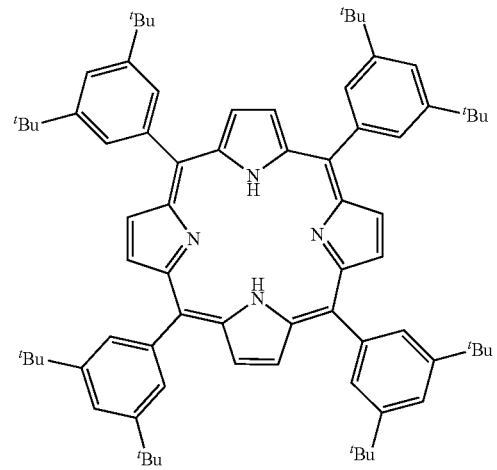

and

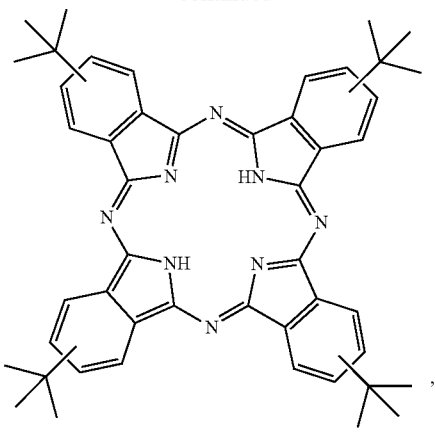

combinations thereof.

22. The aqueous mixture of claim 19, wherein 10% to 100% of the image contrast enhancing material is not aggregated in the star polymer.

23. The aqueous mixture of claim 19, wherein 50% to 100% of the image contrast enhancing material is not aggregated in the star polymer.

24. The composition of claim 1, wherein the polymer segment of the microgel core is a polyester.

25. The composition of claim 1, wherein the polymer segment of the microgel core is a polycarbonate.

26. The composition of claim 1, wherein the microgel core comprises a polystyrene chain segment.

27. The aqueous mixture of claim 18, wherein the polymer segment of the microgel core is a polyester.

28. The aqueous mixture of claim 18, wherein the polymer segment of the microgel core is a polycarbonate.

29. The aqueous mixture of claim 18, wherein the microgel core comprises a polystyrene chain segment.

30. The composition of claim 1, wherein the hydrophobic polymer chain segment is linked to the core, the hydrophilic polymer chain segment is a peripheral polymer chain segment linked to the hydrophobic polymer chain segment, and the hydrophilic polymer chain segment comprises i) a first repeat unit comprising a side chain amine group selected from the group consisting of quaternary amine groups, tertiary amine groups, secondary amine groups, primary amine groups, and combinations thereof, and ii) a peripheral end unit farthest from the core, the end unit comprising an alpha-haloester.

31. The composition of claim 30, wherein the amine group of the first repeat unit is a tertiary amine.

32. The star polymer of claim 30, wherein the hydrophilic polymer chain segment comprises a second repeat unit comprising a side chain monoester of an oligomeric poly(ethylene glycol).

33. The composition of claim 32, wherein the oligomeric poly(ethylene glycol) has an average degree of polymerization (DP) of about 4.5.

* * * * *